(12) United States Patent
Pulé et al.

(10) Patent No.: US 12,398,194 B2
(45) Date of Patent: *Aug. 26, 2025

(54) CELL LEXPRESSING TWO CHIMERIC ANTIGEN RECEPTORS (CARs) AT THE CELL SURFACE

(71) Applicant: AUTOLUS LIMITED, London (GB)

(72) Inventors: Martin Pulé, London (GB); Shaun Cordoba, London (GB); Shimobi Onuoha, London (GB); Simon Thomas, London (GB)

(73) Assignee: AUTOLUS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,754

(22) Filed: Jan. 24, 2023

(65) Prior Publication Data

US 2023/0331810 A1 Oct. 19, 2023

Related U.S. Application Data

(63) Continuation of application No. 16/785,467, filed on Feb. 7, 2020, now abandoned, which is a continuation of application No. 15/529,690, filed as application No. PCT/GB2015/054137 on Dec. 23, 2015, now Pat. No. 11,091,532.

(30) Foreign Application Priority Data

Dec. 24, 2014 (GB) ...................................... 1423172

(51) Int. Cl.
C07K 14/705 (2006.01)
A61K 35/00 (2006.01)
A61K 38/17 (2006.01)
A61K 39/00 (2006.01)
A61K 40/11 (2025.01)
A61K 40/31 (2025.01)
A61K 40/42 (2025.01)
C07K 14/725 (2006.01)
C07K 14/735 (2006.01)
C07K 16/28 (2006.01)
C07K 16/30 (2006.01)
C12N 5/0783 (2010.01)

(52) U.S. Cl.
CPC .... *C07K 14/70521* (2013.01); *A61K 38/1774* (2013.01); *A61K 40/11* (2025.01); *A61K 40/31* (2025.01); *A61K 40/4211* (2025.01); *A61K 40/4212* (2025.01); *C07K 14/7051* (2013.01); *C07K 14/70535* (2013.01); *C07K 16/2803* (2013.01); *C07K 16/2863* (2013.01); *C07K 16/3061* (2013.01); *C12N 5/0636* (2013.01); *C12N 5/0638* (2013.01); *A61K 35/00* (2013.01); *A61K 2039/505* (2013.01); *C07K 2317/31* (2013.01); *C07K 2317/622* (2013.01); *C07K 2319/03* (2013.01); *C07K 2319/74* (2013.01); *C12N 2501/505* (2013.01); *C12N 2501/599* (2013.01); *C12N 2510/02* (2013.01)

(58) Field of Classification Search
None
See application file for complete search history.

(56) References Cited

U.S. PATENT DOCUMENTS

| | | |
|---|---|---|
| 7,052,906 B1 | 5/2006 | Lawson et al. |
| 7,635,472 B2 | 12/2009 | Kufer et al. |
| 8,007,796 B2 | 8/2011 | Baeuerle et al. |
| 9,868,774 B2 | 1/2018 | Orentas et al. |
| 10,098,926 B2 | 10/2018 | Pule et al. |
| 10,174,099 B2 | 1/2019 | Pule et al. |
| 10,457,730 B2 | 10/2019 | Pule et al. |
| 10,981,970 B2 | 4/2021 | Puléet al. |
| 11,091,532 B2 | 8/2021 | Pule et al. |
| 11,180,553 B2 | 11/2021 | Onuoha et al. |
| 11,578,126 B2 | 2/2023 | Puléet al. |
| 11,590,170 B2 | 2/2023 | Puléet al. |
| 2004/0126363 A1 | 7/2004 | Jensen et al. |
| 2012/0134970 A1 | 5/2012 | Yang et al. |
| 2013/0266551 A1 | 10/2013 | Campana et al. |
| 2013/0287748 A1 | 10/2013 | June et al. |
| 2015/0023937 A1 | 1/2015 | Vera et al. |
| 2016/0296562 A1 | 10/2016 | Pule et al. |
| 2017/0340704 A1 | 11/2017 | Pule et al. |
| 2017/0340705 A1 | 11/2017 | Pule et al. |
| 2017/0369550 A1 | 12/2017 | Pule et al. |
| 2018/0044417 A1 | 2/2018 | Pule et al. |

(Continued)

FOREIGN PATENT DOCUMENTS

GB 1507111 A 4/1978
GB 1423172.4 12/2014

(Continued)

OTHER PUBLICATIONS

Bonini and Mondino (Eur. J. Immunol. 2015 45: 2457-2469) (Year: 2015).*
Chen and Flies (Nature Review Immunology, Apr. 2013, 12: 227-242) (Year: 2013).*
Almagro et al., Humanization of antibodies, Front. Biosci., 13:1619-33 (2008).
Amrolia et al., Chimeric Antigen Receptor T Cells for ALL, Lancet, 385:488-490 (2015).

(Continued)

*Primary Examiner* — Peter J Reddig
(74) *Attorney, Agent, or Firm* — MARSHALL, GERSTEIN & BORUN LLP

(57) ABSTRACT

The present invention provides a cell which co-expresses a first chimeric antigen receptor (CAR) and second CAR at the cell surface, each CAR comprising an antigen-binding domain, wherein the antigen-binding domain of the first CAR binds to CD19 and the antigen-binding domain of the second CAR binds to CD22.

20 Claims, 17 Drawing Sheets

Specification includes a Sequence Listing.

(56) References Cited

U.S. PATENT DOCUMENTS

| | | |
|---|---|---|
| 2018/0312570 A1 | 11/2018 | Pule et al. |
| 2018/0371054 A1 | 12/2018 | Pule et al. |
| 2019/0038672 A1 | 2/2019 | Pule et al. |
| 2019/0161531 A1 | 5/2019 | Pule et al. |
| 2019/0177412 A1 | 6/2019 | Onuoha et al. |
| 2019/0330337 A1 | 10/2019 | Pule et al. |
| 2020/0140544 A1 | 5/2020 | Pule et al. |
| 2020/0181232 A1 | 6/2020 | Puléet al. |
| 2021/0113618 A1 | 4/2021 | Puléet al. |
| 2021/0187026 A1 | 6/2021 | Pule et al. |
| 2022/0273710 A1 | 9/2022 | Puléet al. |
| 2024/0033289 A1* | 2/2024 | Pulé .................. A61K 39/0011 |

FOREIGN PATENT DOCUMENTS

| | | |
|---|---|---|
| GB | 1507111.1 | 4/2015 |
| WO | 00/63372 A1 | 10/2000 |
| WO | 2012/079000 A1 | 6/2012 |
| WO | 2013/059593 A1 | 4/2013 |
| WO | 2013/123061 A1 | 8/2013 |
| WO | 2013/185552 A1 | 12/2013 |
| WO | 2014/011988 A2 | 1/2014 |
| WO | 2014/055657 A1 | 4/2014 |
| WO | 2014/055668 A1 | 4/2014 |
| WO | 2014/065961 A1 | 5/2014 |
| WO | WO-2014/124143 A1 | 8/2014 |
| WO | 2014/138704 A1 | 9/2014 |
| WO | 2014/145252 A2 | 9/2014 |
| WO | 2014/184143 A1 | 11/2014 |
| WO | 2015/075468 A1 | 5/2015 |
| WO | 2015/075470 A1 | 5/2015 |
| WO | 2015/092024 A2 | 6/2015 |
| WO | 2015/142314 A1 | 9/2015 |
| WO | 2016/139487 A1 | 9/2016 |
| WO | 2016/174405 A1 | 11/2016 |
| WO | 2016/210293 A1 | 12/2016 |
| WO | 2017/216561 A1 | 12/2017 |
| WO | 2017/216562 A1 | 12/2017 |

OTHER PUBLICATIONS

Bejcek et al., Development and characterization of three recombinant single chain antibody fragments (scFvs) directed against the CD19 antigen, Cancer Res., 55(11):2346-51 (1995).

Brentjens et al., "Eradication of systemic B-cell tumors by genetically targeted human T lymphocytes co-stimulated by CD80 and interleukin-15," Nature Medicine 9(3):279-286 (2003).

Bridgeman, et al., "The Optimal Antigen Response of Chimeric Antigen Receptors Harboring the CD3(zeta) Transmembrane Domain is Dependent upon Incorporation of the Receptor into the Endogenous TCR/CD3 Complex," J. Immunol., 184(12): 6938-6949 (2010).

Burns, et al., "A High Molecular Weight Melanoma-Associated Antigen-Specific Chimeric Antigen Receptor Redirects Lymphocytes to Target Human Melanomas," Cancer Res; 70(8), pp. 3027-3033 (Apr. 2010).

Campana et al., Human B cell development. I. Phenotypic differences of B lymphocytes in the bone marrow and peripheral lymphoid tissue, J. Immunol., 134(3):1524-30 (1985).

Campana et al., Immunophenotyping of leukemia, J. Immunol. Methods, 243(1-2):59-75 (2000).

Chen, et al., "Fusion Protein Linkers: Property, Design and Functionality," Adv Drug Deliv Rev, 65(10):1357-1369 (Oct. 2013).

Chicaybam et al., "Moving Receptor Redirected Adoptive Cell Therapy Toward Fine Tuning of Antitumor Responses," International Reviews of Immunology 33:402-416 (2014).

Chmielewski, et al., "Antigen-specific T-cell activation independently of the MHC: chimeric antigen receptor-redirected T cells," Frontiers in Immunology, Tumor Immunity, 4(371):1-7 (2013).

Colman, "Effects of amino acid sequence changes on antibody-antigen interactions," Biomolecular Research Institute, 145(1): 33-36 (1994).

Cordoba, et al., "The large ectodomains of CD45 and CD148 regulate their segregation from and inhibition of ligated T-cell receptor," Blood, 121(21):4295-4302 (2013).

Courtney, et al., "TCR Signaling: Mechanisms of Initiation and Propagation," Trends Biochem Sci., 43(2):108-123 (Feb. 2018).

De Felipe, "Polycistronic Viral Vectors," Current Gene Therapy; 2(3):355-378 (2002).

Dijoseph et al., Antibody-targeted chemotherapy of B-cell lymphoma using calicheamicin conjugated to murine or humanized antibody against CD22, Cancer Immunol. Immunother., 54(1):11-24 (2005).

Dolezal, et al., "ScFv multimers of the anti-neuraminidase antibody NC10: shortening of the linker in a single-chain Fv fragment assembled in VL to VH orientation drives the formation of dimers, trimers, tetramers and higher molecular mass multimers," Protein Engineering, vol. 13, No. 8, pp. 565-574 (2000).

Donnelly et al., The 'cleavage' activities of foot-and-mouth disease virus 2A site-directed mutants and naturally occurrina '2A-like' sequences, J. Gen. Viral. 82: 1027-41 (2001 ).

Dorken et al., HD39 (B3), a B lineage-restricted antigen whose cell surface expression is limited to resting and activated human B lymphocytes, J. Immunol., 136(12):4470-9 (1986).

Dotti et al., Design and Development of Therapies using Chimeric Antigen Receptor-Expressing T cells, Immunol. Rev. 257:1-30 (2014).

Engel et al., Identification of the ligand-binding domains of CD22, a member of the immunoglobulin superfamily that uniquely binds a sialic acid-dependent ligand, J. Exp. Med., 181(4):1581-6 (1995).

Fedorov et al., "PD-1- and CTLA-4-Based Inhibitory Chimeric Antigen Receptors (iCARs) Divert Off-Taraet Immunotheraov Responses," Science Translation Medicine 5(215), 13 pages (2013).

Gerdes et al., Emerging understanding of multiscale tumor heterogeneity, Frontiers in oncology, 4:366 (2014).

Ghetie et al., "The Antitumor Activity of an Anti-CD22 Immunotoxin in SCIO Mice With Disseminated Daudi Lymphoma Is Enhanced by Either an Anti-CD19 Antibody or an Anti-CD19 Immunotoxin," Blood 80(9):2315-2320 (1992).

Grada et al., TanCAR: A Novel Bispecific Chimeric Antigen Receptor for Cancer Immunotherapy, Mol. Ther. Nucleic Acids, 2:e105 (2013).

Grupp et al., Chimeric antigen receptor-modified T cells for acute lumphoid leukemia. N. Engl. J. Med. 368(16): 1509-18 (2013).

Guedan et al., Enhancing CART cell persistence through ICOS and 4-1 BB costimulation., JCL Insight,. doi: 10.1172/jci.insight.96976 (2018).

Guha, et al., "Frontline Science: Functionally impaired geriatric CAR-T cells rescued by increased (alpha)5(beta)1 integrin expression," Journal of Leukocyte Biology, vol. 102, pp. 201-208 (Aug. 2017).

Haso et al., Anti-CD22-chimeric antigen receptors targeting B-cell precursor acute lymphoblastic leukemia, Blood, 121(7):1165-1174 (2013).

Hegde et al., Combinational targeting offsets antigen escape and enhances effector functions of adoptively transferred T cells in glioblastoma, Mol. Ther., 21(11):2087-101 (2013).

Hege, et al., "Safety, tumor trafficking and immunogenicity of chimeric antigen receptor (CAR)-T cells specific for TAG-72 in colorectal cancer," Journal for Immuno Therapy of Cancer, 5:22, pp. 1-14 (2017).

Herbst et al., B-cell depletion in vitro and in vivo with an afucosylated anti-CD19 antibody, J. Pharmacol. Exp. Ther., 335(1):213-22 (2010).

Hombach et al., Costimulation by Chimeric Antigen Receptors Revisited: the T Cell Antitumor Response Benefits from Combined CD28-OX40 Signalling, International Journal of Cancer, 129:2935-2944 (2011).

Hudecek et al., "The Nonsignaling Extracellular Spacer Domain of Chimeric Antigen Receptors Is Decisive for In Vivo Antitumor Activity," Cancer Immunoloav Research 3(2):125-135 (2015).

International Application No. PCT/GB2015/054137, International Preliminary Report on Patentability, mailed Jul. 6, 2017.

International Application No. PCT/GB2015/054137, International Search Report and Written Opinion, mailed Jun. 6, 2016.

(56) References Cited

OTHER PUBLICATIONS

James et al., Antigen sensitivity of CD22-specific chimeric TCR Is modulated by target epitope distance from the cell membrane, J. Immunol., 180:7028-7038 (2008).
Jena et al., Chimeric antigen receptor (CAR)-specific monoclonal antibody to detect CD19-specific T cells in clinical trials, PLOS One, 8:e57838 (2013).
Jena et al., Driving CAR-based T-cell therapy to success, Curr. Hematol. Malig. Rep., 9(1):50-6 (2014).
Jena et al., Redirecting T-cell specificity by introducing a tumor-specific chimeric antigen receptor, Blood, 116(7):1035-1044 (2010).
Jensen et al., Design and implementation of adoptive therapy with chimeric antigen receptor-modified t cells, Immunol. Rev., 257:127-44 (2014).
John et al., The B cell coreceptor CD22 associates with AP50, a clathrin-coated pit adapter protein, via tyrosine-dependent interaction, J. Immunol., 170(7):3534-43 (2003).
Kaiser, Cancer. First pass at cancer genome reveals complex landscape, Science, 8;313(5792):1370 (2006).
Kansas et al., Transmembrane signals generated through MHC class II, CD19, CD20, CD39, and CD40 antigens induce LFA-1-dependent and independent adhesion in human B cells through a tyrosine kinase-dependent pathway, J. Immunol., 147(12):4094-12 (1991).
Kipriyanov et al., "Two amino acid mutations in an anti-human CD3 single chain Fv antibody fragment that affect the yield on bacterial secretion but not the affinity," Protein Engineering 10(4):445-453 (1997).
Kipriyanov et al., Rapid detection of recombinant antibody fragments directed against cell-surface antigens by flow cytometry, J. Immunol. Meth. 196:51-62 (1996).
Kloss et al., "Combinatorial antigen recognition with balanced signaling promotes selective tumor eradication by engineered T cells," Nature Biotechnology 31 (1 ):71-75 (2013).
Kochenderfer et al., Construction and Pre-clinical Evaluation of an Anti-CD19 Chimeric Antigen Receptor, J. Immunother., 32(7):689-702 (2009).
Krauss et al., Specificity grafting of human antibody frameworks selected from a phage display library: generation of a highly stable humanized anti-CD22 single-chain Fv fragment, Protein Eng., 16(10):753-9 (2003).
Kreitman et al., Phase I trial of anti-CD22 recombinant immunotoxin moxetumomab pasudotox (CAT-8015 or HA22) in patients with hairy cell leukemia, J. Clin. Oncol., 30(15):1822-8 (2012).
U.S. Provisional Application filed on Jun. 25, 2015 by ICell Gene Therapeutics LLC, U.S. Appl. No. 62/184,321.
Vallera et al., "A Bispecific Recombinant Immunotoxin, DT2219, Targeting Human CD19 and CD22 Receptors in a Mouse Xenograft Model of B-Cell Leukemia/Lymphma," Clin Cancer Res 11(10):3879-3888 (2005).
Wen et al., The pan-B cell marker CD22 is expressed on gastrointestinal eosinophils and negatively regulates tissue eosinophilia, J. Immunol., 188(3):1075-82 (2012).
Wilkie et al., 1070Dual targeting of ErbB2 and MUC1 in breast cancer using chimeric antigen receptors engineered to provide complementary signaling, J. Clin. Immunol., 32:1059-1070 (2012).
Xiao et al., Identification and characterization of fully human anti-CD22 monoclonal antibodies, MAbs, 1(3):297-303 (2009).
Yang et al., Development of optimal bicistronic lentiviral vectors facilitates high-level TCR gene expression and robust tumor cell recognition, Gene. Ther., 15:1411-1423 (2008).
Yazawa et al., Immunotherapy using unconjugated CD19 monoclonal antibodies in animal models for B lymphocyte malignancies and autoimmune disease, Proc. Natl. Acad. Sci. USA, 102(42):15178-83 (2005).
Yokose, et al., "CD20-positive T cell leukemia/lymphoma: case report and review of the literature," Annals of Hematol., 80(6):372-375 (2001).
Krontiris et al., Internal medicine, 4th Edition, Editor-in-chief Jay stein, Elsevier science, Chapters 71-72:699-729 (1994).
Kumaresan et al., "Bioengineering T cells to target carbohydrate to treat opportunistic fungal infection", CrossMark, PNAS, 111:29, pp. 10660-10665 (Jul. 22, 2014).
Kumaresan et al., "Dual-Specificity CAR+ T Cells to Target B-Cell Malignancies and Opportunistic Fungal Infection", Biology of Blood and Marrow Transplantation, Abstracts from the 2014 BMT Tandem Meetings, Feb. 26-Mar. 2, 2014 Grapevine, TX, vol. 20, No. 2, Supplemental 1 (Feb. 2014).
Lanitis et al., Chimeric antigen receptor t cells with dissociated signaling domains exhibit focused antitumor activity with reduced potential for toxicity in vivo, Cancer Immunol. Res., 1:43-53 (2013).
Leonard et al., Phase I/II trial of epratuzumab (humanized anti-CD22 antibody) in indolent non-Hodgkin's lymphoma, J. Clin. Oncol., 21(16):3051-9 (2003).
Likar et al., "The use of the mutated version of human Deoxycytiidinkiase as a reporter gene for the assessment of the adoption of the T-cell therapy," Hematology, Oncology and Immunopathology in Pediatrics 11 (2):23-31 (2012).
Likar et al., Use of Human Deoxycytidine Kinase Mutant Variant as a Reporter Gene for Evaluation of Adoptive T-Cell Therapy, Hematology, Oncology and Immunopathology in Pediatrics, 11(2):24-31 (2012).
Liu et al., "Systematic comparison of 2A peptides for cloning multi-genes in a polycistronic vector", Scientific Reports. 7:2193, pp. 1-9 (May 19, 2017).
Lohmueller, Jason Jakob, "Synthetic Biology Approaches to Engineering Human Cells", Doctoral dissertation, Harvard University (Jan. 2013).
Long et al., "Lessons learned from a highly-active CD22-specific chimeric antigen receptor," OncoImmunoloqy 2:4, 323621, 4 paqes (2013).
Long et al., 4-1 BB costimulation ameliorates T cell exhaustion induced by tonic signaling of chimeric antigen receptors, Nature Med., 21 (6):581-90 (2015).
Mackall et al., "Immune-based therapies for childhood cancer," Nature Reviews, Clinical Oncology 11 :693-703 (2014).
Maeda, et al., "Engineering of Functional Chimeric Protein G-Vargula Luciferase," Analytical Biochemistry 249, Article No. AB972181, pp. 147-152 (1997).
Maher, "Immunotherapy of Malignant Diseases Using Chimeric Antigen Receptor Engrafted T Cells," ISRN Oncoloav, 23 paaes (2012).
Mason et al., Value of monoclonal anti-CD22 (p135) antibodies for the detection of normal and neoplastic B lymphoid cells, Blood, 69(3):836-40 (1987).
Maude et al., "Chimeric antigen receptor T-cell therapy for ALL," Hematology 559-564 (2014).
Maus, et al., "T Cells Expressing Chimeric Antigen Receptors Can Cause Anaphylaxis in Humans," Cancer Immunol Res: 1(1), pp. 26-31 (Jul. 2013).
Meeker et al., A unique human B lymphocyte antigen defined by a monoclonal antibody, Hybridoma, 3(4):305-20 (1984).
Nicholson et al., Construction and characterisation of a functional CD19 specific single chain Fv fragment for immunotherapy of B lineage leukaemia and lymphoma, Mol. Immunol., 34(16-17):1157-65 (1997).
Opponent Comments filed in European Patent Office by Opponent James Poole Ltd. With respect to European Patent No. 3237442, based on European Patent Application No. 15817520.8, communication from EPO dated Apr. 1, 2021.
Opposition Brief filed on behalf of Opponent James Poole Limited against European Patent No. 3237442 (forwarded by the EPO to D. Young on Apr. 17, 2020) (European Patent No. 3237442 is a foreign counterpart to the present application).
Opposition Brief filed on behalf of Opponent Miltenyi Biotec B.V. & Co. KG against European Patent No. 3237442.
Orentas et al., "Immunotherapy targets in pediatric cancer," Frontiers in Oncology 2(3):1-16 (2012).
Pakula et al., "Genetic analysis of protein stability and function," Annual Review Genet. 23:289-310 (1989).
Pegram et al., "CD28z CARs and Armored CARs," Cancer J. 20(2):127-133 (2014).

(56) References Cited

OTHER PUBLICATIONS

Pezzutto et al., Amplification of human B cell activation by a monoclonal antibody to the B cell-specific antiaen CD22, Bp 130/140, J. Immunol., 138(1):98-103 (1987).
Pezzutto et al., CD19 monoclonal antibody HD37 inhibits anti-immunoglobulin-induced B cell activation and proliferation, J. Immunol., 138(9):2793-9 (1987).
Qin et al., "Preclinical Development of Bivalent Chimeric Antigen Receptors Targeting Both CD19 and CD22", Molecular Therapy Oncolytics. vol. 11, pp. 127-137 (Dec. 21, 2018).
Qin et al., Novel CD19/CD22 Bicistronic Chimeric Antigen Receptors outperform single or bivalent cars in eradicating CD19+CD22+, CD19-, and CD22- Pre-B leukemia, Blood. 130:810 (2017).
Qin et al., Preclinical development of bispecific chimeric antigen receptor targeting both CD19 and CD22, Blood. 126:4427 (2015).
Raponi et al., Flow cytometric study of potential target antigens (CD19, CD20, CD22, CD33) for antibody-based immunotherapy in acute lymphoblastic leukemia: analysis of 552 cases, Leuk. Lymphoma, 52(6):1098-107 (2011).
Response of the proprietor to the examination divisional in European Application No. 15817520.8 dated Oct. 16, 2018.
Richman, et al., "High-Affinity GD2-Specific CART Cells Induce Fatal Encephalitis in a Preclinical Neuroblastoma Model," Cancer Immunol Res: 6(1), pp. 36-46 (Jan. 2018).
Riet,, Erhohung der Antigen-Selektivitat von T-Zellen durch Koexpression chimarer Antigen-Rezeptoren unterschiedlicher Spezifitat, PhD thesis, Universitat zu Kain (2010), Enalish abstract.
Rieux-Laucat, et al., "Inherited and Somatic CD3zeta Mutations in a Patient with T-Cell Deficiency," The New England Journal of Medicine, 354(18): 1913-1921 (2006).
Roguska et al., A comparison of two murine monoclonal antibodies humanized by CDR-grafting and variable domain resurfacing, Protein Eng., 9(10):895-904 (1996).
Rossi et al., "Anti-CD22/CD20 Bispecific Antibody with Enhanced Trogocytosis for Treatment of Lupus," PLoS ONE 9(5):1-8 (2014).
Rout, et al., "Cell interaction in the humoral immune response," Immunology, 5th edition, pp. 194-217 (2000) (Mosby, Lindon).
Sadelain et al., "The Basic Principles of Chimeric Antigen Receptor Design," Cancer Discovery 3:388-398 (2013).
Safdari, et al., "Antibody humanization methods—a review and update," Biotechnology and Genetic Engineering Reviews, 29(2):175-86 (2013).
Schamel, et al., "The TCR is an allosterically regulated macromolecular machinery changing its conformation while working," Immunological Reviews; 291:8-25 (2019).
Schwarting et al., The monoclonal antibodies alpha S-HCL 1 (alpha Leu-14) and alpha S-HCL 3 (alpha Leu-M5) allow the diagnosis of hairy cell leukemia, Blood, 65(4):974-83 (1985).
Shi et al., "Chimeric antigen receptor for adoptive immunotherapy of cancer: latest research and future prospects," Molecular Cancer 13:219, 8 pages (2014).
Shih et al., Internalization and intracellular processing of an anti-B-cell lymphoma monoclonal antibody, LL2, Int. J. Cancer, 56(4):538-45 (1994).
Srivastava et al., Engineering CAR-T cells: Design concepts, Trends Immunol., 36(8):494-502 (2015).
Stratagene Catalog, Gene characterization kits, Stratagene Corp., 39 (1988).
Summons to Attend Oral Proceedings issued on Jun. 4, 2021 in corresponding European Application No. 15817520.8 (European Patent No. 3237442)(11 pages), containing preliminary opinion from Opposition Division.
Teplyakov, et al., "Antibody modeling assessment II. Structures of models," Proteins, 82: 1563-1582 (2014).
Tobias Riet: Inaugural doctoral Dissertation, 204 pages, Nov. 24, 2010.
Turtle et al., CD19 CAR-T cells of defined CD4+:CD8+ composition in adult B cell ALL patients, J. Clin. Invest., 126(6):2123-2138 (2016).

Kochenderfer J.N., et al., "Eradication of B-Lineage Cells and Regression of Lymphoma in a Patient Treated with Autologous T Cells Genetically Engineered to Recognize CD19," Blood, 116(20): 4099-4102 (Nov. 2010)., Nov. 18, 2010.
U.S. Appl. No. 17/923,626, filed Nov. 7, 2022, Srivastava et al.
U.S. Appl. No. 18/153,990, filed Jan. 12, 2023, Pulé et al.
U.S. Appl. No. 18/158,310, filed Jan. 23, 2023, Pulé et al.
Apparent email communication involving publication date of [Full Lohmueller Citation] submitted to EPO in opposition proceeding against European Patent No. 3237442, dated Aug. 6, 2021, 2 pages.
Blasi, R. D., et al., A Call for Caution in Analysing Mammalian Co-Transfection Experiments and Implications of Resource Competition in Data Misinterpretation, Nature Communications, 12(2545):1-6 (2021).
Communication of a Notice of Opposition Brief filed on behalf of Opponent Miltenyi Biotec B.V. & Co. KG against European Patent No. 3237442, dated Apr. 15, 2020, 46 pages.
Duong et al., Enhancing the specificity of T-cell cultures for adoptive immunotherapy of cancer, Immunotherapy, 3(1):33-48 (2011).
European Patent Application No. 19172397.2, Office action, dated Feb. 10, 2021, 4 pages.
European Patent Application No. 19172397.2, Office Action, dated Jan. 18, 2022, 4 pages.
European Patent Application No. 19172397.2, Response to Office Action, dated Sep. 15, 2021, 8 pages.
Final Written Submission by Opponent (O2) James Poole Limited against European Patent No. 15817520.8, dated Jan. 28, 2022, 13 pages.
Lee et al., T cells expressing CD19 chimeric antigen receptors for acute lymphoblastic leukaemia in children and young adults: a phase 1 dose-escalation trial, Lancets, 385(9967):517-28 (2015).
Luke G.A., et al., 2A to the Fore—Research, Technology and Applications, Biotechnology and Genetic Engineering Reviews, 26:235-272 (2009).
Maude S.L., et al., CD19-Targeted Chimeric Antigen Receptor T-cell Therapy for Acute Lymphoblastic Leukemia, Blood, 125(26):4017-4023 (2015).
Pfutzner W., "Retroviral Bicistronic Vectors", Drug News Perspect, 21(9):473-480 (2008).
Roitt I., et al., Immunology, Fifth Edition, Mosby London, republished by MIR (Moscow), Chapter 1, pp. 4-6, (2000).
Written Submission in Preparation for the Oral Proceedings by Opponent (O1) Miltenyi Biotec B.V. & Co. KG against European Patent No. 15817520.8, dated Jan. 29, 2022, 30 pages.
Written Submission in Preparation for the Oral Proceedings by Opponent (O2) James Poole Limited against European Patent No. 15817520.8, dated Mar. 11, 2022, 9 pages.
Haso et al., A new high activity anti-CD22 chimeric antigen receptor (CAR) targeting B cell leukemia, Blood, 120(21):2611 (2012).
European Patent Application No. 23217769.1, Extended European Search Report, dated Apr. 30, 2024.
Alvarez-Vallina et al., Antigen-specific targeting of CD28-mediated T cell co-stimulation using chimeric single-chain antibody variable fragment CD28 receptors, Eur. J. Immunol., 26:2304-9 (1996).
Goronzy et al., T-cell co-stimulatory pathways in autoimmunity, Arthritis Res Ther., 10 Suppl 1(Supp 1):S3 (2008).
"Immune Mechanism Laboratory, Chosun University Department of Biology", Molecular Cell Biology News, May 2012, 10 Pages.
Meng et al., Engineering Cystoplasmic Signaling of CD28 CARs for Improved Therapeutic Functions, Frontiers in Immunology, vol. 11, Article 1046 (Jun. 19, 2020).
Kindt et al., "Kuby Immunology", Immunology Textbook, 3 Pages (Aug. 20, 2008).
Wikipedia: "Co-stimulation", Retrieved on Dec. 11, 2024, 11 Pages.
Larson et al., CAR T cell killing requires the IFNgammaR pathway in solid but not liquid tumours, Nature, 31 pages (Apr. 2022).
Boulch et al., Tumor-intrinsic sensitivity to the pro-apoptotic effects of IFN-gamma is a major determinant of CD4+ CAR T-cell anti-tumor activity, Nature Cancer, 4:968-83 (Jul. 2023).
Zibelman et al., A phase 1 study of nivolumab in combination with interferon-gamma for patients with advanced solid tumors, Nature Communications, 14:4513 (2023).

(56) References Cited

OTHER PUBLICATIONS

Boyman et al., The role of interleukin-2 during homeostasis and activation of the immune system, Nat. Rev. Immunol., 12(3):180-90 (2012).

Dummer et al., Phase II clinical trial of intratumoral application of TG1042 (adenovirus-interferon-gamma) in patients with advanced cutaneous T-cell lymphomas and multilesional cutaneous B-cell lymphomas, Mol. Ther., 18(6):1244-7 (2010).

Huppa et al., Continuous T cell receptor signaling required for synapse maintenance and full effector potential, Nat. Immunol., 4(8):749-55 (2003).

Jing et al., Interferon-γ in the tumor microenvironment promotes the expression of B7H4 in colorectal cancer cells, thereby inhibiting cytotoxic T cells, Sci. Rep., 14(1):6053 (Mar. 2024).

Rosenberg et al., Treatment of patients with metastatic melanoma with autologous tumor-infiltrating lymphocytes and interleukin 2, Journal of the National Cancer Institute, 86(15):1159-66 (1994).

Rosenberg et al., Durable complete responses in heavily pretreated patients with metastatic melanoma using T-cell transfer immunotherapy, Clin. Cancer Res., 17(13):4550-7 (2011).

Sarnaik et al., Lifileucel, a Tumor-Infiltrating Lymphocyte Therapy, in Metastatic Melanoma, J. Clin. Oncol., 39(24):2656-66 (2021).

\* cited by examiner

FIG. 4

FIG. 5A
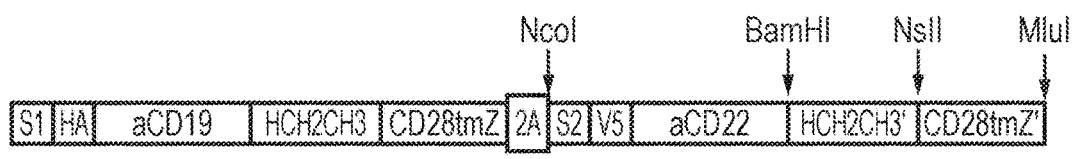
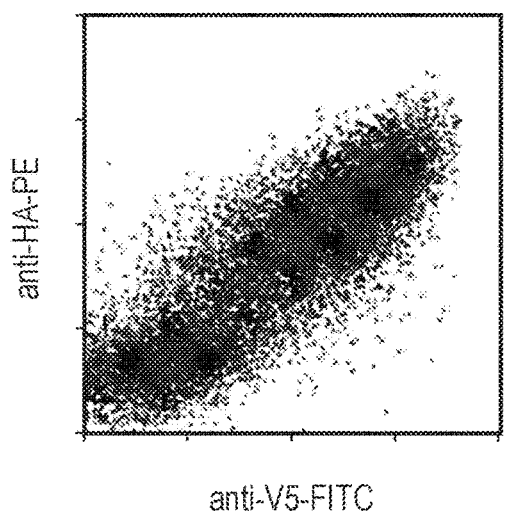
FIG. 5B
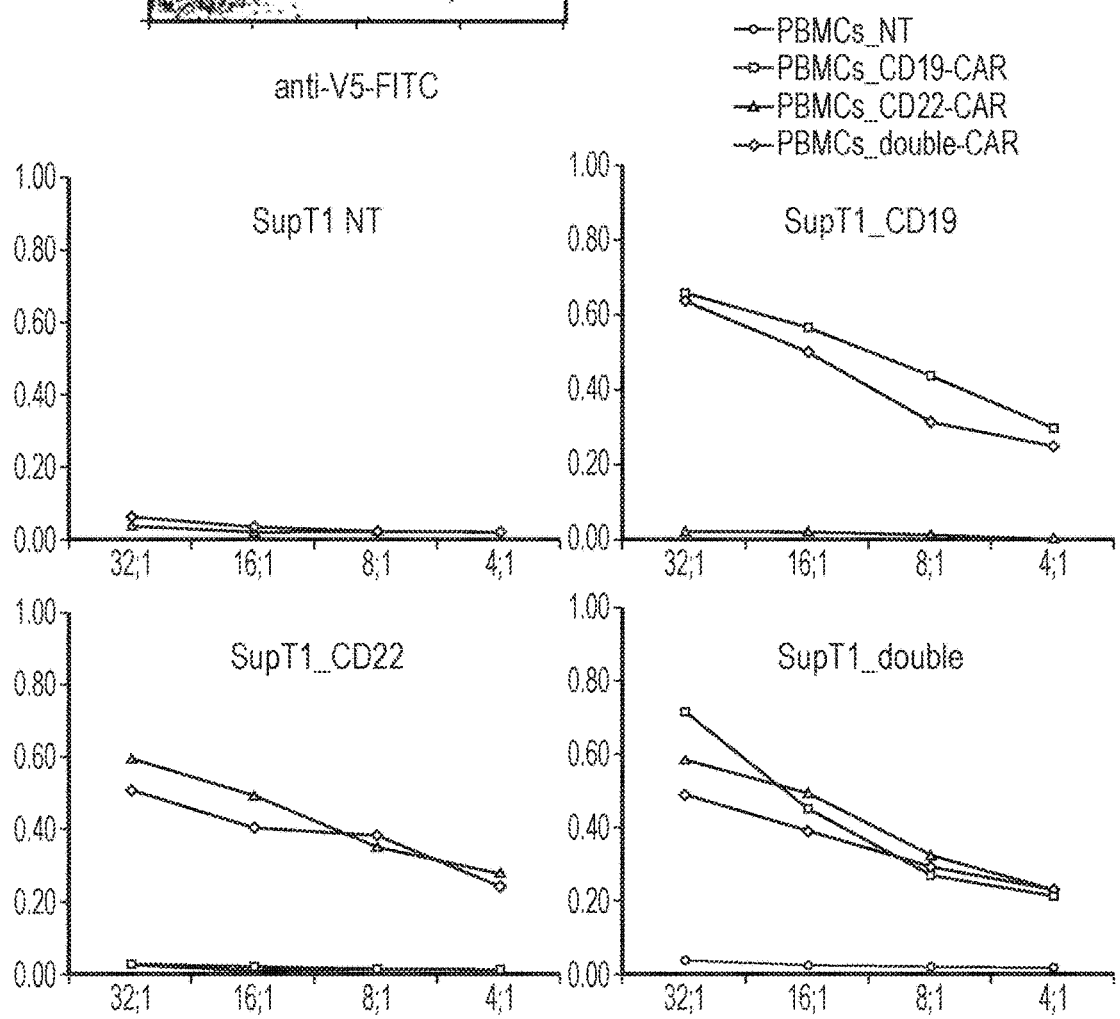
FIG. 5C

| scFv | ka (1/Ms) | kd (1/s) | KD (nM) | n |
|---|---|---|---|---|
| CD19ALAb | $1.65 \pm 0.143 \times 10^5$ | $3.00 \pm 2.198 \times 10^{-4}$ | $1.1 \pm 0.2$ | 2 |
| FMC63 | $3.2 \pm 0.8 \times 10^5$ | $3.9 \pm 1.2 \times 10^{-4}$ | $1.3 \pm 0.7$ | 2 |

FIG. 8

CELL LEXPRESSING TWO CHIMERIC ANTIGEN RECEPTORS (CARs) AT THE CELL SURFACE

CROSS-REFERENCE TO RELATED APPLICATIONS

This Application is a Continuation of U.S. patent application Ser. No. 16/785,467, filed on Feb. 7, 2020; which is a Continuation of U.S. patent application Ser. No. 15/529,690, filed on May 25, 2017 (§ 371(c)); which is a national stage application of International Application No. PCT/GB2015/054137, filed on Dec. 23, 2015; which claims priority under 35 U.S.C. § 119 to United Kingdom Patent Application No. 1423172.4, filed on Dec. 24, 2014.

NAMES OF PARTIES TO A JOINT RESEARCH AGREEMENT

Subject matter disclosed herein was developed by, or on behalf of, parties to a joint research agreement that was in effect on or before the effective filing date of the present application. The parties to the joint research agreement are UCL Business PLC and Autolus Ltd.

INCORPORATION BY REFERENCE OF MATERIAL SUBMITTED ELECTRONICALLY

This application incorporates by reference in its entirety a computer-readable nucleotide/amino acid sequence listing identified as one 71,084 byte file named "52020E_Seqlisting.xml," created on Jan. 20, 2023.

FIELD OF THE INVENTION

The present invention relates to a cell which comprises more than one chimeric antigen receptor (CAR).

BACKGROUND TO THE INVENTION

A number of immunotherapeutic agents have been described for use in cancer treatment, including therapeutic monoclonal antibodies (mAbs), immunoconjugated mAbs, radioconjugated mAbs and bi-specific T-cell engagers.

Typically these immunotherapeutic agents target a single antigen: for instance, Rituximab targets CD20; Myelotarg targets CD33; and Alemtuzumab targets CD52.

The human CD19 antigen is a 95 kd transmembrane glycoprotein belonging to the immunoglobulin superfamily. CD19 is expressed very early in B-cell differentiation and is only lost at terminal B-cell differentiation into plasma cells. Consequently, CD19 is expressed on all B-cell malignancies apart from multiple myeloma. Since loss of the normal B-cell compartment is an acceptable toxicity, CD19 is an attractive CAR target and clinical studies targeting CD19 with CARs have seen promising results.

A particular problem in the field of oncology is provided by the Goldie-Coldman hypothesis: which describes that the sole targeting of a single antigen may result in tumour escape by modulation of said antigen due to the high mutation rate inherent in most cancers. This modulation of antigen expression may reduce the efficacy of known immunotherapeutics, including those which target CD19.

Thus a problem with immunotherapeutics targeted against CD19 is that a B-cell malignancy may mutate and become CD19-negative. This may result in relapse with CD19-negative cancers which are not responsive to CD19 targeted therapeutics. For example, in one paediatric study, Grupp et al. reported that half of all relapses following CD19-targeted chimeric antigen receptor therapy for B-acute Lymphoblastic leukaemia (B-ALL) were due to CD19-negative disease (56th American Society of Hematology Annual Meeting and Exposition).

There is thus a need for immunotherapeutic agents which are capable of targeting more than one cell surface structure to reflect the complex pattern of marker expression that is associated with many cancers, including CD19-positive cancers.

Chimeric Antigen Receptors (CARs)

Chimeric antigen receptors are proteins which graft the specificity of, for example, a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

It has been observed that using a CAR approach for cancer treatment, tumour heterogeneity and immunoediting can cause escape from CAR treatment. For example, in the study described by Grupp et al (2013; New Eng. J. Med 368:1509-1518, paper No 380, ASH 2014) CAR-modified T cell approach was used for the treatment of acute B-lymphocytic leukemia. In that clinical trial it was found that 10 patients with a complete remission after one month did relapse and 5 of them relapsed with CD19-negative disease.

There is thus a need for alternative CAR treatment approaches which address the problems of cancer escape and tumour heterogeneity.

Expression of Two CAR Binding Specificities

Bispecific CARs known as tandem CARs or TanCARs have been developed in an attempt to target multiple cancer specific markers simultaneously. In a TanCAR, the extracellular domain comprises two antigen binding specificities in tandem, joined by a linker. The two binding specificities (scFvs) are thus both linked to a single transmembrane portion: one scFv being juxtaposed to the membrane and the other being in a distal position.

Grada et al (2013, Mol Ther Nucleic Acids 2:e105) describes a TanCAR which includes a CD19-specific scFv, followed by a Gly-Ser linker and then a HER2-specific scFv. The HER2-scFv was in the juxta-membrane position, and the CD19-scFv in the distal position. The Tan CAR was shown to induce distinct T cell reactivity against each of the two tumour restricted antigens. This arrangement was chosen because the respective lengths of HER2 (632 aa/125 Å) and CD19 (280aa, 65 Å) lends itself to that particular spatial arrangement. It was also known that the HER2 scFv bound the distal-most 4 loops of HER2.

The problem with this approach is that the juxta-membrane scFv may be inaccessible due to the presence of the distal scFv, especially which it is bound to the antigen. In view of the need to choose the relative positions of the two scFvs in view of the spatial arrangement of the antigen on the target cell, it may not be possible to use this approach for all scFv binding pairs. Moreover, it is unlikely that the TanCar approach could be used for more than two scFvs, a TanCAR with three or more scFvs would be a very large molecule and the scFvs may well fold back on each other, obscuring the antigen-binding sites. It is also doubtful that antigen-binding by the most distal scFv, which is separated from the transmembrane domain by two or more further scFvs, would be capable of triggering T cell activation.

There is thus a need for an alternative approach to express two CAR binding specificities on the surface of a cell such as a T cell.

SUMMARY OF THE INVENTION

The present inventors have developed a CAR T cell which expresses two CARs at the cell surface, one specific for CD19 and one specific for CD22.

Thus in a first aspect the present invention provides a cell which co-expresses a first chimeric antigen receptor (CAR) and second CAR at the cell surface, each CAR comprising an antigen-binding domain, wherein the antigen-binding domain of the first CAR binds to CD19 and the antigen-binding domain of the second CAR binds to CD22.

The fact the one CAR binds CD19 and the other CAR binds CD22 is advantageous because some lymphomas and leukaemias become CD19 negative after CD19 targeting, (or possibly CD22 negative after CD22 targeting), so it gives a "back-up" antigen, should this occur.

The cell may be an immune effector cell, such as a T-cell or natural killer (NK) cell. Features mentioned herein in connection with a T cell apply equally to other immune effector cells, such as NK cells.

Each CAR may comprise:
(i) an antigen-binding domain;
(ii) a spacer; and
(iii) a trans-membrane domain.

Each CAR may comprise:
(i) an antigen-binding domain;
(ii) a spacer;
(iii) a trans-membrane domain.
(iv) an endodomain.

The spacer of the first CAR may be different to the spacer of the second CAR, such the first and second CAR do not form heterodimers.

The spacer of the first CAR may have a different length and/or configuration from the spacer of the second CAR, such that each CAR is tailored for recognition of its respective target antigen.

The antigen-binding domain of the second CAR may bind to a membrane-distal epitope on CD22. The antigen-binding domain of the second CAR may bind to an epitope on Ig domain 1, 2, 3 or 4 of CD22, for example on Ig domain 3 of CD22.

The antigen-binding domain of the first CAR may bind to an epitope on CD19 which is encoded by exon 1, 3 or 4.

The endodomain of one CAR may comprise a co-stimulatory domain and an ITAM-containing domain; and the endodomain of the other CAR may comprise a TNF receptor family domain and an ITAM-containing domain.

For example, one CAR (which may be CD19 or CD22-specific) may have the structure:
AgB1-spacer1-TM1-costim-ITAM
in which:
AgB1 is the antigen-binding domain;

spacer 1 is the spacer;
TM1 is the transmembrane domain;
costim is a co-stimulatory domain; and
ITAM is an ITAM-containing endodomain;
and the other CAR (which may be CD22 or CD19-specific) may have the structure:
AgB2-spacer2-TM2-TNF-ITAM
in which:
AgB2 is the antigen-binding domain;
spacer 2 is the spacer;
TM2 is the transmembrane domain;
TNF is a TNF receptor endodomain; and
ITAM is an ITAM-containing endodomain.

In a second aspect, the present invention provides, a nucleic acid sequence encoding both the first and second chimeric antigen receptors (CARs) as defined in the first aspect of the invention.

The nucleic acid sequence may have the following structure:
AgB1-spacer1-TM1-coexpr-AbB2-spacer2-TM2
in which
AgB1 is a nucleic acid sequence encoding the antigen-binding domain of the first CAR;
spacer 1 is a nucleic acid sequence encoding the spacer of the first CAR;
TM1 is a a nucleic acid sequence encoding the transmembrane domain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a a nucleic acid sequence encoding the transmembrane domain of the second CAR;
which nucleic acid sequence, when expressed in a T cell, encodes a polypeptide which is cleaved at the cleavage site such that the first and second CARs are co-expressed at the T cell surface.

The nucleic acid sequence may have the following structure:
AgB1-spacer1-TM1-endo1-coexpr-AbB2-spacer2-TM2-endo2
in which
AgB1 is a nucleic acid sequence encoding the antigen-binding domain of the first CAR;
spacer 1 is a nucleic acid sequence encoding the spacer of the first CAR;
TM1 is a a nucleic acid sequence encoding the transmembrane domain of the first CAR;
endo 1 is a nucleic acid sequence encoding the endodomain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a a nucleic acid sequence encoding the transmembrane domain of the second CAR;
endo 2 is a nucleic acid sequence encoding the endodomain of the second CAR;
which nucleic acid sequence, when expressed in a T cell, encodes a polypeptide which is cleaved at the cleavage site such that the first and second CARs are co-expressed at the T cell surface.

The nucleic acid sequence allowing co-expression of two CARs may encode a self-cleaving peptide or a sequence which allows alternative means of co-expressing two CARs such as an internal ribosome entry sequence or a $2^{nd}$ promoter or other such means whereby one skilled in the art can express two proteins from the same vector.

Alternative codons may be used in regions of sequence encoding the same or similar amino acid sequences, such as the transmembrane and/or intracellular T cell signalling domain (endodomain) in order to avoid homologous recombination. For example, alternative codons may be used in the portions of sequence encoding the spacer, the transmembrane domain and/or all or part of the endodomain, such that the two CARs have the same or similar amino acid sequences for this or these part(s) but are encoded by different nucleic acid sequences.

In a third aspect, the present invention provides kit which comprises
- (i) a first nucleic acid sequence encoding the first chimeric antigen receptor (CAR), which nucleic acid sequence has the following structure:
AgB1-spacer1-TM1
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
and
   - (ii) a second nucleic acid sequence encoding the second chimeric antigen receptor, which nucleic acid sequence has the following structure:
AgB2-spacer2-TM2
AgB2 is a nucleic acid sequence encoding the antigen-binding domain of the second CAR;
spacer 2 is a nucleic acid sequence encoding the spacer of the second CAR; and
TM2 is a nucleic acid sequence encoding the transmembrane domain of the second CAR.

The kit may comprise
- (i) a first nucleic acid sequence encoding the first chimeric antigen receptor (CAR), which nucleic acid sequence has the following structure:
AgB1-spacer1-TM1-endo1
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
endo 1 is a nucleic acid sequence encoding the endodomain of the first CAR; and
   - (ii) a second nucleic acid sequence encoding the second chimeric antigen receptor (CAR), which nucleic acid sequence has the following structure:
AgB2-spacer2-TM2-endo2
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR; endo 2 is a nucleic acid sequence encoding the endodomain of the second CAR.

In a fourth aspect, the present invention provides a kit comprising: a first vector which comprises the first nucleic acid sequence; and a second vector which comprises the second nucleic acid sequence.

The vectors may be plasmid vectors, retroviral vectors or transposon vectors. The vectors may be lentiviral vectors.

In a fifth aspect, the present invention provides a vector comprising a nucleic acid sequence according to the second aspect of the invention. The vector may be a lentiviral vector.

The vector may be a plasmid vector, a retroviral vector or a transposon vector.

In a sixth aspect the present invention provides a method for making a cell according to the first aspect of the invention, which comprises the step of introducing one or more nucleic acid sequence(s) encoding the first and second CARs; or one or more vector(s), as defined above, into a T cell.

The cell may be from a sample isolated from a patient, a related or unrelated haematopoietic transplant donor, a completely unconnected donor, from cord blood, differentiated from an embryonic cell line, differentiated from an inducible progenitor cell line, or derived from a transformed cell line.

In a seventh aspect, the present invention provides a pharmaceutical composition comprising a plurality of cells according to the first aspect of the invention.

In an eighth aspect the present invention provides a method for treating and/or preventing a disease, which comprises the step of administering a pharmaceutical composition according to the seventh aspect of the invention to a subject.

The method may comprise the following steps:
- (i) isolation of a cell-containing sample from a subject;
- (ii) transduction or transfection of the cells with one or more nucleic acid sequence(s) encoding the first and second CAR or one or more vector(s) comprising such nucleic acid sequence(s); and
- (iii) administering the cells from (ii) to a the subject.

The disease may be cancer. The cancer may be a B cell malignancy.

In a ninth aspect the present invention provides a pharmaceutical composition according to the seventh aspect of the invention for use in treating and/or preventing a disease.

In a tenth aspect the present invention provides the use of a cell according to the first aspect of the invention in the manufacture of a medicament for treating and/or preventing a disease.

The present invention also provides a nucleic acid sequence which comprises:
- a) a first nucleotide sequence encoding a first chimeric antigen receptor (CAR);
- b) a second nucleotide sequence encoding a second CAR; wherein one CAR binds CD19 and the other CAR binds CD22; and
- c) a sequence encoding a self-cleaving peptide positioned between the first and second nucleotide sequences, such that the two CARs are expressed as separate entities.

Alternative codons may be used in one or more portion(s) of the first and second nucleotide sequences in regions which encode the same or similar amino acid sequence(s).

The present invention also provides a vector and a cell comprising such a nucleic acid.

The present inventors have also developed new anti-CD19 and anti-CD22 CARs with improved properties.

Thus in an eleventh aspect, the present invention provides a chimeric antigen receptor (CAR) comprising a CD19-binding domain which comprises
  a) a heavy chain variable region (VH) having complementarity determining regions (CDRs) with the following sequences:

```
CDR1
                                    (SEQ ID NO. 15)
SYWMN;

CDR2
                                    (SEQ ID NO. 16)
QIWPGDGDTNYNGKFK

CDR3
                                    (SEQ ID NO. 17)
RETTTVGRYYYAMDY;
``` and
  b) a light chain variable region (VL) having CDRs with the following sequences:

```
CDR1
                                    (SEQ ID NO. 18)
KASQSVDYDGDSYLN;

CDR2
                                    (SEQ ID NO. 19)
DASNLVS

CDR3
                                    (SEQ ID NO. 20)
QQSTEDPWT.
```

The CD19 binding domain may comprise a VH domain having the sequence shown as SEQ ID NO: 23, or SEQ ID NO: 24; or a VL domain having the sequence shown as SEQ ID NO: 25, SEQ ID NO: 26 or SEQ ID NO: 40 or a variant thereof having at least 90% sequence identity which retains the capacity to bind CD19.

The CD19 binding domain may comprise the sequence shown as SEQ ID NO: 21, SEQ ID NO: 22 or SEQ ID NO: 39 or a variant thereof having at least 90% sequence identity which retains the capacity to bind CD19.

In a twelfth aspect the present invention provides a chimeric antigen receptor (CAR) comprising a CD22-binding domain which comprises
  a) a heavy chain variable region (VH) having complementarity determining regions (CDRs) with the following sequences:

```
CDR1
                                    (SEQ ID NO. 27)
NYWIN;

CDR2
                                    (SEQ ID NO. 28)
NIYPSDSFTNYNQKFKD

CDR3
                                    (SEQ ID NO. 29)
DTQERSWYFDV;
``` and
  b) a light chain variable region (VL) having CDRs with the following sequences:

```
CDR1
                                    (SEQ ID NO. 30)
RSSQSLVHSNGNTYLH;

CDR2
                                    (SEQ ID NO. 31)
KVSNRFS

CDR3
                                    (SEQ ID NO. 32)
SQSTHVPWT.
```

The CD22 binding domain may comprise a VH domain having the sequence shown as SEQ ID NO: 35, or SEQ ID NO: 36; or a VL domain having the sequence shown as SEQ ID NO: 37, or SEQ ID NO: 38 or a variant thereof having at least 90% sequence identity which retains the capacity to bind CD22.

The CD22 binding domain may comprise the sequence shown as SEQ ID NO: 33 or SEQ ID NO: 34 or a variant thereof having at least 90% sequence identity which retains the capacity to bind CD22.

In a thirteenth aspect there is provided a cell which expresses a chimeric antigen receptor according to the eleventh aspect of the invention or a chimeric antigen receptor according to the twelfth aspect of the invention at the cell surface.

In a fourteenth aspect, there is provided a nucleic acid sequence encoding a chimeric antigen receptor according to the eleventh aspect of the invention or a chimeric antigen receptor according to the twelfth aspect of the invention.

In a fifteenth aspect, the present invention provides a vector comprising a nucleic acid sequence according to the fourteenth aspect of the invention. The vector may be a lentiviral vector.

The vector may be a plasmid vector, a retroviral vector or a transposon vector.

In a sixteenth aspect, the present invention provides a method for making a cell according to the thirteenth aspect of the invention, which comprises the step of introducing one or more nucleic acid sequence(s); or one or more vector(s), as defined above, into a cell.

The cell may be a T-cell or a natural killer (NK) cell. The cell may be from a sample isolated from a patient, a related or unrelated haematopoietic transplant donor, a completely unconnected donor, from cord blood, differentiated from an embryonic cell line, differentiated from an inducible progenitor cell line, or derived from a transformed cell line.

In a seventeenth aspect, the present invention provides a pharmaceutical composition comprising a plurality of cells according to the thirteenth aspect of the invention.

In an eighteenth aspect the present invention provides a method for treating and/or preventing a disease, which comprises the step of administering a pharmaceutical composition according to the seventeenth aspect of the invention to a subject.

The method may comprise the following steps:
  (i) isolation of a cell-containing sample from a subject;
  (ii) transduction or transfection of the cells with a nucleic acid sequence encoding the CAR or a vector comprising such a nucleic acid sequence; and
  (iii) administering the cells from (ii) to a the subject.

The disease may be cancer. The cancer may be a B cell malignancy.

In a ninteenth aspect the present invention provides a pharmaceutical composition according to the seventeenth aspect of the invention for use in treating and/or preventing a disease.

In a twentieth aspect the present invention provides the use of a cell according to the thirteenth aspect of the invention in the manufacture of a medicament for treating and/or preventing a disease.

There is also provided a cell according to the first aspect of the invention, which comprises a first CAR as defined in the eleventh aspect of the invention and a second CAR as defined in the twelfth aspect of the invention.

There is also provided a nucleic acid sequence according to the second aspect of the invention, encoding a first CAR as defined in the eleventh aspect of the invention and a second CAR as defined in the twelfth aspect of the invention.

There is also provided a kit according to the third aspect of the invention, wherein the first nucleic acid sequence encodes a first CAR as defined in the eleventh aspect of the invention and the second nucleic acid sequence encodes a second CAR as defined in the twelfth aspect of the invention.

There is also provided a vector according to the fifth aspect of the invention, which comprises a nucleic acid sequence encoding a first CAR as defined in the eleventh aspect of the invention and a second CAR as defined in the twelfth aspect of the invention.

The present inventors have also found that, in an OR gate system, performance is improved if the co-stimulatory domain and domain producing survival signals are "split" between the two (or more) CARs.

Thus, in a twenty-first aspect there is provided a cell which co-expresses a first chimeric antigen receptor (CAR) and second CAR at the cell surface, each CAR comprising an intracellular signalling domain, wherein the intracellular signalling domain of the first CAR comprises a co-stimulatory domain; and the intracellular signalling domain of the second CAR comprises a TNF receptor family endodomain.

The co-stimulatory domain may be a CD28 co-stimulatory domain.

The TNF receptor family endodomain may be, for example OX-40 or 4-1 BB endodomain.

The intracellular signalling domain of the first and the second CAR may also comprise an ITAM-containing domain, such as a CD3 zeta endodomain.

The first CAR may have the structure:
AgB1-spacer1-TM1-costim-ITAM
in which:
AgB1 is the antigen-binding domain of the first CAR;
spacer 1 is the spacer of the first CAR;
TM1 is the transmembrane domain of the first CAR;
costim is a co-stimulatory domain; and
ITAM is an ITAM-containing endodomain.

The second CAR may have the structure:
AgB2-spacer2-TM2-TNF-ITAM
in which:
AgB2 is the antigen-binding domain of the second CAR;
spacer 2 is the spacer of the second CAR;
TM2 is the transmembrane domain of the second CAR;
TNF is a TNF receptor endodomain; and
ITAM is an ITAM-containing endodomain.

One CAR out of the first and second CAR may target CD19 and the other CAR may target CD22.

In a twenty-second aspect there is provided a nucleic acid sequence encoding both the first and second chimeric antigen receptors (CARs) as defined in the twenty-first aspect of the invention.

The nucleic acid sequence may have the following structure:
AgB1-spacer1-TM1-costim-ITAM1-coexpr-AbB2-spacer2-TM2-TNF-ITAM2
in which
AgB1 is a nucleic acid sequence encoding the antigen-binding domain of the first CAR;
spacer 1 is a nucleic acid sequence encoding the spacer of the first CAR;
TM1 is a a nucleic acid sequence encoding the transmembrane domain of the first CAR;
costim is a nucleic acid sequence encoding a co-stimulatory domain;
ITAM1 is a nucleic acid sequence encoding the ITAM-containing endodomain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
TNF is a nucleic acid sequence encoding a TNF receptor endodomain;
ITAM2 is a nucleic acid sequence encoding the ITAM-containing endodomain of the second CAR.

When the nucleic acid sequence is expressed in a cell it may encode a polypeptide which is cleaved at the cleavage site such that the first and second CARs are co-expressed at the cell surface.

In a twenty-third aspect, there is provided a kit which comprises
(i) a first nucleic acid sequence encoding the first chimeric antigen receptor (CAR) as defined in the twenty-first aspect of the invention, which nucleic acid sequence has the following structure:
AgB1-spacer1-TM1-costim-ITAM1
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
costim is a nucleic acid sequence encoding a co-stimulatory domain;
ITAM1 is a nucleic acid sequence encoding the ITAM-containing endodomain of the first CAR;
and
(ii) a second nucleic acid sequence encoding the second chimeric antigen receptor (CAR) as defined in the twenty-first aspect of the invention, which nucleic acid sequence has the following structure:
AbB2-spacer2-TM2-TNF-ITAM2
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
TNF is a nucleic acid sequence encoding a TNF receptor endodomain; and
ITAM2 is a nucleic acid sequence encoding the ITAM-containing endodomain of the second CAR.

In a twenty-fourth aspect there is provided a vector comprising a nucleic acid sequence according to the twenty-second aspect of the invention or as defined in the twenty-third aspect of the invention.

In a twenty-fifth aspect, there is provided a method for making a cell according to the twenty-first aspect of the invention, which comprises the step of introducing: a nucleic acid sequence according to twenty-second aspect of the invention; a first nucleic acid sequence and a second nucleic acid sequence as defined in the twenty-third aspect of the invention; or a vector according to the twenty-fourth aspect of the invention, into a cell.

In a twenty-sixth aspect, the present invention provides a pharmaceutical composition comprising a plurality of cells according to the twenty-first aspect of the invention.

There is also provided a method for treating and/or preventing a disease, which comprises the step of administering a pharmaceutical composition according to the twenty-sixth aspect of the invention to a subject.

There is also provided a pharmaceutical composition according to the twenty-sixth aspect of the invention for use in treating and/or preventing a disease.

There is also provided the use of a cell according to the twenty-first aspect of the invention in the manufacture of a medicament for treating and/or preventing a disease.

By providing one CAR which targets CD19 and one CAR which targets CD22, it is possible to target each of these markers, thereby reducing the problem of cancer escape.

Because the CARs are expressed on the surface of the cell as separate molecules, this approach overcomes the spatial and accessibility issues associated with TanCARs. Cell activation efficiency is also improved. If each CAR has its own spacer, it is possible to tailor the spacer domain and therefore the distance that the binding domain projects from the cell surface and its flexibility etc. to the particular target antigen. This choice is unfettered by the design considerations associated with TanCARs, i.e. that one CAR needs to be juxtaposed to the T cell membrane and one CAR needs to be distal, positioned in tandem to the first CAR.

By providing a single nucleic acid which encodes the two CARs separated by a cleavage site, it is possible to engineer cells to co-express the two CARs using a simple single transduction procedure. A double transfection procedure could be used with CAR-encoding sequences in separate constructs, but this would be more complex and expensive and requires more integration sites for the nucleic acids. A double transfection procedure would also be associated with uncertainty as to whether both CAR-encoding nucleic acids had been transduced and expressed effectively.

The CARs will have portions of high homology, for example the transmembrane and/or intracellular signalling domains are likely to be highly homologous. If the same or similar linkers are used for the two CARs, then they will also be highly homologous. This would suggest that an approach where both CARs are provided on a single nucleic acid sequence would be inappropriate, because of the likelihood of homologous recombination between the sequences. However, the present inventors have found that by "codon wobbling" the portions of sequence encoding areas of high homology, it is possible to express two CARs from a single construct with high efficiency. Codon wobbling involves using alternative codons in regions of sequence encoding the same or similar amino acid sequences.

DESCRIPTION OF THE FIGURES

FIG. 1A) Schematic diagram illustrating a classical CAR. FIGS. 1B-1D: Different generations and permutations of CAR endodomains: (FIG. 1B) initial designs transmitted ITAM signals alone through FcεR1-γ or CD3ζ endodomain, while later designs transmitted additional (FIG. 1C) one or (FIG. 1D) two co-stimulatory signals in the same compound endodomain.

(FIG. 3A) an OR gate cassette is constructed so that both CARs are co-expressed using a FMD-2A peptide. Any homologous sequences are codon-wobbled to avoid recombination. (FIG. 3B) The two CARs are co-expressed as separate proteins on the T-cell surface.

FIG. 4: Example of codon-wobbling to allow co-expression in a retroviral vector of identical peptide sequences but avoiding homologous recombination. Here, wild-type HCH2CH3-CD28tmZeta (SEQ ID NO: 48) is aligned with codon-wobbled HCH2CH3-CD28tmZeta (SEQ ID NO: 49).

FIGS. 5A-5C: Demonstrating functionality of anti-CD19 OR CD22 CAR gate. (FIG. 5A) Cartoon of construct: S1—signal peptide 1; HA—haemagglutin tag; HCH2CH3—hinge, CH2CH3 of IgG1 wild-type sequence; CD28tmZ—CD28 transmembrane domain and CD3 Zeta wobbled sequence; 2A—Foot and mouth disease 2A peptide; S2—signal peptide 2; V5-v5 epitope tag; aCD22—anti-CD22 scFv; HCH2CH3'—hinge, CH2CH3 of IgG1 wobbled sequence; CD28tmZ—CD28 transmembrane domain and CD3 Zeta wobbled sequence. (FIG. 5B) Co-expression of two receptors from a single vector. Peripheral blood T-cells were transduced with bicistronic vector after stimulation with OKT3 and anti-CD28. Cells were analysed five days after transduction by staining with anti-V5-FITC (Invitrogen) and anti-HA-PE (abCam). The two CARs can be detected simultaneously on the T-cell surface. (FIG. 5C) Non-transduced T-cells, T-cells expressing just anti-CD19 CAR, T-cells expressing just anti-CD22 CAR and T-cells expressing the anti-CD19 OR CD22 CAR gate were challenged with target cells expressing neither CD19 or CD22, either CD19 or CD22 singly, or both antigen. T-cells expressing the anti-CD19 OR CD22 CAR gate could kill target cells even if one antigen was absent.

FIG. 8: Comparison of the binding kinetics between soluble scFv-CD19 binding for CD19ALAb scFv and fmc63 scFv.

FIG. 11A) Killing assay of CD22 positive target cells comparing a CAR with a CD22ALAb antigen binding domain and an equivalent CAR with an M971 binding domain. FIG. 11B) Assay comparing IFNγ release following co-culture 1:1 with CD22 positive SupT1 cells.

FIG. 13A: CD19 and CD22 CAR both have 41BB-CD3zeta compound endodomains; FIG. 13B: CD19 and CD22 CAR both have OX40-CD3zeta compound endodomains; FIG. 13C: CD19 CAR has 41 BB-CD3zeta compound endodomain and CD22 CAR has CD28-CD3zeta compound endodomain; and FIG. 13D: CD19 CAR has OX40-CD3zeta compound endodomain and CD22 CAR has CD28-CD3zeta compound endodomain.

DETAILED DESCRIPTION

Chimeric Antigen Receptors (Cars)

Figure 1:
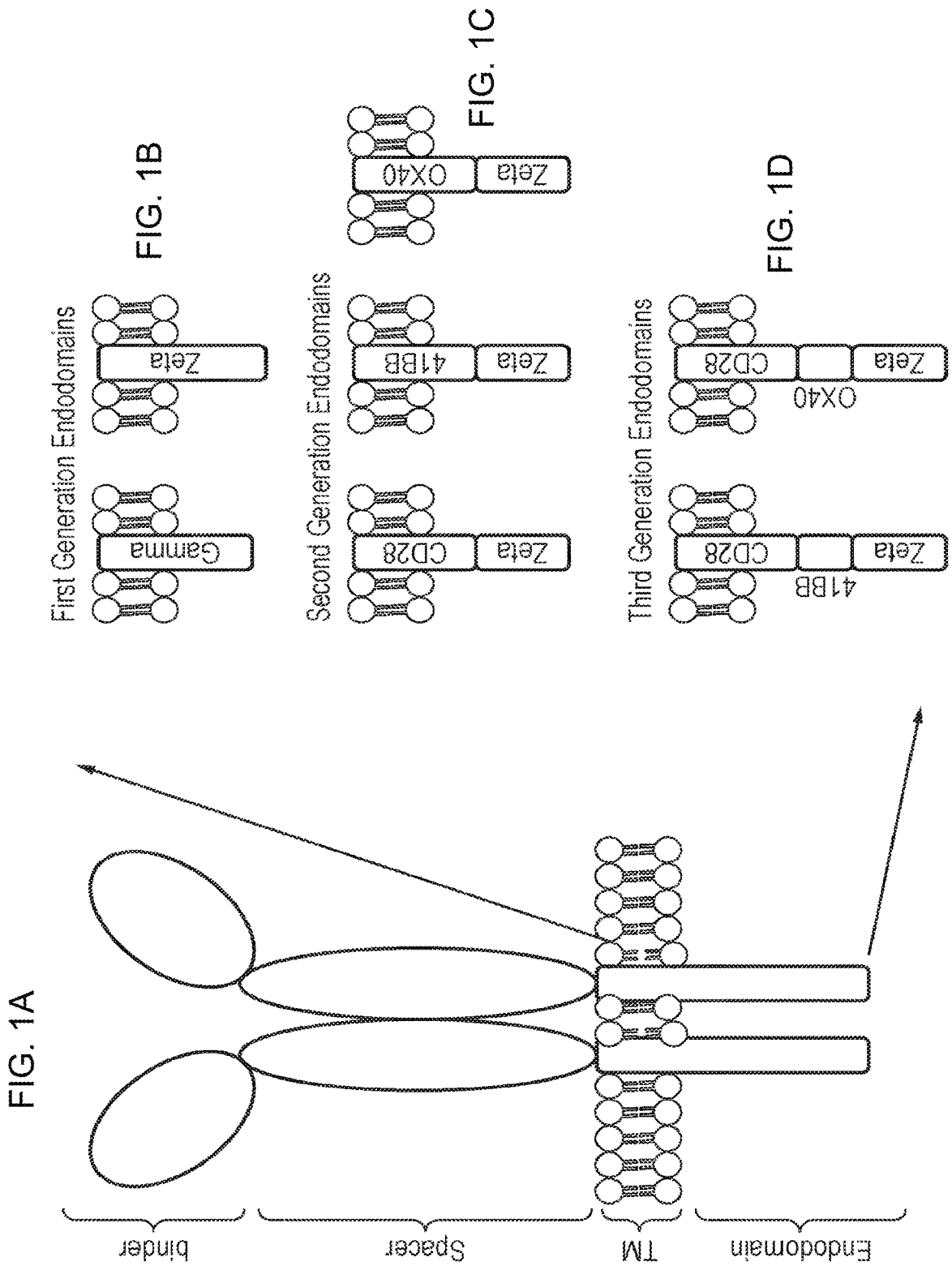
FIGS. 1A-1D.

CARs, which are shown schematically in FIGS. 1A-1D, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

The first aspect of the invention relates to a cell which co-expresses a first CAR and a second CAR, wherein one CAR binds CD19 and the other CAR binds CD22, such that a T-cell can recognize a target cells expressing either of these markers.

Thus, the antigen binding domains of the first and second CARs of the present invention bind to different antigens and both CARs may comprise an activating endodomain. The two CARs may comprise spacer domains which may be the same, or sufficiently different to prevent cross-pairing of the two different receptors. A cell can hence be engineered to activate upon recognition of either or both CD19 and CD22. This is useful in the field of oncology as indicated by the Goldie-Coldman hypothesis: sole targeting of a single antigen may result in tumour escape by modulation of said antigen due to the high mutation rate inherent in most cancers. By simultaneously targeting two antigens, the probably of such escape is exponentially reduced.

It is important that the two CARs do not heterodimerize.

The first and second CAR of the T cell of the present invention may be produced as a polypeptide comprising both CARs, together with a cleavage site.

Signal Peptide

The CARs of the cell of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID NO: 1, 2 or 3 or a variant thereof having 5, 4, 3, 2 or 1 amino acid mutations (insertions, substitutions or additions) provided that the signal peptide still functions to cause cell surface expression of the CAR.

```
SEQ ID NO. 1:
MGTSLLCWMALCLLGADHADG
```

The signal peptide of SEQ ID NO: 1 is compact and highly efficient. It is predicted to give about 95% cleavage after the terminal glycine, giving efficient removal by signal peptidase.

```
SEQ ID NO. 2:
MSLPVTALLLPLALLLHAARP
```

The signal peptide of SEQ ID NO: 2 is derived from IgG1.

```
SEQ ID NO. 3:
MAVPTQVLGLLLLWLTDARC
```

The signal peptide of SEQ ID NO: 3 is derived from CD8.

The signal peptide for the first CAR may have a different sequence from the signal peptide of the second CAR.

CD19

Figure 12:
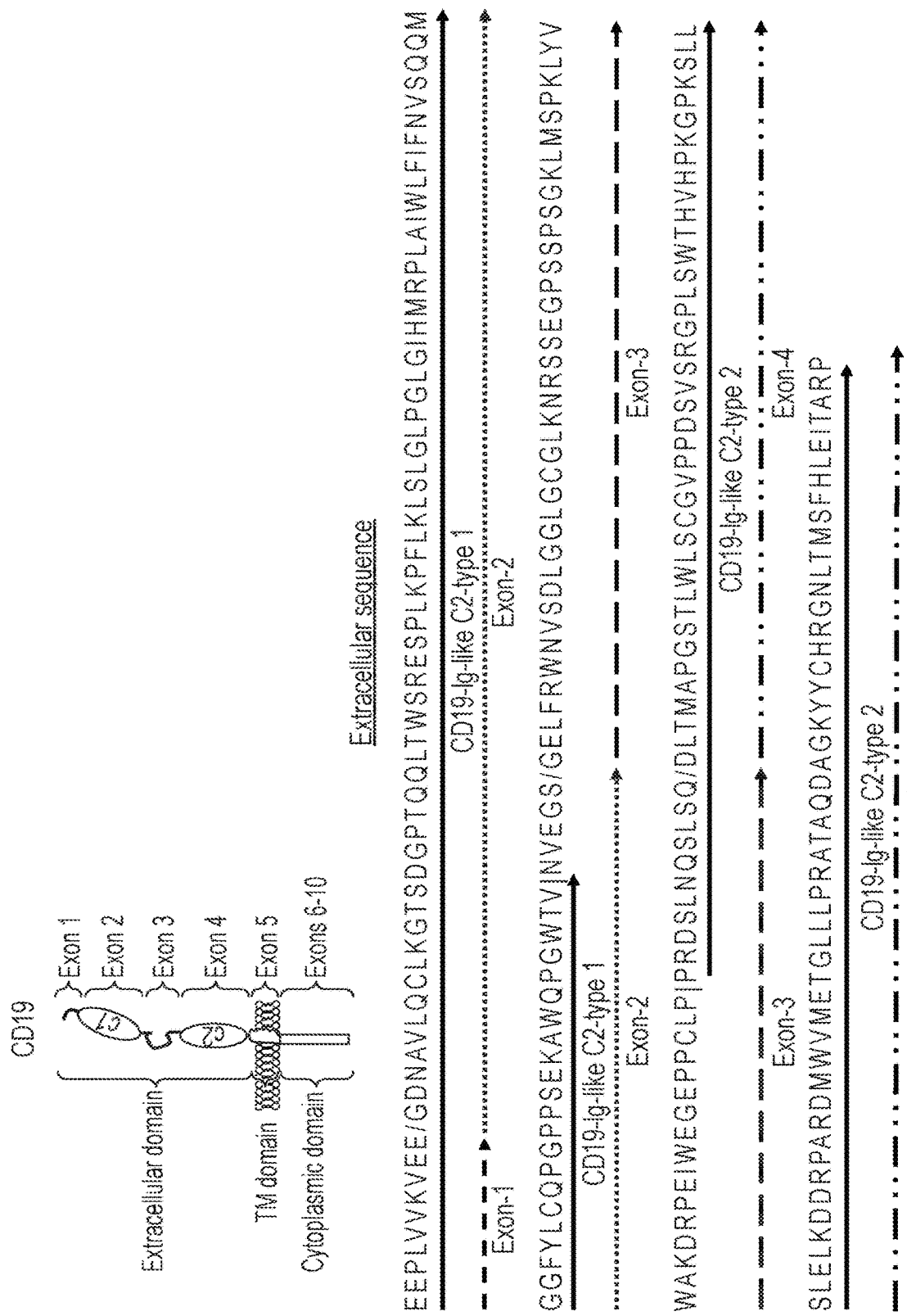
FIG. 12: CD19 structure and exons (SEQ ID NO: 46).
Figure 13A:
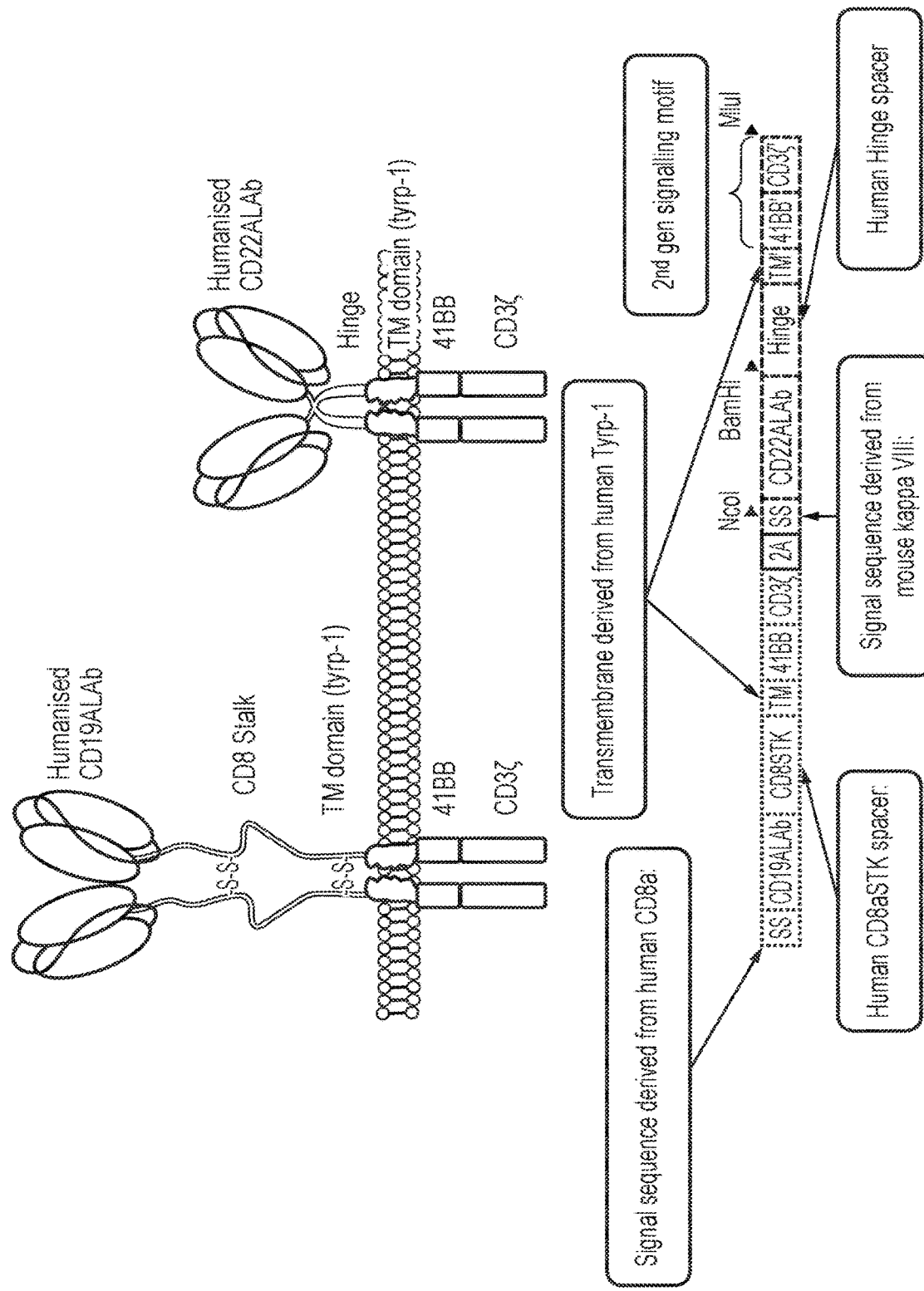
FIGS. 13A-13D: Schematic diagrams and construct maps illustrating the four constructs tested in Example 5. In the construct map, portions marked with ' are codon-wobbled.
Figure 13B:
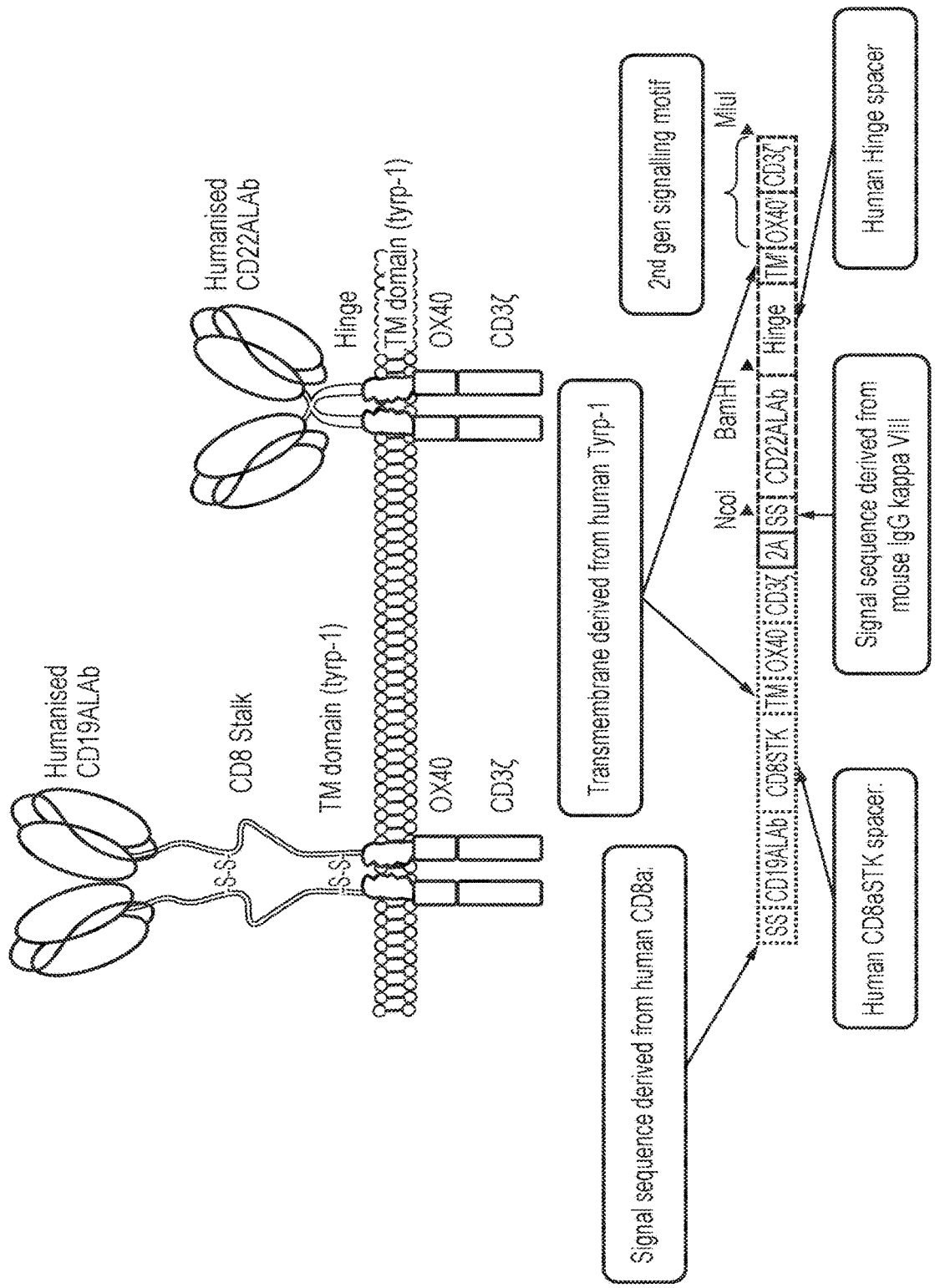
Figure 13C:
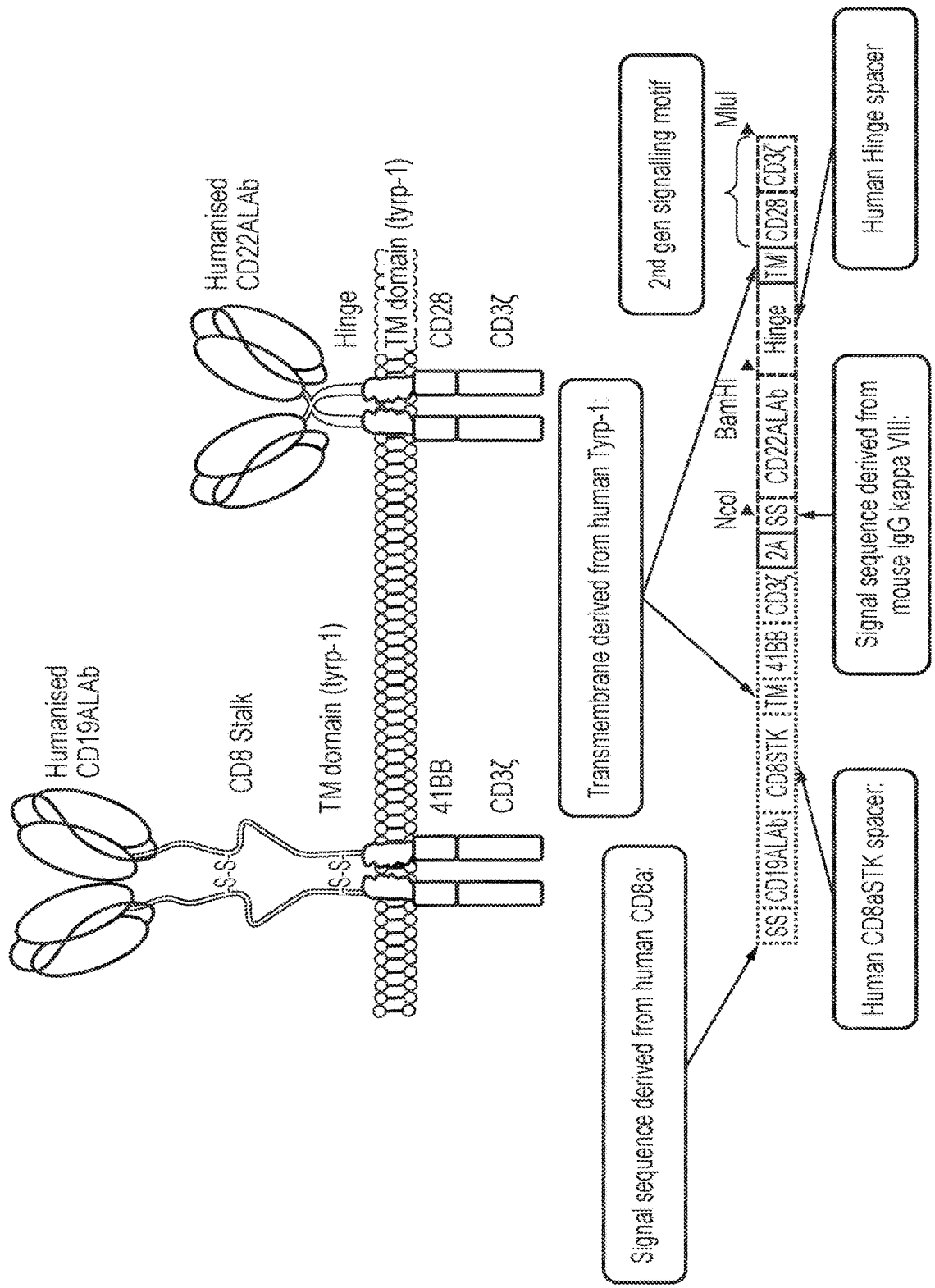
Figure 13D:
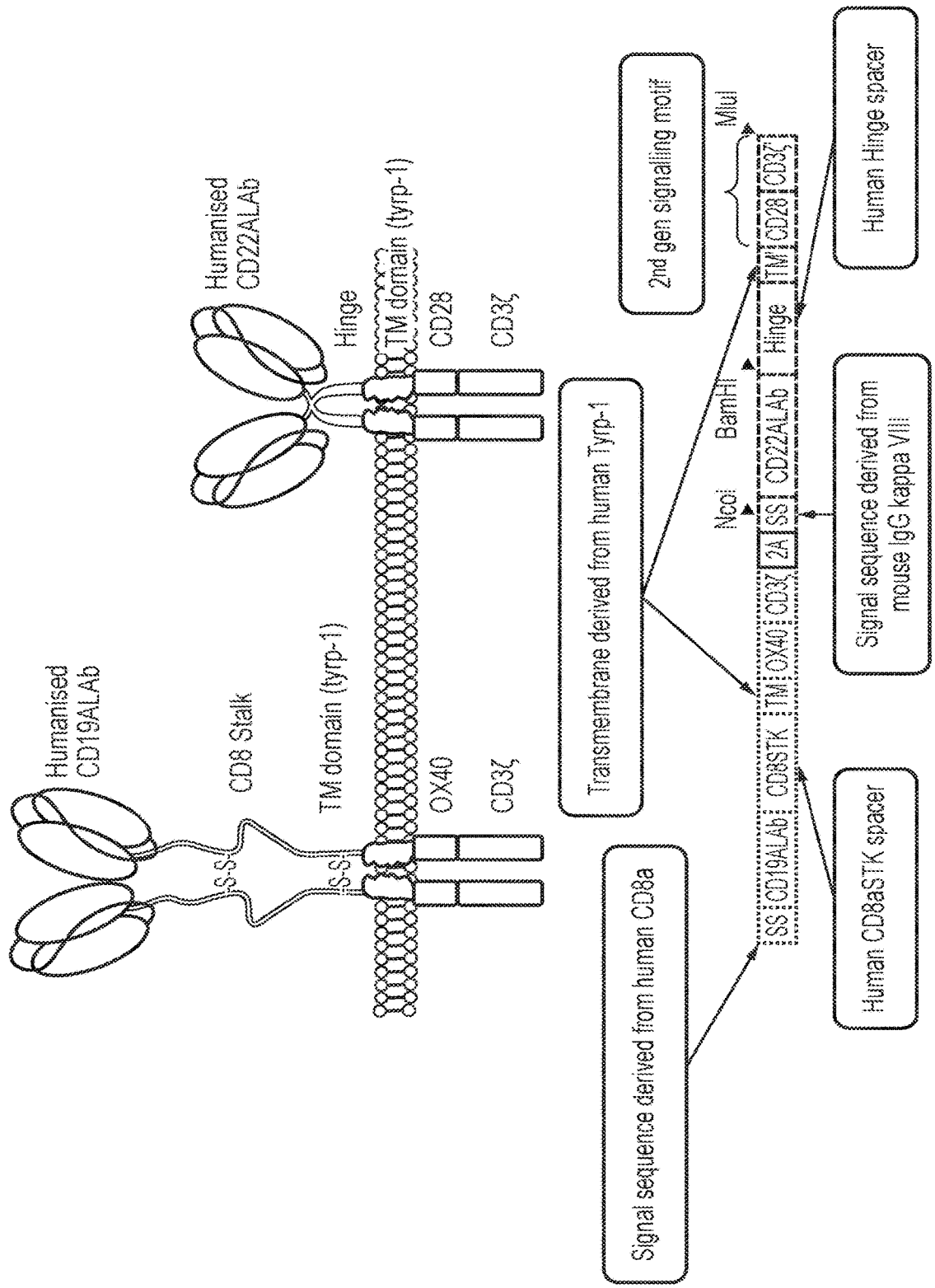

The human CD19 antigen is a 95 kd transmembrane glycoprotein belonging to the immunoglobulin superfamily. CD19 is classified as a type I transmembrane protein, with a single transmembrane domain, a cytoplasmic C-terminus, and extracellular N-terminus. The general structure for CD19 is illustrated in FIG. 12.

CD19 is a biomarker for normal and neoplastic B cells, as well as follicular dendritic cells. In fact, it is present on B cells from earliest recognizable B-lineage cells during development to B-cell blasts but is lost on maturation to plasma cells. It primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. CD19 is expressed very early in B-cell differentiation and is only lost at terminal B-cell differentiation into plasma cells. Consequently, CD19 is expressed on all B-cell malignancies apart from multiple myeloma.

Different designs of CARs have been tested against CD19 in different centres, as outlined in the following Table:

TABLE 1

| Centre | Binder | Endodomain | Comment |
|---|---|---|---|
| University College London | Fmc63 | CD3-Zeta | Low-level brief persistence |
| Memorial Sloane Kettering | SJ25C1 | CD28-Zeta | Short-term persistence |
| NCI/KITE | Fmc63 | CD28-Zeta | Long-term low-level persistence |
| Baylor, Centre for Cell and Gene Therapy | Fmc63 | CD3-Zeta/ CD28-Zeta | Short-term low-level persistence |
| UPENN/Novartis | Fmc63 | 41BB-Zeta | Long-term high-level persistence |

As shown above, most of the studies conducted to date have used an scFv derived from the hybridoma fmc63 as part of the binding domain to recognize CD19.

As shown in FIG. 12, the gene encoding CD19 comprises ten exons: exons 1 to 4 encode the extracellular domain; exon 5 encodes the transmembrane domain; and exons 6 to 10 encode the cytoplasmic domain, In the CD19/CD22 OR gate of the present invention, the antigen-binding domain of the anti-CD19 CAR may bind an epitope of CD19 encoded by exon 1 of the CD19 gene.

In the CD19/CD22 OR gate of the present invention, the antigen-binding domain of the anti-CD19 CAR may bind an epitope of CD19 encoded by exon 3 of the CD19 gene.

In the CD19/CD22 OR gate of the present invention, the antigen-binding domain of the anti-CD19 CAR may bind an epitope of CD19 encoded by exon 4 of the CD19 gene.

CD19ALAb

The present inventors have developed a new anti-CD19 CAR which has improved properties compared to a known anti-CD19 CAR which comprises the binder fmc63 (see Examples 2 and 3). The antigen binding domain of the CAR is based on the CD19 binder CD19ALAb, which has the CDRs and VH/VL regions identified below.

The present invention therefore also provides a CAR which comprises a CD19-binding domain which comprises a) a heavy chain variable region (VH) having complementarity determining regions (CDRs) with the following sequences:

CDR1
(SEQ ID NO. 15)
SYWMN;

CDR2
(SEQ ID NO. 16)
QIWPGDGDTNYNGKFK

CDR3
(SEQ ID NO. 17)
RETTTVGRYYYAMDY;

and
b) a light chain variable region (VL) having CDRs with the following sequences:

CDR1
(SEQ ID NO. 18)
KASQSVDYDGDSYLN;

CDR2
(SEQ ID NO. 19)
DASNLVS

CDR3
(SEQ ID NO. 20)
QQSTEDPWT.

It may be possible to introduce one or more mutations (substitutions, additions or deletions) into the or each CDR without negatively affecting CD19-binding activity. Each CDR may, for example, have one, two or three amino acid mutations.

The CAR of the present invention may comprise one of the following amino acid sequences:

(Murine CD19ALAb scFv sequence)
SEQ ID NO. 21
QVQLQQSGAELVRPGSSVKISCKASGYAFSSYWMNWVKQRPGQGLEWIG

QIWPGDGDTNYNGKFKGKATLTADESSSTAYMQLSSLASEDSAVYFCAR

RETTTVGRYYYAMDYWGQGTTVTVSSDIQLTQSPASLAVSLGQRATISC

KASQSVDYDGDSYLNWYQQIPGQPPKLLIYDASNLVSGIPPRFSGSGSG

TDFTLNIHPVEKVDAATYHCQQSTEDPWTFGGGTKLEIK (Humanised CD19ALAb scFv sequence-Heavy 19,
Kappa 16)
SEQ ID NO. 22
QVQLVQSGAEVKKPGASVKLSCKASGYAFSSYWMNWVRQAPGQSLEWIG

QIWPGDGDTNYNGKFKGRATLTADESARTAYMELSSLRSGDTAVYFCAR

RETTTVGRYYYAMDYWGKGTLVTVSSDIQLTQSPDSLAVSLGERATINC

KASQSVDYDGDSYLNWYQQKPGQPPKLLIYDASNLVSGVPDRFSGSGSG

TDFTLTISSLQAADVAVYHCQQSTEDPWTFGQGTKVEIKR (Humanised CD19ALAb scFv sequence-
Heavy 19, Kappa 7)
SEQ ID NO. 39
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSSDIQLTQSPDSLAVSLGERATINCKAS

QSVDYDGDSYLNWYQQKPGQPPKVLIYDASNLVSGVPDRFSGSGSGTDFT

LTISSLQAADVAVYYCQQSTEDPWTFGQGTKVEIKR

The scFv may be in a VH-VL orientation (as shown in SEQ ID NO:s 21, 22 and 39) or a VL-VH orientation.

The CAR of the present invention may comprise one of the following VH sequences:

(Murine CD19ALAb VH sequence)
SEQ ID NO. 23
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSS (Humanised CD19ALAb VH sequence)
SEQ ID NO. 24
QVQLVQSGAEVKKPGASVKLSCKASGYAFSSYWMNWVRQAPGQSLEWIGQ

IWPGDGDTNYNGKFKGRATLTADESARTAYMELSSLRSGDTAVYFCARRE

TTTVGRYYYAMDYWGKGTLVTVSS

The CAR of the present invention may comprise one of the following VL sequences:

```
(Murine CD19ALAb VL sequence)
                                    SEQ ID NO. 25
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIK (Humanised CD19ALAb VL sequence, Kappa 16)
                                    SEQ ID NO. 26
DIQLTQSPDSLAVSLGERATINCKASQSVDYDGDSYLNWYQQKPGQPPKL

LIYDASNLVSGVPDRFSGSGSGTDFTLTISSLQAADVAVYHCQQSTEDPW

TFGQGTKVEIKR (Humanised CD19ALAb VL sequence, Kappa 7)
                                    SEQ ID NO. 40
DIQLTQSPDSLAVSLGERATINCKASQSVDYDGDSYLNWYQQKPGQPPKV

LIYDASNLVSGVPDRFSGSGSGTDFTLTISSLQAADVAVYYCQQSTEDPW

TFGQGTKVEIKR
```

The CAR of the invention may comprise a variant of the sequence shown as SEQ ID NO: 21, 22, 23, 24, 25, 26, 39 or 40 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at http://blast.ncbi.nlm.nih.gov.

CD22

The human CD22 antigen is a molecule belonging to the SIGLEC family of lectins. It is found on the surface of mature B cells and on some immature B cells. Generally speaking, CD22 is a regulatory molecule that prevents the overactivation of the immune system and the development of autoimmune diseases.

CD22 is a sugar binding transmembrane protein, which specifically binds sialic acid with an immunoglobulin (Ig) domain located at its N-terminus. The presence of Ig domains makes CD22 a member of the immunoglobulin superfamily. CD22 functions as an inhibitory receptor for B cell receptor (BCR) signaling.

CD22 is a molecule of the IgSF which may exist in two isoforms, one with seven domains and an intra-cytoplasmic tail comprising of three ITIMs (immune receptor tyrosine-based inhibitory motifs) and an ITAM; and a splicing variant which instead comprises of five extracellular domains and an intra-cytoplasmic tail carrying one ITIM. CD22 is thought to be an inhibitory receptor involved in the control of B-cell responses to antigen. Like CD19, CD22 is widely considered to be a pan-B antigen, although expression on some non-lymphoid tissue has been described. Targeting of CD22 with therapeutic monoclonal antibodies and immunoconjugates has entered clinical testing.

Examples of anti-CD22 CARs are described by Haso et al. (Blood; 2013; 121(7)). Specifically, anti-CD22 CARs with antigen-binding domains derived from m971, HA22 and BL22 scFvs are described.

The antigen-binding domain of the anti-CD22 CAR may bind CD22 with a $K_D$ in the range 30-50 nM, for example 30-40 nM. The $K_D$ may be about 32 nM.

CD-22 has seven extracellular IgG-like domains, which are commonly identified as Ig domain 1 to Ig domain 7, with Ig domain 7 being most proximal to the B cell membrane and Ig domain 7 being the most distal from the Ig cell membrane (see Haso et al 2013 as above FIG. 2B).

The positions of the Ig domains in terms of the amino acid sequence of CD22 (http COLON-SLASH-SLASH www DOT uniprot.org/uniprot/P20273) are summarised in the following table:

| Ig domain | Amino acids |
| --- | --- |
| 1 | 20-138 |
| 2 | 143-235 |
| 3 | 242-326 |
| 4 | 331-416 |
| 5 | 419-500 |
| 6 | 505-582 |
| 7 | 593-676 |

The antigen-binding domain of the second CAR may bind to a membrane-distal epitope on CD22. The antigen-binding domain of the second CAR may bind to an epitope on Ig domain 1, 2, 3 or 4 of CD22, for example on Ig domain 3 of CD22. The antigen-binding domain of the second CAR may bind to an epitope located between amino acids 20-416 of CD22, for example between amino acids 242-326 of CD22.

The anti-CD22 antibodies HA22 and BL22 (Haso et al 2013 as above) and CD22ALAb, described below, bind to an epitope on Ig domain 3 of CD22.

The antigen binding domain of the second CAR may not bind to a membrane-proximal epitope on CD22. The antigen-binding domain of the second CAR may not bind to an epitope on Ig domain 5, 6 or 7 of CD22. The antigen-binding domain of the second CAR may not bind to an epitope located between amino acids 419-676 of CD22, such as between 505-676 of CD22.

CD22ALAb

The present inventors have developed a new anti-CD22 CAR which has improved properties compared to a known anti-CD22 CAR which comprises the binder m971 (see Examples 2 and 3 and Haso et al (2013) as above). The antigen binding domain of the CAR is based on the CD22 binder CD22ALAb, which has the CDRs and VH/VL regions identified below.

The present invention therefore also provides a CAR which comprises a CD22-binding domain which comprises a) a heavy chain variable region (VH) having complementarity determining regions (CDRs) with the following sequences:

```
CDR1
                                    (SEQ ID NO. 27)
NYWIN;

CDR2
                                    (SEQ ID NO. 28)
NIYPSDSFTNYNQKFKD

CDR3
                                    (SEQ ID NO. 29)
DTQERSWYFDV;
``` and b) a light chain variable region (VL) having CDRs with the following sequences:

CDR1

(SEQ ID NO. 30)
RSSQSLVHSNGNTYLH;

CDR2

(SEQ ID NO. 31)
KVSNRFS

CDR3

(SEQ ID NO. 32)
SQSTHVPWT.

It may be possible to introduce one or more mutations (substitutions, additions or deletions) into the or each CDR without negatively affecting CD22-binding activity. Each CDR may, for example, have one, two or three amino acid mutations.

The CAR of the present invention may comprise one of the following amino acid sequences:

(Murine CD22ALAb scFv sequence)

SEQ ID NO. 33
QVQLQQPGAELVRPGASVKLSCKASGYTFTNYWINWVKQRPGQGLEWIGN

IYPSDSFTNYNQKFKDKATLTVDKSSSTAYMQLSSPTSEDSAVYYCTRDT

QERSWYFDVWGAGTTVTVSSDVVMTQTPLSLPVSLGDQASISCRSSQSLV

HSNGNTYLHWYLQKPGQSPKLLIYKVSNRFSGVPDRFSGSGSGTDFTLKI

SRVEAEDLGLYFCSQSTHVPWTFGGGTKLEIK (Humanised CD22ALAb scFv sequence)

SEQ ID NO. 34
EVQLVESGAEVKKPGSSVKVSCKASGYTFTNYWINWVRQAPGQGLEWIGN

IYPSDSFTNYNQKFKDRATLTVDKSTSTAYLELRNLRSDDTAVYYCTRDT

QERSWYFDVWGQGTLVTVSSDIVMTQSPATLSVSPGERATLSCRSSQSLV

HSNGNTYLHWYQQKPGQAPRLLIYKVSNRFSGVPARFSGSGSGVEFTLTI

SSLQSEDFAVYYCSQSTHVPWTFGQGTRLEIK

The scFv may be in a VH-VL orientation (as shown in SEQ ID NOs: 33 and 34) or a VL-VH orientation.

The CAR of the present invention may comprise one of the following VH sequences:

(Murine CD22ALAb VH sequence)

SEQ ID NO. 35
QVQLQQPGAELVRPGASVKLSCKASGYTFTNYWINWVKQRPGQGLEWIGN

IYPSDSFTNYNQKFKDKATLTVDKSSSTAYMQLSSPTSEDSAVYYCTRDT

QERSWYFDVWGAGTTVTVSS (Humanised CD22ALAb VH sequence)

SEQ ID NO. 36
EVQLVESGAEVKKPGSSVKVSCKASGYTFTNYWINWVRQAPGQGLEWIGN

IYPSDSFTNYNQKFKDRATLTVDKSTSTAYLELRNLRSDDTAVYYCTRDT

QERSWYFDVWGQGTLVTVSS

The CAR of the present invention may comprise one of the following VL sequences:

(Murine CD22ALAb VL sequence)

SEQ ID NO. 37
DVVMTQTPLSLPVSLGDQASISCRSSQSLVHSNGNTYLHWYLQKPGQSPK

LLIYKVSNRFSGVPDRFSGSGSGTDFTLKISRVEAEDLGLYFCSQSTHVP

WTFGGGTKLEIK (Humanised CD22ALAb VL sequence)

SEQ ID NO. 38
DIVMTQSPATLSVSPGERATLSCRSSQSLVHSNGNTYLHWYQQKPGQAPR

LLIYKVSNRFSGVPARFSGSGSGVEFTLTISSLQSEDFAVYYCSQSTHVP

WTFGQGTRLEIK

The CAR of the invention may comprise a variant of the sequence shown as SEQ ID NO: 33, 34, 35, 36, 37 or 38 having at least 80, 85, 90, 95, 98 or 99% sequence identity, provided that the variant sequence retain the capacity to bind CD22 (when in conjunction with a complementary VL or VH domain, if appropriate).

B-Cell Antigen Expression During B-Cell Ontogeny and Subsequent Tumours

CD19 is widely considered a pan-B antigen, although very occasionally, it may display some lineage infidelity. The CD19 molecule comprises of two extracellular IgSF domains separated by a smaller domain and a long intracytoplasmic tail, nearly as big as the extracellular portion of the molecule, carrying one ITAM. CD19 is a key molecule in the development and activation of B-cells. CD22 is a molecule of the IgSF which may exist in two isoforms, one with seven domains and an intra-cytoplasmic tail comprising of three ITIMs (immune receptor tyrosine-based inhibitory motifs) and an ITAM; and a splicing variant which instead comprises of five extracellular domains and an intra-cytoplasmic tail carrying one ITIM. CD22 is thought to be an inhibitory receptor involved in the control of B-cell responses to antigen. Like CD19, CD22 is widely considered to be a pan-B antigen, although expression on some non-lymphoid tissue has been described (Wen et al. (2012) J. Immunol. Baltim. Md 1950 188, 1075-1082). Targeting of CD22 with therapeutic monoclonal antibodies and immunoconjugates has entered clinical testing. Generation of CD22 specific CARs have been described (Haso et al, 2013, Blood: Volume 121; 7: 1165-74, and James et al 2008, Journal of immunology, Volume 180; Issue 10; Pages 7028-38).

Detailed immunophentyping studies of B-cell leukaemias shows that while surface CD19 is always present, surface CD22 is almost always present. For instance, Raponi et al (2011, as above) studied the surface antigen phenotype of 427 cases of B-ALL and found CD22 present in 341 of cases studied.

The eventuality of CD19 down-regulation after CAR19 targeting described above may be explained by the Goldie-Coldman hypothesis. The Goldie-Coldman hypothesis predicts that tumor cells mutate to a resistant phenotype at a rate dependent on their intrinsic genetic instability and that the probability that a cancer would contain resistant clones depends on the mutation rate and the size of the tumor. While it may be difficult for cancer cells to become intrinsically resistant to the direct killing of cytotoxic T-cells, antigen loss remains possible. Indeed this phenomenon has been reported before with targeting melanoma antigens and EBV-driven lymphomas. According to Goldie-Coldman hypothesis, the best chance of cure would be to simultaneously attack non-cross resistant targets. Given that CD22 is expressed on nearly all cases of B-ALL, simultaneous CAR targeting of CD19 along with CD22 may reduce the emergence of resistant CD19 negative clones.

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain of the CAR which binds to CD19 may be any domain which is capable of binding CD19. For example, the antigen binding domain may comprise a CD19 binder as described in Table 1.

The antigen binding domain of the CAR which binds to CD19 may comprise a sequence derived from one of the CD19 binders shown in Table 2.

TABLE 2

| Binder | References |
| --- | --- |
| HD63 | Pezzutto (Pezzutto, A. et al. J. Immunol. Baltim. Md 1950 138, 2793-2799 (1987) |
| 4g7 | Meeker et al (Meeker, T. C. et al. Hybridoma 3, 305-320 (1984) |
| Fmc63 | Nicholson et al (Nicholson, I. C. et al. Mol. Immunol. 34, 1157-1165 (1997) |
| B43 | Bejcek et al (Bejcek, B. E. et al. Cancer Res. 55, 2346-2351 (1995) |
| SJ25C1 | Bejcek et al (1995, as above) |
| BLY3 | Bejcek et al (1995, as above) |
| B4, or re-surfaced, or humanized B4 | Roguska et al (Roguska, M. A. et al. Protein Eng. 9, 895-904 (1996) |
| HB12b, optimized and humanized | Kansas et al (Kansas, G. S. & Tedder, T. F. J. Immunol. Baltim. Md 1950 147, 4094-4102 (1991); Yazawa et al (Yazawa et al Proc. Natl. Acad. Sci. U.S.A. 102, 15178-15183 (2005); Herbst et al (Herbst, R. et al. J. Pharmacol. Exp. Ther. 335, 213-222 (2010) |

The antigen binding domain of the CAR which binds to CD22 may be any domain which is capable of binding CD22. For example, the antigen binding domain may comprise a CD22 binder as described in Table 3.

TABLE 3

| Binder | References |
| --- | --- |
| M5/44 or humanized M5/44 | John et al (J. Immunol. Baltim. Md 1950 170, 3534-3543 (2003); and DiJoseph et al (Cancer Immunol. Immunother. CII 54, 11-24 (2005) |
| M6/13 | DiJoseph et al (as above) |
| HD39 | Dorken et al (J. Immunol. Baltim. Md 1950 135, 4470-4479 (1986) |
| HD239 | Dorken et al (as above) |
| HD6 | Pezzutto et al (J. Immunol. Baltim. Md 1950 138, 98-103 (1987) |
| RFB-4, or humanized RFB-4, or affinity matured | Campana et al (J. Immunol. Baltim. Md 1950 134,1524-1530 (1985); Krauss et al (Protein Eng. 16, 753-759 (2003), Kreitman et al (J. Clin. Oncol. Off. J. Am. Soc. Clin. Oncol. 30, 1822-1828 (2012)) |
| To15 | Mason et al (Blood 69, 836-840 (1987)) |
| 4KB128 | Mason et al (as above) |
| S-HCL1 | Schwarting et al (Blood 65, 974-983 (1985)) |
| mLL2 (EPB-2), or humanized mLL2-hLL2 | Shih et al (Int. J. Cancer J. Int. Cancer 56, 538-545 (1994)), Leonard et al (J. Clin. Oncol. Off. J. Am. Soc. Clin. Oncol. 21, 3051-3059 (2003)) |
| M971 | Xiao et al (mAbs 1, 297-303 (2009)) |
| BC-8 | Engel et al (J. Exp. Med. 181, 1581-1586 (1995)) |
| HB22-12 | Engel et al (as above) |

Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In the cell of the present invention, the first and second CARs may comprise different spacer molecules. For example, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

The spacer for the anti-CD19 CAR may comprise a CD8 stalk spacer, or a spacer having a length equivalent to a CD8 stalk spacer. The spacer for the anti-CD19 CAR may have at least 30 amino acids or at least 40 amino acids. It may have between 35-55 amino acids, for example between 40-50 amino acids. It may have about 46 amino acids.

The spacer for the anti-CD22 CAR may comprise an IgG1 hinge spacer, or a spacer having a length equivalent to an IgG1 hinge spacer. The spacer for the anti-CD22 CAR may have fewer than 30 amino acids or fewer than 25 amino acids. It may have between 15-25 amino acids, for example between 18-22 amino acids. It may have about 20 amino acids.

Examples of amino acid sequences for these spacers are given below:

```
SEQ ID NO. 4 (hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL
```

```
-continued
TCLVKGFYPSDIAVEWESNGQPENNYKTTPPVLDSDGSFFLYSKLTVDKS

RWQQGNVFSCSVMHEALHNHYTQKSLSLSPGKKD

SEQ ID NO. 5 (human CD8 stalk):
TTTPAPRPPTPAPTIASQPLSLRPEACRPAAGGAVHTRGLDFACDI

SEQ ID NO. 6 (human IgG1 hinge):
AEPKSPDKTHTCPPCPKDPK

SEQ ID NO. 7 (CD2 ectodomain)
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD

SEQ ID NO. 8 (CD34 ectodomain)
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT
```

Since CARs are typically homodimers (see FIG. 1A), cross-pairing may result in a heterodimeric chimeric antigen receptor. This is undesirable for various reasons, for example: (1) the epitope may not be at the same "level" on the target cell so that a cross-paired CAR may only be able to bind to one antigen; (2) the VH and VL from the two different scFv could swap over and either fail to recognize target or worse recognize an unexpected and unpredicted antigen. The spacer of the first CAR may be sufficiently different from the spacer of the second CAR in order to avoid cross-pairing. The amino acid sequence of the first spacer may share less than 50%, 40%, 30% or 20% identity at the amino acid level with the second spacer.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http COLON-SLASH-SLASH www DOT cbs.dtu.dk/services/TMHMM-2.0/). Further, given that the transmembrane domain of a protein is a relatively simple structure, i.e., a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good receptor stability.

The transmembrane domain may be derived from human Tyrp-1. The tyrp-1 transmembrane sequence is shown as SEQ ID NO: 45.

```
                                          SEQ ID NO. 45
IIAIAVVGALLLVALIFGTASYLI
```

Activating Endodomain

The endodomain is the signal-transmission portion of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The cell of the present invention comprises two CARs, each with an endodomain.

The endodomain of the first CAR and the endodomain of the second CAR may comprise:

(i) an ITAM-containing endodomain, such as the endodomain from CD3 zeta;

and/or (ii) a co-stimulatory domain, such as the endodomain from CD28; and/or (iii) a domain which transmits a survival signal, for example a TNF receptor family endodomain such as OX-40 or 4-1 BB.

In one arrangement the co-stimulatory and survival signal-producing domains are "shared" between the two (or more) CARs in an OR gate. For example, where an OR gate has two CARs, CAR A and CAR B, CAR A may comprise a co-stimulatory domain (e.g. CD28 endodomain) and CAR B may comprise a TNF receptor family endodomain, such as OX-40 or 4-1 BB.

An endodomain which contains an ITAM motif can act as an activation endodomain in this invention. Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I. Typically, but not always, two of these motifs are separated by between 6 and 8 amino acids in the tail of the molecule (YxxL/Ix (6-8)YxxL/I). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000/063372, which relates to synthetic signalling molecules).

The transmembrane and intracellular T-cell signalling domain (endodomain) of a CAR with an activating endodomain may comprise the sequence shown as SEQ ID NO: 9, 10 or 11 or a variant thereof having at least 80% sequence identity.

```
comprising CD28 transmembrane domain and CD3 Z
endodomain
                                           SEQ ID NO. 9
FWVLVVVGGVLACYSLLVTVAFIIFWVRRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR
```

-continued comprising CD28 transmembrane domain and CD28 and
CD3 Zeta endodomains

SEQ ID NO. 10
FWVLVVVGGVLACYSLLVTVAFIIFWVRSKRSRLLHSDYMNMTPRRPGPT

RKHYQPYAPPRDFAAYRSRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR comprising CD28 transmembrane domain and CD28, OX40
and CD3 Zeta endodomains

SEQ ID NO. 11
FWVLVVVGGVLACYSLLVTVAFIIFWVRSKRSRLLHSDYMNMTPRRPGPT

RKHYQPYAPPRDFAAYRSRDQRLPPDAHKPPGGGSFRTPIQEEQADAHST

LAKIRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR.

A variant sequence may have at least 80%, 85%, 90%, 95%, 98% or 99% sequence identity to SEQ ID NO: 9, 10 or 11, provided that the sequence provides an effective trans-membrane domain and an effective intracellular T cell signaling domain.

"Split" or Gate Endodomains

The present invention provides an OR gate in which the co-stimulatory/survival signal domains are "split" between the two CARs.

In this respect, the present invention provides a cell which co-expresses a first chimeric antigen receptor (CAR) and second CAR at the cell surface, each CAR comprising an intracellular signalling domain, wherein the intracellular signalling domain of the first CAR comprises a co-stimulatory domain; and the intracellular signalling domain of the second CAR comprises a TNF receptor family endodomain.

The first and second CARs may bind to different antigens. For example, the first CAR may bind CD19 and the second CAR may bind CD22; alternatively the first CAR may bind CD22 and the second CAR may bind CD19.

The intracellular signalling domain of the first CAR comprises a co-stimulatory domain and does not comprise a domain which transmits survival signals (such as a TNF receptor family endodomain). The intracellular signalling domain of the second CAR comprises a TNF receptor family endodomain and does not comprise a co-stimulatory domain (such as CD28 endodomain).

The co-stimulatory domain may be a CD28 co-stimulatory domain. The CD28 co-stimulatory domain may have the sequence shown as SEQ ID NO: 41.

(CD28 co-stimulatory endodomain)

SEQ ID NO. 41
SKRSRLLHSDYMNMTPRRPGPTRKHYQPYAPPRDFAAYRS

The CAR of the invention may comprise a variant of the sequence shown as SEQ ID NO: 41 having at least 80, 85, 90, 95, 98 or 99% sequence identity, provided that the variant sequence retains the capacity to co-stimulate T cells upon antigen recognition, i.e. provide signal 2 to T cells.

The TNF receptor family endodomain may be an OX40 or 4-1 BB endodomain. The OX40 endodomain may have the sequence shown as SEQ ID NO: 42. The 4-1BB endodomain may have the sequence shown as SEQ ID NO: 43.

(OX40 endodomain)

SEQ ID NO. 42
RDQRLPPDAHKPPGGGSFRTPIQEEQADAHSTLAKI (4-1BB endodomain)

SEQ ID NO. 43
KRGRKKLLYIFKQPFMRPVQTTQEEDGCSCRFPEEEEGGCEL

The CAR of the invention may comprise a variant of the sequence shown as SEQ ID NO: 42 or 43 having at least 80, 85, 90, 95, 98 or 99% sequence identity, provided that the variant sequence retains the capacity to transmit a survival signal to T cells upon antigen recognition.

The intracellular signalling domain of the first and/or the second CAR may also comprise an ITAM-containing domain, such as a CD3 zeta domain. The CD3 zeta domain may have the sequence shown as SEQ ID NO: 44.

(CD3zeta endodomain)

SEQ ID NO. 44
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

The CAR of the invention may comprise a variant of the sequence shown as SEQ ID NO: 44 having at least 80, 85, 90, 95, 98 or 99% sequence identity, provided that the variant sequence retains the capacity to induce T-cell signalling upon antigen recognition, i.e. provide signal 1 to T cells.

The first CAR may have the structure:

AgB1-spacer1-TM1-costim-ITAM in which:

AgB1 is the antigen-binding domain of the first CAR;
spacer 1 is the spacer of the first CAR;
TM1 is the transmembrane domain of the first CAR;
costim is a co-stimulatory domain; and
ITAM is an ITAM-containing endodomain.

"Costim" may be a CD28 co-stimulatory domain.

"ITAM" may be a CD3 zeta endodomain.

The second CAR may have the structure:

AgB2-spacer2-TM2-TNF-ITAM in which:

AgB2 is the antigen-binding domain of the second CAR;
spacer 2 is the spacer of the second CAR;
TM2 is the transmembrane domain of the second CAR;
TNF is a TNF receptor endodomain; and
ITAM is an ITAM-containing endodomain.

"TNF" may be a TNF receptor endodomain such as the OX40 or 4-1 BB endodomains.

There is also provided a nucleic acid sequence encoding both the first and second chimeric antigen receptors (CARs) with "split" endodomains; and a kit comprising two nucleic acids one encoding a first CAR and one encoding a second CAR comprising split endodomains as defined above.

Co-Expression Site

The second aspect of the invention relates to a nucleic acid which encodes the first and second CARs.

The nucleic acid may produce a polypeptide which comprises the two CAR molecules joined by a cleavage site. The cleavage site may be self-cleaving, such that when the polypeptide is produced, it is immediately cleaved into the first and second CARs without the need for any external cleavage activity.

Various self-cleaving sites are known, including the Foot-and-Mouth disease virus (FMDV) 2A peptide and similar sequence (Donnelly et al, Journal of General Virology (2001), 82, 1027-1041), for instance like the 2A-like sequence from Thosea asigna virus which has the sequence shown as SEQ ID NO: 12:

```
                                    SEQ ID NO. 12
        RAEGRGSLLTCGDVEENPGP.
```

The co-expressing sequence may be an internal ribosome entry sequence (IRES). The co-expressing sequence may be an internal promoter Cell The present invention relates to a cell which co-expresses a first CAR and a second CAR at the cell surface, wherein one CAR binds CD19 and the other CAR binds CD22.

The cell may be any eukaryotic cell capable of expressing a CAR at the cell surface, such as an immunological cell.

In particular the cell may be an immune effector cell such as a T cell or a natural killer (NK) cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The T cell of the invention may be any of the T cell types mentioned above, in particular a CTL.

Natural killer (NK) cells are a type of cytolytic cell which forms part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

CAR—expressing cells, such as CAR-expressing T or NK cells may either be created ex vivo either from a patient's own peripheral blood (1st party), or in the setting of a haematopoietic stem cell transplant from donor peripheral blood (2nd party), or peripheral blood from an unconnected donor (3rd party).

The present invention also provide a cell composition comprising CAR expressing T cells and/or CAR expressing NK cells according to the present invention. The cell composition may be made by transducing a blood-sample ex vivo with a nucleic acid according to the present invention.

Alternatively, CAR-expressing cells may be derived from ex vivo differentiation of inducible progenitor cells or embryonic progenitor cells to the relevant cell type, such as T cells.

Alternatively, an immortalized cell line such as a T-cell line which retains its lytic function and could act as a therapeutic may be used.

In all these embodiments, CAR cells are generated by introducing DNA or RNA coding for the CARs by one of many means including transduction with a viral vector, transfection with DNA or RNA.

A CAR T cell of the invention may be an ex vivo T cell from a subject. The T cell may be from a peripheral blood mononuclear cell (PBMC) sample. T cells may be activated and/or expanded prior to being transduced with CAR-encoding nucleic acid, for example by treatment with an anti-CD3 monoclonal antibody.

A CAR T cell of the invention may be made by:
 (i) isolation of a T cell-containing sample from a subject or other sources listed above; and
 (ii) transduction or transfection of the T cells with one or more nucleic acid sequence(s) encoding the first and second CAR.

The T cells may then by purified, for example, selected on the basis of co-expression of the first and second CAR.

Nucleic Acid Sequences

The second aspect of the invention relates to one or more nucleic acid sequence(s) which codes for a first CAR and a second CAR as defined in the first aspect of the invention.

The nucleic acid sequence may be, for example, an RNA, a DNA or a cDNA sequence.

The nucleic acid sequence may encode one chimeric antigen receptor (CAR) which binds to CD19 and another CAR which binds to CD22.

The nucleic acid sequence may have the following structure:

AgB1-spacer1-TM1-coexpr-AbB2-spacer2-TM2 in which

AgB1 is a nucleic acid sequence encoding the antigen-binding domain of a first CAR;

Due to the degeneracy of the genetic code, it is possible to use alternative codons which encode the same amino acid sequence. For example, the codons "ccg" and "cca" both encode the amino acid proline, so using "ccg" may be exchanged for "cca" without affecting the amino acid in this position in the sequence of the translated protein.

The alternative RNA codons which may be used to encode each amino acid are summarised in Table 3.

TABLE 3

|   |   | U | | C | | A | | G | |
|---|---|---|---|---|---|---|---|---|---|
| U | | UUU | Phe | UCU | | UAU | Tyr | UGU | Cys |
| | | UUC | (F) | UCC | Ser | UAC | (Y) | UGC | (C) |
| | | UUA | Leu | UCA | (S) | UAA | Ocher | UGA | Opal |
| | | UUG | (L) | UCG | | UAG | Amber | UGG | Trp(W) |
| C | | CUU | | CCU | | CAU | His | CGU | |
| | | CUC | Leu | CCC | Pro | CAC | (H) | CGC | Arg |
| | | CUA | (L) | CCA | (P) | CAA | Gln | CGA | (R) |
| | | CUG | | CCG | | CAG | (Q) | CGG | |
| A | | AUU | | ACU | | AAU | Asn | AGU | Ser |
| | | AUC | Ile | ACC | Thr | AAC | (N) | AGC | (S) |
| | | AUA | (I) | ACA | (T) | AAA | Lys | AGA | Arg |
| | | AUG | Met(M) | ACG | | AAG | (K) | AGG | (R) |
| G | | GUU | | GCU | | GAU | Asp | GGU | |
| | | GUC | Val | GCC | Ala | GAC | (D) | GGC | Gly |
| | | GUA | (V) | GCA | (A) | GAA | Glu | GGA | (G) |
| | | GUG | | GCG | | GAG | (E) | GGG | | spacer 1 is a nucleic acid sequence encoding the spacer of a first CAR;

TM1 is a a nucleic acid sequence encoding the transmembrane domain of a first CAR;

coexpr is a nucleic acid sequence enabling co-expression of both CARs

AgB2 is a nucleic acid sequence encoding the antigen-binding domain of a second CAR;

spacer 2 is a nucleic acid sequence encoding the spacer of a second CAR;

TM2 is a a nucleic acid sequence encoding the transmembrane domain of a second CAR;

which nucleic acid sequence, when expressed in a T cell, encodes a polypeptide which is cleaved at the cleavage site such that the first and second CARs are co-expressed at the cell surface.

The first CAR may bind CD19 and the second CAR may bind CD22. Alternatively the first CAR may bind CD22 and the second CAR may bind CD19.

Alternative codons may be used in regions of sequence encoding the same or similar amino acid sequences, in order to avoid homologous recombination.

Figure 4:
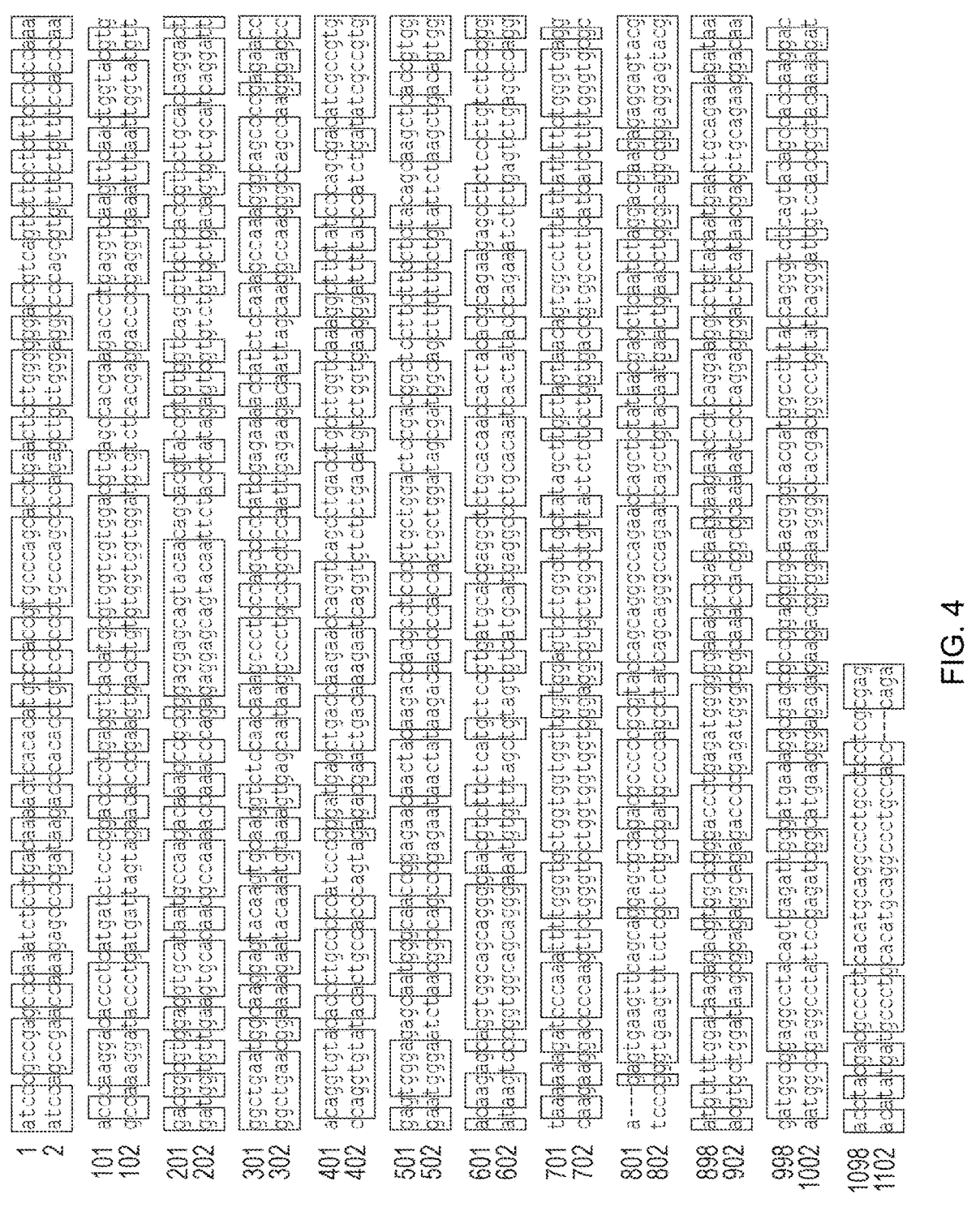

Alternative codons may be used in the portions of nucleic acid sequence which encode the spacer of the first CAR and the spacer of the second CAR, especially if the same or similar spacers are used in the first and second CARs. FIG. 4 shows two sequences encoding the spacer HCH2CH3—hinge, in one of which alternative codons have been used.

Alternative codons may be used in the portions of nucleic acid sequence which encode the transmembrane domain of the first CAR and the transmembrane of the second CAR, especially if the same or similar transmembrane domains are used in the first and second CARs. FIG. 4 shows two sequences encoding the CD28 transmembrane domain, in one of which alternative codons have been used.

Alternative codons may be used in the portions of nucleic acid sequence which encode all or part of the endodomain of the first CAR and all or part of the endodomain of the second CAR. Alternative codons may be used in the CD3 zeta endodomain. FIG. 4 shows two sequences encoding the CD3 zeta endodomain, in one of which alternative codons have been used.

Alternative codons may be used in one or more co-stimulatory domains, such as the CD28 endodomain.

Alternative codons may be used in one or more domains which transmit survival signals, such as OX40 and 41 BB endodomains.

Alternative codons may be used in the portions of nucleic acid sequence encoding a CD3zeta endodomain and/or the portions of nucleic acid sequence encoding one or more costimulatory domain(s) and/or the portions of nucleic acid sequence encoding one or more domain(s) which transmit survival signals.

Vector

The present invention also provides a vector, or kit of vectors which comprises one or more CAR-encoding nucleic acid sequence(s). Such a vector may be used to introduce the nucleic acid sequence(s) into a host cell so that it expresses the first and second CARs.

The vector may, for example, be a plasmid or a viral vector, such as a retroviral vector or a lentiviral vector, or a transposon based vector or synthetic mRNA.

The vector may be capable of transfecting or transducing a T cell.

Pharmaceutical Composition

The present invention also relates to a pharmaceutical composition containing a plurality of CAR-expressing cells, such as T cells or NK cells according to the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention are capable of killing cancer cells, such as B-cell lymphoma cells. CAR-expressing cells, such as T cells, may either be created ex vivo either from a patient's own peripheral blood (1st party), or in the setting of a haematopoietic stem cell transplant from donor peripheral blood (2nd party), or peripheral blood from an unconnected donor (3rd party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

The cells of the present invention may be capable of killing target cells, such as cancer cells. The target cell is recognisable by expression of CD19 or CD22.

TABLE 4 expression of lymphoid antigens on lymphoid leukaemias

|  | CD19 | CD22 | CD10 | CD7 | CD5 | CD3 | cIg μ | sIg μ |
|---|---|---|---|---|---|---|---|---|
| Early pre-B | 100 | >95 | 95 | 5 | 0 | 0 | 0 | 0 |
| Pre-B | 100 | 100 | >95 | 0 | 0 | 0 | 100 | 0 |
| Transitional pre-B | 100 | 100 | 50 | 0 | 0 | 0 | 100 | 0 |
| B | 100 | 100 | 50 | 0 | 0 | 0 | >95 | >95 |
| T | <5 | 0 | 0 | 100 | 95 | 100 | 0 | 0 |

Taken from Campana et al. (Immunophenotyping of leukemia. J. Immunol. Methods 243, 59-75 (2000)). cIg μ—cytoplasic Immunoglobulin heavy chain; sIg μ—surface Immunoglobulin heavy chain.

Figure 2:
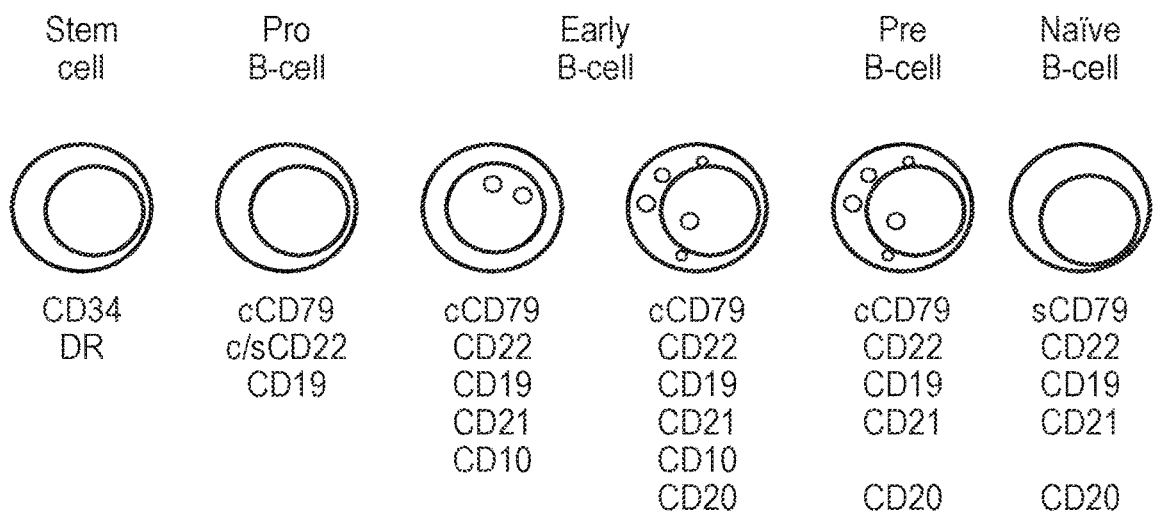
FIG. 2: B-cell maturation pathway/B-cell ontogeny. DR=HLA-DR; cCD79=cytoplasmic CD79; cCD22=CYTOPHASMIC CD22. Both CD19 and CD22 antigens are expressed during early stages in B-cell maturation. It is these cells that develop into B-cell acute leukaemias. Targeting both CD19 as well as CD22 simultaneously is most suited for targeting B-cell acute leukaemias.
Figure 3A:
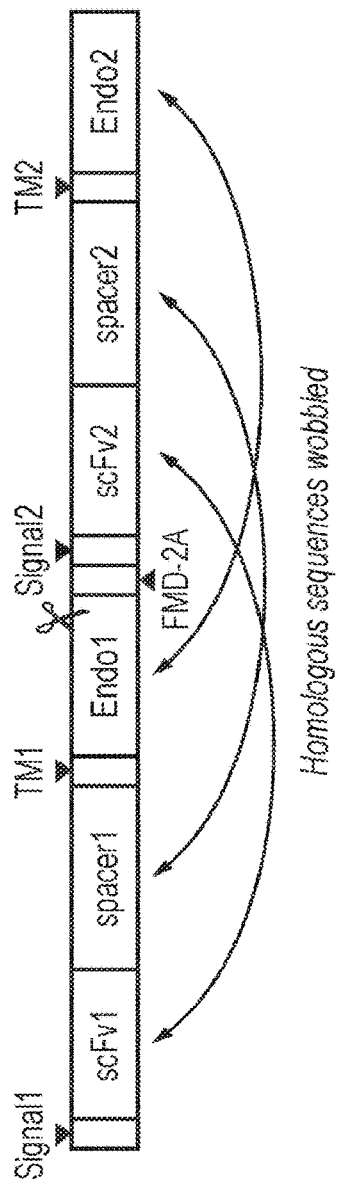
FIGS. 3A-3B: Strategies for design of an anti-CD19 OR CD22 CAR cassette. Binders which recognize CD19 and binders which recognize CD22 are selected. An optimal spacer domain and signalling domain is selected for each CAR.
Figure 3B:
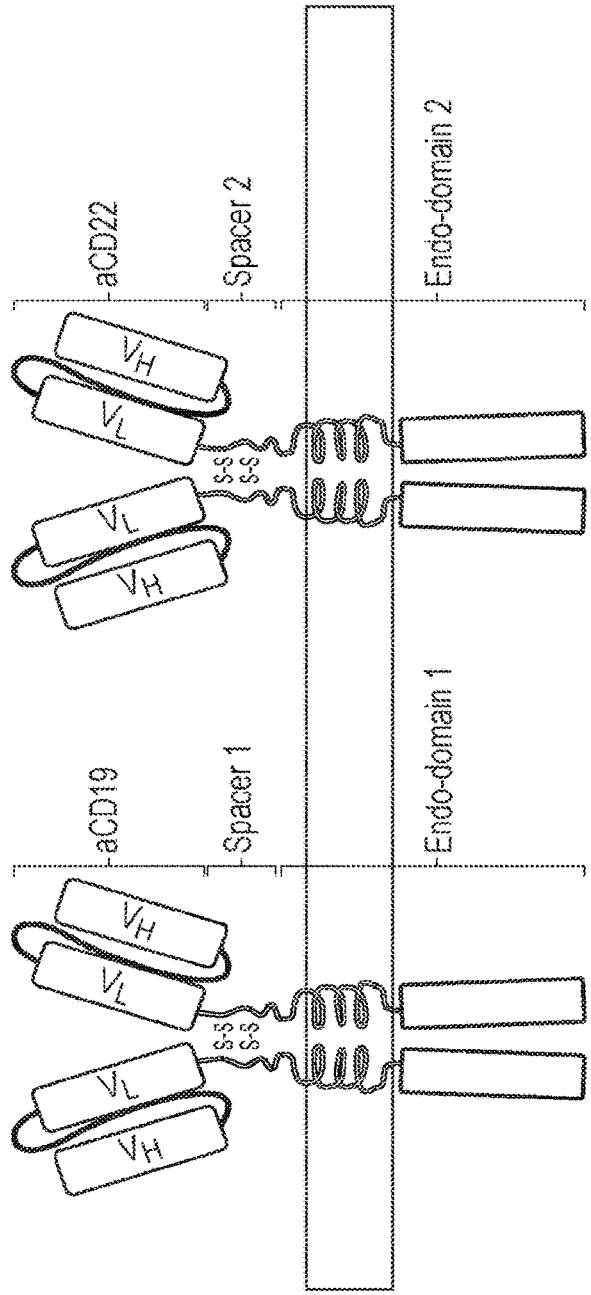

The expression of commonly studied lymphoid antigens on different types of B-cell leukaemias closely mirrors that of B-cell ontogeny (see FIG. 2).

The T cells of the present invention may be used to treat cancer, in particular B-cell malignancies.

Examples of cancers which express CD19 or CD22 are B-cell lymphomas, including Hodgkin's lymphoma and non-Hodgkins lymphoma; and B-cell leukaemias.

For example the B-cell lymphoma may be Diffuse large B cell lymphoma (DLBCL), Follicular lymphoma, Marginal zone lymphoma (MZL) or Mucosa-Associated Lymphatic Tissue lymphoma (MALT), Small cell lymphocytic lymphoma (overlaps with Chronic lymphocytic leukemia), Mantle cell lymphoma (MCL), Burkitt lymphoma, Primary mediastinal (thymic) large B-cell lymphoma, Lymphoplasmacytic lymphoma (may manifest as Waldenström macroglobulinemia), Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma or Primary central nervous system lymphoma.

The B-cell leukaemia may be acute lymphoblastic leukaemia, B-cell chronic lymphocytic leukaemia, B-cell prolymphocytic leukaemia, precursor B lymphoblastic leukaemia or hairy cell leukaemia.

The B-cell leukaemia may be acute lymphoblastic leukaemia.

Treatment with the T cells of the invention may help prevent the escape or release of tumour cells which often occurs with standard approaches.

The invention will now be further described by way of Examples, which are meant to serve to assist one of ordinary skill in the art in carrying out the invention and are not intended in any way to limit the scope of the invention.

EXAMPLES

Example 1—Proof-of-Concept of a CD19/CD22 Logical 'OR' Gate

A CD19 'OR' CD22 CAR gate was constructed by co-expression of a CD19 and a CD22 CAR in the same vector. The anti-CD19 binder was a scFv derived from the re-surfaced B4 antibody (Roguska et al. (1996) Protein Eng. 9, 895-904), and the anti-CD22 binder was a scFv derived from the humanized RFB4 antibody. A human IgG1 hinge-CH2-CH3 spacer was used for both CARs, the coding sequence of which was codon-wobbled to avoid homologous recombination by the integrating vector. The TM domain in both CARs was derived from that of CD28, and both CAR endodomains comprised of CD3-Zeta. Once again, these homologous sequences were codon-wobbled. Co-expression was achieved by cloning the two CARs in frame separated by a FMD-2A peptide. The nucleic acid and amino acid sequence of the CD19/CD22 'OR' gate construct are shown as SEQ ID NOs: 13 and 14; respectively.

SEQ ID NO: 13
ATGAGCCTGCCCGTGACCGCCCTGCTGCTGCCCCTGGCCCTGCTGCTGCA

CGCCGCCAGACCATACCCCTACGACGTGCCCGACTACGCCAGCCTGAGCG

GAGGCGGCGGCAGCCAGGTGCAGCTGGTGCAGAGCGGAGCCGAGGTGAAG

AAGCCTGGCGCCAGCGTGAAGGTGTCCTGTAAGGCCAGCGGCTACACCTT

CACCAGCAACTGGATGCACTGGGTGAGGCAGGCCCCTGGACAGGGACTGG

AGTGGATGGGCGAGATCGACCCCAGCGACAGCTACACCAACTACAACCAG

-continued

```
AAGTTCAAGGGCCGGGTGACCATCACCGTGGATAAGAGCGCCAGCACCGC
CTACATGGAGCTGTCCAGCCTGAGAAGCGAGGATACCGCCGTGTACTACT
GTGCCAGAGGCAGCAACCCCTACTACTACGCTATGGACTACTGGGGCCAG
GGCACCCTGGTGACCGTGTCCAGCGGCGGAGGAGGAAGCGGAGGGGCGG
ATCTGGCGGCGGAGGGAGCGAGATCGTGCTGACCCAGAGCCCCGCCACCC
TGAGCCTGAGCCCTGGCGAGAGAGCCACCCTGTCCTGTAGCGCCAGCAGC
GGCGTGAATTACATGCACTGGTATCAGCAGAAGCCCGGCCAGGCCCCCAG
AAGATGGATCTACGACACCAGCAAGCTGGCCAGCGGCGTGCCCGCCAGAT
TCAGCGGCAGCGGCTCCGGCACCAGCTACAGCCTGACCATCAGCAGCCTG
GAGCCTGAGGATTTCGCCGTGTATTATTGCCACCAGAGGGGCAGCTACAC
CTTTGGCGGCGGAACAAAGCTGGAGATCAAGCGCTCAGATCCCACCACGA
CGCCAGCGCCGCGACCACCAACACCGGCGCCCACCATCGCGTCGCAGCCC
CTGTCCCTGCGCCCAGAGGCGTGCCGGCCAGCGGCGGGGGCGCAGTGCA
CACGAGGGGCTGGACTTCGCCTGTGATATCTTTTGGGTGCTGGTGGTGG
TTGGTGGAGTCCTGGCTTGCTATAGCTTGCTAGTAACAGTGGCCTTTATT
ATTTTCTGGGTGAGGAGAGTGAAGTTCAGCAGGAGCGCAGACGCCCCGC
GTACCAGCAGGGCCAGAACCAGCTCTATAACGAGCTCAATCTAGGACGAA
GAGAGGAGTACGATGTTTTGGACAAGAGACGTGGCCGGGACCCTGAGATG
GGGGGAAAGCCGAGAAGGAAGAACCCTCAGGAAGGCCTGTACAATGAACT
GCAGAAAGATAAGATGGCCGAGGCCTACAGTGAGATTGGGATGAAAGGCG
AGCGCCGGAGGGGCAAGGGGCACGATGGCCTTTACCAGGGTCTCAGTACA
GCCACCAAGGACACCTACGACGCCCTTCACATGCAGGCCCTGCCTCCTCG
CAGAGCCGAGGGCAGGGAAGTCTTCTAACATGCGGGACGTGGAGGAAA
ATCCCGGGCCCATGGAGTTTGGGCTGAGCTGGCTTTTTCTTGTGGCTATT
TTAAAAGGTGTCCAGTGCGAGGTGCAGCTGGTGGAGTCTGGGGGAGGCTT
GGTCCAGCCAGGGGGGTCCCTGCGCCTCTCCTGTGCAGCCTCTGGATTCG
CTTTCAGTATCTATGACATGTCTTGGGTCCGCCAGGTTCCGGGGAAGGGG
CTGGAGTGGGTCTCATATATTAGTAGTGGTGGTGGTACCACCTATTACCC
GGACACTGTGAAGGGCCGCTTCACCATCTCCCGTGACAATTCCCGCAACA
CTCTGGATCTTCAAATGAACAGTCTGCGCGTCGAGGACACGGCTGTCTAT
TATTGTGCGCGTCATAGTGGCTACGGTAGTAGCTACGGGGTTTTGTTTGC
TTACTGGGGCCAAGGAACCCTGGTCACCGTCTCCTCAGGTGGAGGCGGTT
CAGGCGGAGGTGGCTCTGGCGGTGGCGGATCGGACATCCAGATGACTCAG
TCTCCGTCCTCCCTGTCTGCATCTGTAGGAGACCGCGTCACCATCACCTG
CCGTGCAAGTCAGGACATTAGCAATTATTTAAACTGGCTTCAACAGAAAC
CGGGGAAAGCCCCGAAGCTCCTGATTTACTACACATCAATCTTACACTCA
GGAGTCCCGTCACGCTTCAGCGGCAGTGGATCTGGGACAGAATTCACTCT
CACAATCAGCAGCCTGCAGCCGGAAGATTTTGCAACTTATTACTGTCAAC
AGGGTAATACGCTTCCGTGGACGTTTGGCCAGGGGACCAAACTGGAAATC
AAACGTTCGGATCCAGCCGAACCAAAGAGCCCCGATAAGACCCACACCTG
```

```
TCCCCCCTGCCCAGCCCCAGAGCTGCTGGGAGGCCCCAGCGTGTTTCTGT
TTCCACCCAAGCCAAAGGATACCCTGATGATTAGTAGAACACCCGAAGTG
ACCTGTGTGGTGGTGGATGTGTCTCACGAGGACCCCGAGGTGAAATTTAA
TTGGTATGTTGATGGTGTTGAAGTGCACAACGCCAAAACCAAACCCAGAG
AGGAGCAGTACAATTCTACCTATAGAGTCGTGTCTGTGCTGACAGTGCTG
CATCAGGATTGGCTGAACGGAAAAGAATACAAATGTAAAGTGAGCAATAA
GGCCCTGCCCGCTCCAATTGAGAAGACAATTAGCAAGGCCAAGGGCCAGC
CAAGGGAGCCCCAGGTGTATACACTGCCACCCAGTAGAGACGAACTGACA
AAGAATCAGGTGTCTCTGACATGTCTGGTGAAGGGATTTTACCCATCTGA
TATCGCCGTGGAATGGGAATCTAACGGCCAGCCCGAGAATAACTATAAGA
CAACCCCACCAGTGCTGGATAGCGATGGCAGCTTTTTTCTGTATTCTAAG
CTGACAGTGGATAAGTCCCGGTGGCAGCAGGGAAATGTGTTTAGCTGTAG
TGTCATGCATGAGGCCCTGCACAATCACTATACCCAGAAATCTCTGAGTC
TGAGCCCAGGCAAGAAGGACCCCAAGTTCTGGGTCCTGGTGGTGGTGGGA
GGCGTGCTGGCCTGTTACTCTCCTGGTGACCGTGGCCTTCATCATCTT
TTGGGTGCGCTCCCGGGTGAAGTTTTCTCGCTCTGCCGATGCCCCAGCCT
ATCAGCAGGGCCAGAATCAGCTGTACAATGAACTGAACCTGGGCAGGCGG
GAGGAGTACGACGTGCTGGATAAGCGGAGAGGCAGAGACCCCGAGATGGG
CGGCAAACCACGGCGCAAAAATCCCCAGGAGGGACTCTATAACGAGCTGC
AGAAGGACAAAATGGCCGAGGCCTATTCCGAGATCGGCATGAAGGGAGAG
AGAAGACGCGGAAAGGGCCACGACGGCCTGTATCAGGGATTGTCCACCGC
TACAAAAGATACATATGATGCCCTGCACATGCAGGCCCTGCCACCCAGAT
GA
```

SEQ ID NO: 14
```
MSLPVTALLLPLALLLHAARPYPYDVPDYASLSGGGGSQVQLVQSGAEVK
KPGASVKVSCKASGYTFTSNWMHWVRQAPGQGLEWMGEIDPSDSYTNYNQ
KFKGRVTITVDKSASTAYMELSSLRSEDTAVYYCARGSNPYYYAMDYWGQ
GTLVTVSSGGGGSGGGGSGGGGSEIVLTQSPATLSLSPGERATLSCSASS
GVNYMHWYQQKPGQAPRRWIYDTSKLASGVPARFSGSGSGTSYSLTISSL
EPEDFAVYYCHQRGSYTEGGGTKLEIKRSDPTTTPAPRPPTPAPTIASQP
LSLRPEACRPAAGGAVHTRGLDFACDIFWVLVVVGGVLACYSLLVTVAFI
IFWVRRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPRRAEGRGSLLTCGDVEENPGPMEFGLSWLFLVAI
LKGVQCEVQLVESGGGLVQPGGSLRLSCAASGFAFSIYDMSWVRQVPGKG
LEWVSYISSGGGTTYYPDTVKGRFTISRDNSRNTLDLQMNSLRVEDTAVY
YCARHSGYGSSYGVLFAYWGQGTLVTVSSGGGGSGGGGSGGGGSDIQMTQ
SPSSLSASVGDRVTITCRASQDISNYLNWLQQKPGKAPKLLIYYTSILHS
GVPSRFSGSGSGTEFTLTISSLQPEDFATYYCQQGNTLPWTFGQGTKLEI
KRSDPAEPKSPDKTHTCPPCPAPELLGGPSVFLFPPKPKDTLMISRTPEV
TCVVVDVSHEDPEVKFNWYVDGVEVHNAKTKPREEQYNSTYRVVSVLTVL
```

-continued

```
HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGKKDPKFWVLVVVG

GVLACYSLLVTVAFIIFWVRSRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR
```

To demonstrate co-expression of both CARs, the scFv of each CAR was tagged with an epitope tag (HA or V5 respectively). This subsequent single open-reading frame was cloned into the SFG retroviral vector. T-cells were transduced with this vector and both CARs could be detected on the T-cells surface expressing the cassette by staining with anti-HA and anti-V5 and studying expression by flow cytometry.

Next, T-cells expressing the CD19 OR CD22 CAR gate were challenged with target cells, expressing neither, both or one antigen along with control T-cells which expressed no CARs, or just anti-CD19 CAR alone, or anti-CD22 CAR alone. We found that the OR-gated CAR T-cells could kill target cells expressing either one or both target antigens (FIG. 5A-5C).

Example 2—Identification and Characterisation of CD19ALAb and CD22ALAb

A CD19-binder (CD19ALAb) was identified, humanised and the binding affinities of both murine and humanised IgGs and scFvs were identified and compared with the "gold-standard" anti-CD19 binder, fmc63. In parallel, and a CD22-binder (CD22ALAb) was identified, humanised and the binding affinities of both murine and humanised IgGs and scFvs were identified and compared with the "gold-standard" anti-CD22 binder, M971.

Experiments were performed on a Biacore T200 instrument using HBS-P as running and dilution buffer. BIAevaluation software Version 2.0 was used for data processing. For binding kinetics, mouse anti-human IgG or goat anti-mouse IgG was covalently coupled to a CM5 Sensor Chip. IgG or scFv-Fc proteins were captured, and various concentrations of interaction partner protein injected over the flow cell at a flow rate of 30 µl/min. Kinetic rate constants were obtained by curve fitting according to a 1:1 Langmuir binding model. Bulk refractive index differences were subtracted using a blank control flow cell in which capture antibody had been immobilized to the same level as the active surface. A double reference subtraction was performed using buffer alone.

Figure 6:
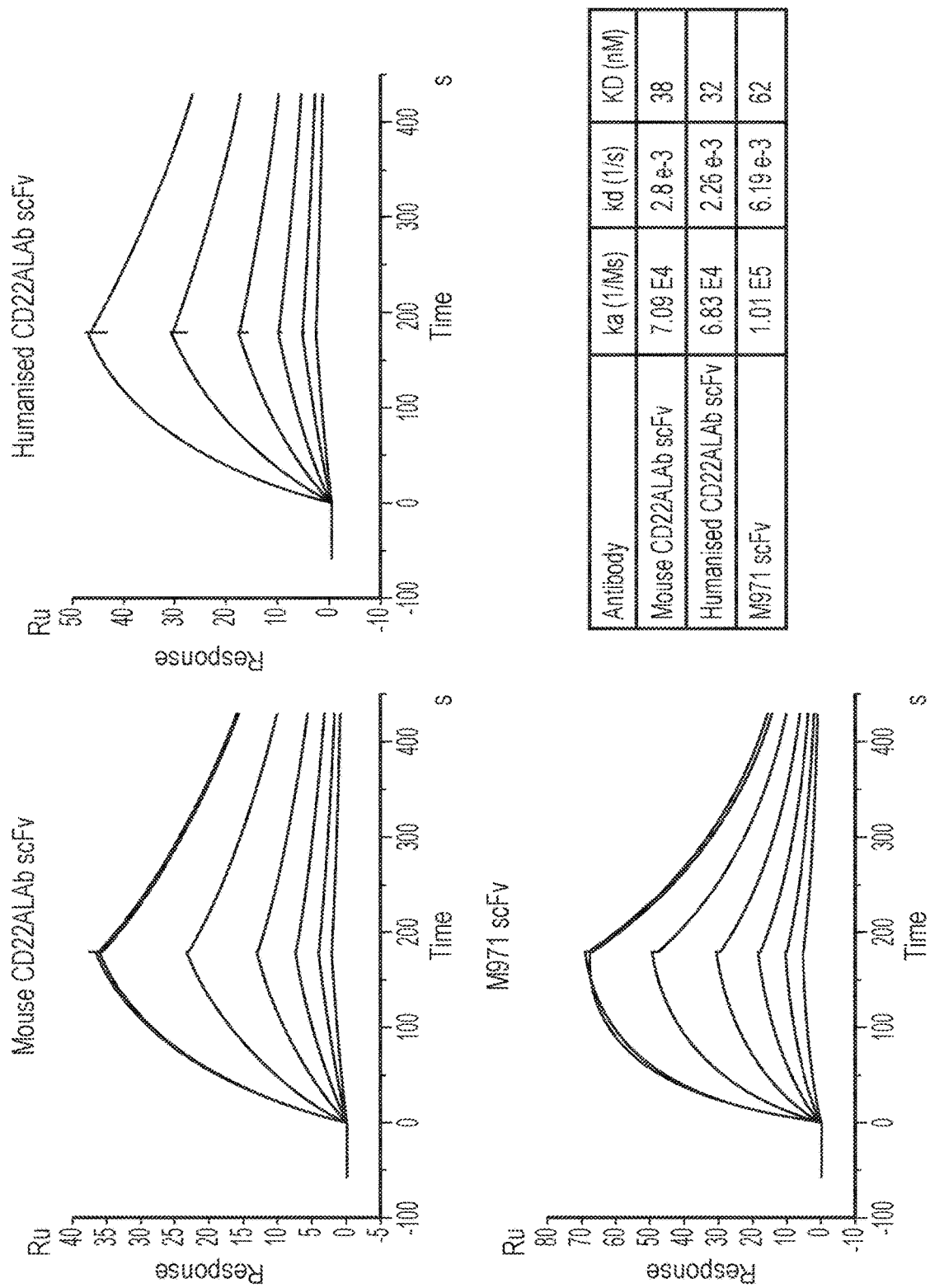
FIG. 6: Biacore affinity determination for murine CD22ALAb scFv, humanized CD22ALAb scFv and M971 scFv.
Figure 7:
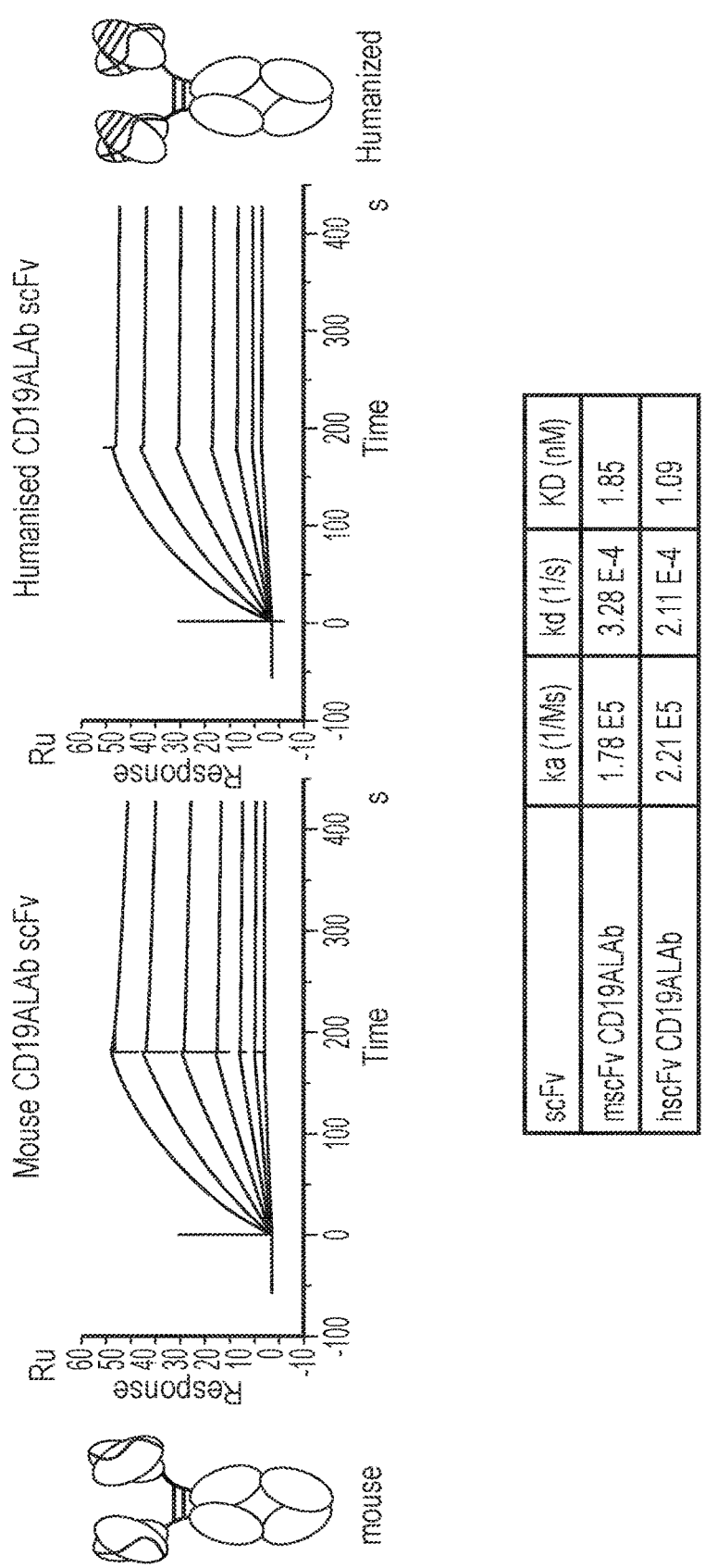
FIG. 7: Biacore affinity determination for murine CD19ALAb scFv and humanized CD19ALAb.

The results are shown in FIGS. 6 to 8.

The data show that humanised CD22ALAb has comparable binding affinity to CD22 to murine CD22ALAb (FIG. 6) and similar binding kinetics. Both murine and humanised CD22ALAb in an scFv format have significantly higher binding affinity to CD22 than the gold-standard CD22-binding antibody, M971 (FIG. 6).

Although the binding affinity of murine and humanised CD19ALAb in an IgG format was found to be similar (data not shown), surprisingly the binding affinity of humanised CD19ALAb was found to be higher than murine CD19ALAb in an scFv format (FIG. 7). The binding affinity of CD19ALAb is comparable (possibly slightly better) than that of the gold-standard anti-CD19 Ab, fmc63 (FIG. 8).

Example 3—Comparative Functional Assays with CD19ALAb/Fmc63 CARs and CD22ALAb/M971 CARs The antigen binding domain of a CAR can affect its function. In this study, CARs were created comprising CD19ALAb and CD22ALAb and function was compared with an equivalent CAR having an antigen-binding domain based on fmc63 or M971.

CARs comprising scFvs based on fmc63 (anti-CD19) and M971 (anti-CD22) can be considered as the gold standard antibodies as both CARs are in clinical development.

Figure 9:
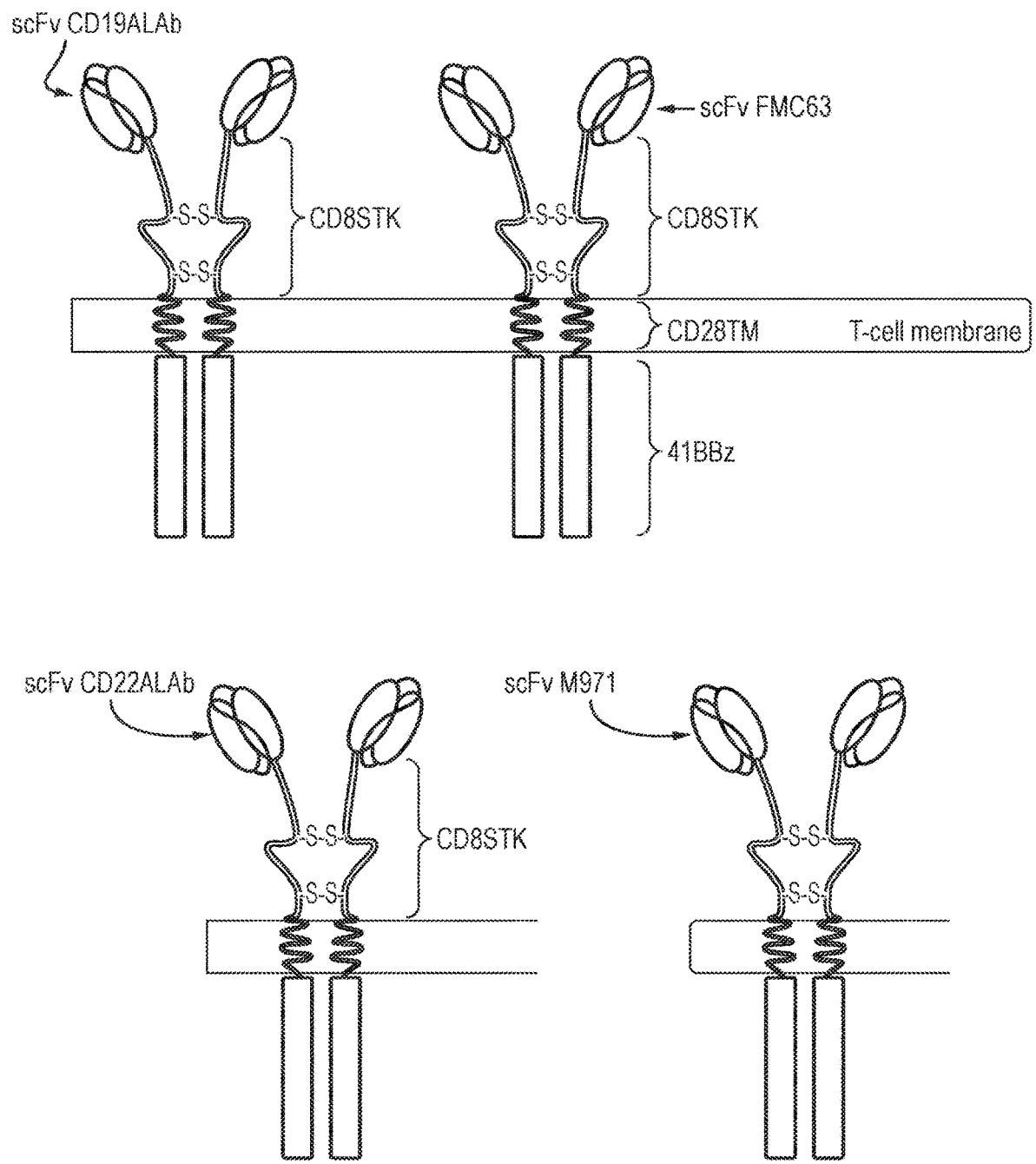
FIG. 9: Schematic diagram illustrating CD19ALAb CAR, fmc63 CAR, CD22ALAb CAR and M971 CAR used in the comparative studies.

CARs were constructed and expressed based on CD19ALAb, fmc63, CD22ALAb and M971. Their structure is shown in FIG. 9. The CARs differed solely in their antigen binding domain. In all constructs, the binding domains were linked to the membrane with a CD8 stalk spacer and contained intracellular activatory motifs from 41 BB and CD3-zeta.

Retroviruses were produced by transient transfection of 293T cells with plasmids encoding the CARs, gag/pol and the envelope protein RD114. After 3 days the supernatants were harvested and used to transduce PHA/IL2-activated PBMCs with equal titres of retrovirus on retronectin-coated plates. Six days post-transduction CAR-expression was confirmed by flow cytometry and PBMCs were co-cultured in a 1:1 ratio with either CD19+ BFP SupT1 cells (fmc63 and CD19ALAb CARs) or CD22+ BFP SupT1 cells (M971 and CD22ALAb CARs). Target cell killing was assayed after one and three days. Also after one and three days, supernatants were removed and interferon-γ levels were assayed by ELISA.

Figure 10:
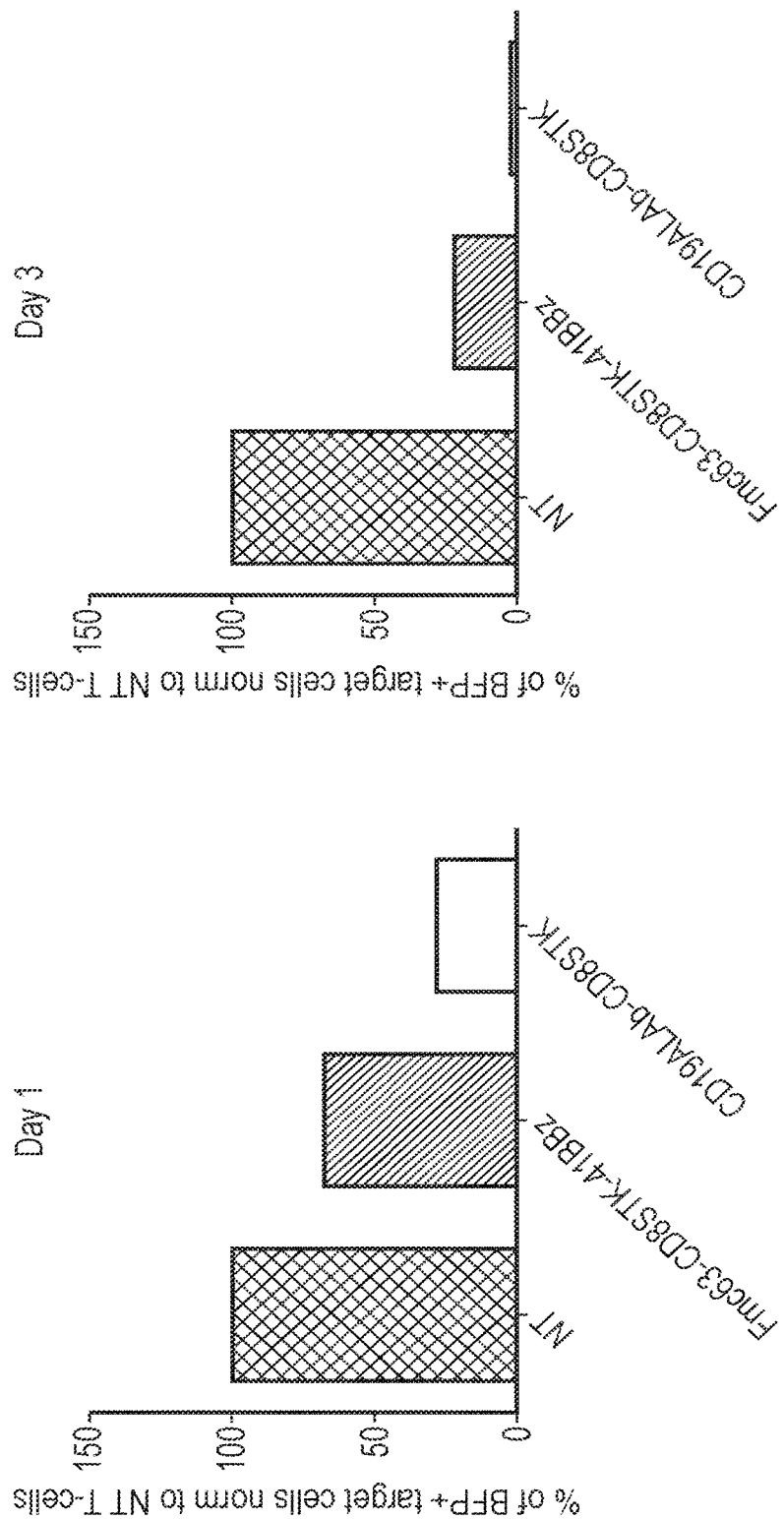
FIG. 10: Killing assay of CD19 positive target cells comparing a CAR with a CD19ALAb antigen binding domain and equivalent CAR with an fmc63 binding domain.
Figure 11B:
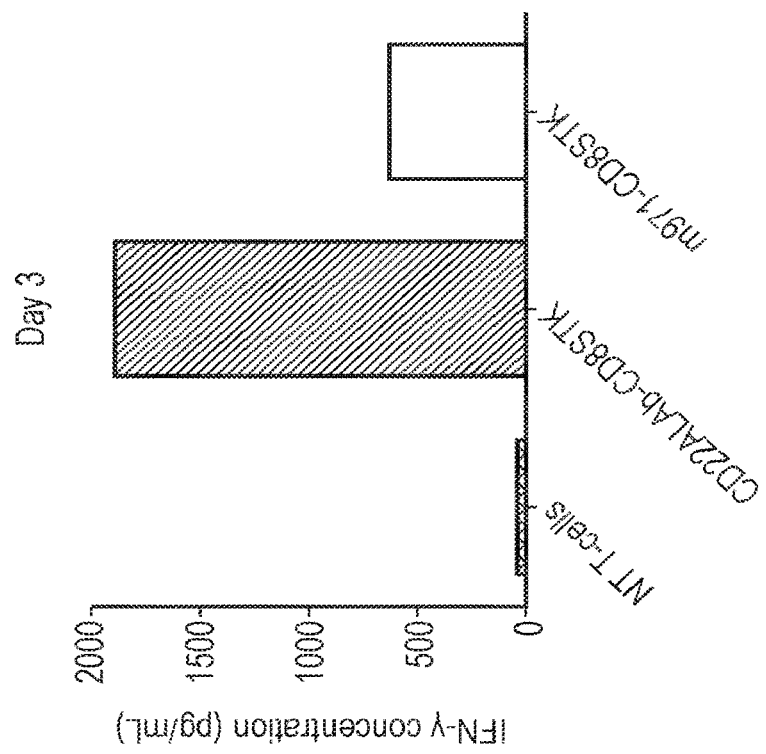
FIGS. 11A-11B.
Figure 11A:
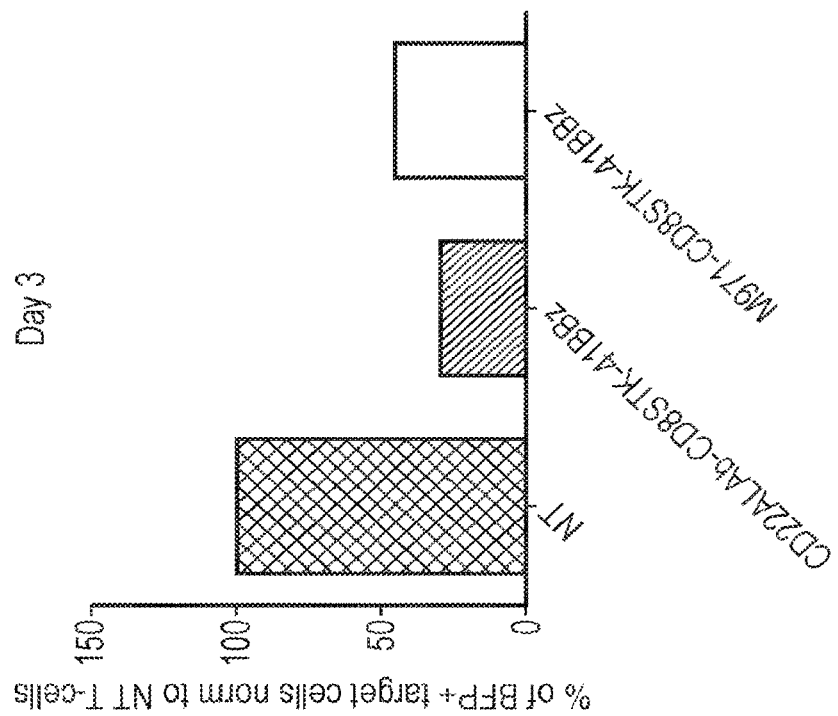

The results are shown in FIGS. 10 and 11A-11B.

As shown in FIG. 10, the CAR with a CD19ALAb antigen binding domain gave more killing of CD19+ve target cells (FIG. 10) at both Day 1 and Day 3, than the equivalent CAR with a fmc63 binding domain.

With regard to CD22, the CAR with a CD22ALAb antigen binding domain gave more killing of CD22+ve target cells (FIG. 11A) after three days than the equivalent CAR with an M971 binding domain. IFNγ release was significantly higher with the CD22ALAb CAR than the M971 CAR after the same time frame.

CARs having an antigen-binding domain based on CD19ALAb and CD22ALAb therefore have improved properties in terms of target cell killing than equivalent CARs based on fmc63 and M971.

The CD22ALAb result is particularly surprising, given the findings reported in Haso et al (2013) as above. In that study, different anti-CD22 CARs were made and tested, with binding domains based on the anti-CD22 antibodies HA22, BL22 and m971. HA22 and BL22 scFvs bind to Ig domain 3 of CD22, whereas m971 binds within Ig domain 5-7 of CD22 (see Haso et al (2013) FIG. 2B). It was reported that the m971-derived CAR showed superior target cell killing activity than HA22-derived CAR, which finding is attributed to the importance of the CD22 epitope targeted by the CAR (Haso et al (2013) page 1168, last full paragraph). It is concluded that targeting a membrane proximal domain of CD22 is "the key element" in developing a highly active anti-CD22 CAR (Discussion, last paragraph). Contrary to this finding, the data shown here in FIGS. 11A-11B demonstrate that CD22ALAb, which targets an epitope in Ig domain 3 of CD22—a "membrane distal" epitope compared to the Ig domain 5-7 epitope targeted by m971—has superior target cell killing ability than an m971-based anti-CD22 CAR.

Example 4—Investigating OR Gate Constructs with Different Endodomain Combinations Four OR gate constructs were developed as shown in FIGS. 13A-13D. They all encoded CD19/CD22 OR gates having identical antigen-binding domains, spacer domains and transmembrane domains: the only difference between the construct was in the endodomains, which were as shown in the following Table:

| Construct | CD19 CAR endodomain | CD22 CAR endodomain |
|---|---|---|
| A | 41BB-CD3ζ | 41BB-CD3ζ |
| B | OX40-CD3ζ | OX40-CD3ζ |
| C | 41BB-CD3ζ | CD28-CD3ζ |
| D | OX40-CD3ζ | CD28-CD3ζ |

The capacity of cells expressing each CD19/CD22 OR gate to kill Raji cells in vitro was assayed as described above. Transduced PBMCs expressing the various OR gate combinations were co-cultured for 72 hours with CD19+/CD22+ Raji target cells at both a 1:1 and 1:10 effector:target cell ratio.

Figure 14:
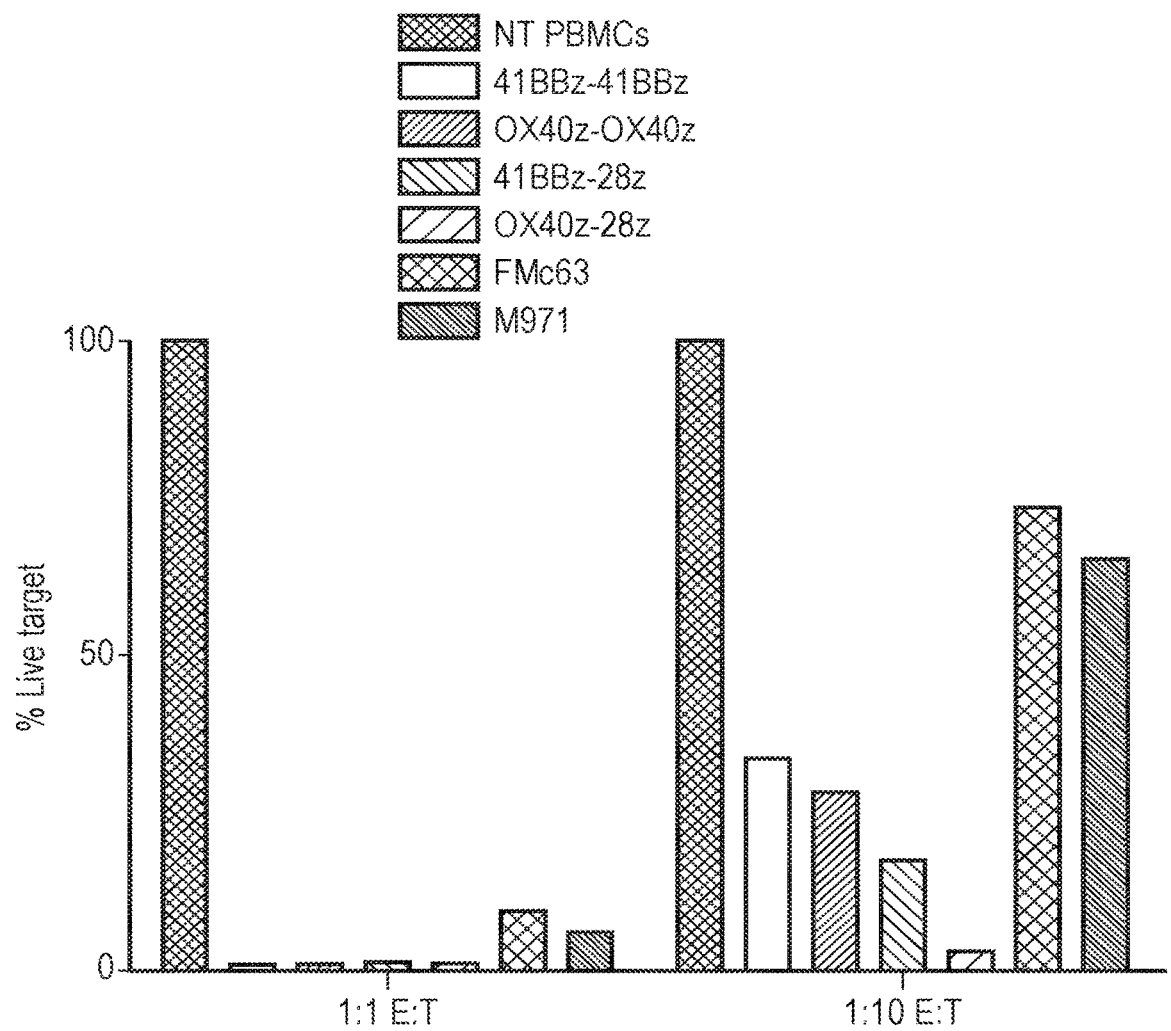
FIG. 14: Target cell killing by cells expressing the constructs shown in FIGS. 13A-13D.

The results are shown in FIG. 14. All four OR gates were found to kill target cells significantly better than the fmc63 and M971 CARs. With the 1:10 effector:target cell ratio, it was shown that the "split" endodomain OR gates, which have 4-1BBzeta/OX40zeta on one CAR and CD28zeta on the other CAR, had the best killing activity.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A cell which co-expresses a first chimeric antigen receptor (CAR) and second CAR at the cell surface, each CAR comprising an antigen binding domain, a spacer, a transmembrane domain, and an intracellular signalling domain, wherein
the cell is a T cell or a natural killer (NK) cell;
the antigen binding domain of one of the first CAR and the second CAR binds to CD19, and the antigen binding domain of the other CAR binds to CD22;
the intracellular signalling domain of the first CAR comprises a CD28 co-stimulatory domain and an ITAM-containing domain but does not comprise a 4-1BB or OX40 TNF receptor family endodomain; and
the intracellular signalling domain of the second CAR comprises a TNF receptor family endodomain selected from an OX40 or 4-1BB endodomain and an ITAM-containing domain but does not comprise a CD28 co-stimulatory domain.

2. A cell according to claim 1, wherein the first CAR has the structure:
AgB1-spacer1-TM1-costim-ITAM
in which:
AgB1 is the antigen-binding domain of the first CAR;
spacer1 is the spacer of the first CAR;
TM1 is the transmembrane domain of the first CAR;
costim is the co-stimulatory domain of the first CAR; and
ITAM is an ITAM-containing endodomain;

and the second CAR has the structure:
AgB2-spacer2-TM2-TNF-ITAM
in which:
AgB2 is the antigen-binding domain of the second CAR;
spacer2 is the spacer of the second CAR;
TM2 is the transmembrane domain of the second CAR;
TNF is the TNF receptor family endodomain of the second CAR; and
ITAM is an ITAM-containing endodomain.

3. A nucleic acid comprising a nucleic acid sequence encoding both a first chimeric antigen receptor and a second CAR
each CAR comprising an antigen binding domain, a spacer, a transmembrane domain, and an intracellular signalling domain, wherein
the antigen binding domain of one of the first CAR and the second CAR binds to CD19, and the antigen binding domain of the other CAR binds to CD22;
the intracellular signalling domain of the first CAR comprises a CD28 co-stimulatory domain and an ITAM-containing domain but does not comprise a 4-1BB or OX40 TNF receptor family endodomain; and
the intracellular signalling domain of the second CAR comprises a TNF receptor family endodomain selected from an OX40 or 4-1BB endodomain and an ITAM-containing domain but does not comprise a CD28 co-stimulatory domain.

4. A nucleic acid according to claim 3,
wherein the first CAR has the structure:
AgB1-spacer1-TM1-costim-ITAM
in which:
  AgB1 is the antigen-binding domain of the first CAR;
  spacer1 is the spacer of the first CAR;
  TM1 is the transmembrane domain of the first CAR;
  costim is the co-stimulatory domain of the first CAR; and
  ITAM is an ITAM-containing endodomain;
and the second CAR has the structure:
AgB2-spacer2-TM2-TNF-ITAM
in which:
  AgB2 is the antigen-binding domain of the second CAR;
  spacer2 is the spacer of the second CAR;
  TM2 is the transmembrane domain of the second CAR;
  TNF is the TNF receptor family endodomain of the second CAR; and
  ITAM is an ITAM-containing endodomain.

5. A nucleic acid according to claim 3, which has the following structure:
AgB1-spacer1-TM1-costim-ITAM1-coexpr-AbB2-spacer2-TM2-TNF-ITAM2 in which
  AgB1 is a nucleic acid sequence encoding the antigen-binding domain of the first CAR;
  spacer1 is a nucleic acid sequence encoding the spacer of the first CAR;
  TM1 is a nucleic acid sequence encoding the transmembrane domain of the first CAR;
  costim is a nucleic acid sequence encoding the co-stimulatory domain of the first CAR;
  ITAM1 is a nucleic acid sequence encoding the ITAM-containing endodomain of the first CAR;
  coexpr is a nucleic acid sequence containing a cleavage site and enabling co-expression of both CARs
  AgB2 is a nucleic acid sequence encoding the antigen-binding domain of the second CAR;
  spacer2 is a nucleic acid sequence encoding the spacer of the second CAR;
  TM2 is a nucleic acid sequence encoding the transmembrane domain of the second CAR;
  TNF is a nucleic acid sequence encoding the TNF family receptor endodomain of the second CAR;
  ITAM2 is a nucleic acid sequence encoding the ITAM-containing endodomain of the second CAR;
which nucleic acid sequence, when expressed in a cell, encodes a polypeptide which is cleaved at the cleavage site such that the first and second CARs are co-expressed at the cell surface.

6. A kit which comprises a nucleic acid comprising both:
(i) a first nucleic acid comprising a nucleic acid sequence encoding the first chimeric antigen receptor (CAR) as defined in claim 1, which nucleic acid sequence has the following structure:
AgB1-spacer1-TM-costim-ITAM1
in which
  AgB1 is a nucleic acid sequence encoding the antigen-binding domain of the first CAR;
  spacer1 is a nucleic acid sequence encoding the spacer of the first CAR;
  TM1 is a nucleic acid sequence encoding the transmembrane domain of the first CAR;
  costim is a nucleic acid sequence encoding the co-stimulatory domain of the first CAR;
  ITAM1 is a nucleic acid sequence encoding the ITAM-containing endodomain of the first CAR; and (ii) a second nucleic acid comprising a nucleic acid sequence encoding the second chimeric antigen receptor (CAR) as defined in claim 1, which nucleic acid sequence has the following structure:
AgB2-spacer2-TM2-TNF-ITAM2
in which
  AgB2 is a nucleic acid sequence encoding the antigen-binding domain of the second CAR;
  spacer2 is a nucleic acid sequence encoding the spacer of the second CAR;
  TM2 is a nucleic acid sequence encoding the transmembrane domain of the second CAR;
  TNF is a nucleic acid sequence encoding the TNF receptor family endodomain of the second CAR; and
  ITAM2 is a nucleic acid sequence encoding the ITAM-containing endodomain of the second CAR.

7. A vector comprising a nucleic acid according to claim 3.

8. A vector comprising a nucleic acid according to claim 4.

9. A vector comprising a nucleic acid according to claim 5.

10. A method for making a cell which co-expresses a first chimeric antigen receptor (CAR) and second CAR at the cell surface, each CAR comprising an antigen binding domain, a spacer, a transmembrane domain, and an intracellular signalling domain, wherein
  the cell is a T cell or a natural killer (NK) cell;
  the antigen binding domain of one of the first CAR and the second CAR binds to CD19, and the antigen binding domain of the other CAR binds to CD22;
  the intracellular signalling domain of the first CAR comprises a CD28 co-stimulatory domain and an ITAM-containing domain but does not comprise a 4-1BB or OX40 TNF receptor family endodomain; and
  the intracellular signalling domain of the second CAR comprises a TNF receptor family endodomain selected from OX40 or 4-1BB endodomain and an ITAM-containing domain but does not comprise a CD28 co-stimulatory domain, which method comprises the step of introducing: a nucleic acid sequence according to claim 3; or a vector comprising the nucleic acid sequence, into a T cell or NK cell ex vivo.

11. A method for making a cell which co-expresses a first chimeric antigen receptor (CAR) and second CAR at the cell surface, each CAR comprising an antigen binding domain, a spacer, a transmembrane domain, and an intracellular signalling domain, wherein
  the cell is a T cell or a natural killer (NK) cell;
  the antigen binding domain of one of the first CAR and the second CAR binds to CD19, and the antigen binding domain of the other CAR binds to CD22;
  the intracellular signalling domain of the first CAR comprises a CD28 co-stimulatory domain and an ITAM-containing domain but does not comprise a 4-1BB or OX40 TNF receptor family endodomain; and
  the intracellular signalling domain of the second CAR comprises a TNF receptor family endodomain selected from OX40 or 4-1BB endodomain and an ITAM-containing domain but does not comprise a CD28 co-stimulatory domain, which method comprises the step of introducing: a nucleic acid sequence according to claim 4; or a vector comprising the nucleic acid sequence, into a T cell or NK cell ex vivo.

12. A method for making a cell which co-expresses a first chimeric antigen receptor (CAR) and second CAR at the cell surface, each CAR comprising an antigen binding domain, a spacer, a transmembrane domain, and an intracellular signalling domain, wherein the cell is a T cell or a natural killer (NK) cell;

the antigen binding domain of one of the first CAR and the second CAR binds to CD19, and the antigen binding domain of the other CAR binds to CD22;

the intracellular signalling domain of the first CAR comprises a CD28 co-stimulatory domain and an ITAM-containing domain but does not comprise a 4-1BB or OX40 TNF receptor family endodomain; and the intracellular signalling domain of the second CAR comprises a TNF receptor family endodomain selected from OX40 or 4-1BB endodomain and an ITAM-containing domain but does not comprise a CD28 co-stimulatory domain, which method comprises the step of introducing, into a T cell or NK cell ex vivo:

(i) a first nucleic acid sequence encoding the first chimeric antigen receptor (CAR) as defined in claim 1, which nucleic acid sequence has the following structure:

AgB1-spacer1-TM-costim-ITAM1 in which

AgB1 is a nucleic acid sequence encoding the antigen-binding domain of the first CAR;

spacer1 is a nucleic acid sequence encoding the spacer of the first CAR;

TM1 is a nucleic acid sequence encoding the transmembrane domain of the first CAR;

costim is a nucleic acid sequence encoding a co-stimulatory domain;

ITAM1 is a nucleic acid sequence encoding the ITAM-containing endodomain of the first CAR; and (ii) a second nucleic acid sequence encoding the second chimeric antigen receptor (CAR) as defined in any of claim 1, which nucleic acid sequence has the following structure:

AgB2-spacer2-TM2-TNF-ITAM2 in which

AgB2 is a nucleic acid sequence encoding the antigen-binding domain of the second CAR;

spacer2 is a nucleic acid sequence encoding the spacer of the second CAR;

TM2 is a nucleic acid sequence encoding the transmembrane domain of the second CAR;

TNF is a nucleic acid sequence encoding a TNF receptor endodomain; and

ITAM2 is a nucleic acid sequence encoding the ITAM-containing endodomain of the second CAR.

13. A pharmaceutical composition comprising a plurality of cells according to claim 1.

14. A pharmaceutical composition comprising a plurality of cells according to claim 2.

15. A method of treating a disease, the method comprising administering to a subject a pharmaceutical composition according to claim 13.

16. A method of treating a disease, the method comprising administering to a subject a pharmaceutical composition according to claim 14.

17. The method according to claim 15, wherein the disease is a cancer.

18. The method according to claim 17, wherein the cancer is B cell malignancy.

19. The method according to claim 16, wherein the disease is a cancer.

20. The method according to claim 19, wherein the cancer is B cell malignancy.

* * * * *

```
                          SEQUENCE LISTING

Sequence total quantity: 49
SEQ ID NO: 1            moltype = AA  length = 21
FEATURE                 Location/Qualifiers
REGION                  1..21
                        note = Signal peptide
source                  1..21
                        mol_type = protein
                        organism = synthetic construct
SEQUENCE: 1
MGTSLLCWMA LCLLGADHAD G                                                   21

SEQ ID NO: 2            moltype = AA  length = 21
FEATURE                 Location/Qualifiers
REGION                  1..21
                        note = Signal peptide
source                  1..21
                        mol_type = protein
                        organism = synthetic construct
SEQUENCE: 2
MSLPVTALLL PLALLLHAAR P                                                   21

SEQ ID NO: 3            moltype = AA  length = 20
FEATURE                 Location/Qualifiers
REGION                  1..20
                        note = Signal peptide
source                  1..20
                        mol_type = protein
                        organism = synthetic construct
SEQUENCE: 3
MAVPTQVLGL LLLWLTDARC                                                     20

SEQ ID NO: 4            moltype = AA  length = 234
FEATURE                 Location/Qualifiers
REGION                  1..234
                        note = spacer sequence, hinge-CH2CH3 of human IgG1
source                  1..234
                        mol_type = protein
                        organism = synthetic construct
SEQUENCE: 4
AEPKSPDKTH TCPPCPAPPV AGPSVFLFPP KPKDTLMIAR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GKKD        234

SEQ ID NO: 5            moltype = AA  length = 46
FEATURE                 Location/Qualifiers
REGION                  1..46
                        note = spacer sequence, human CD8 stalk
source                  1..46
                        mol_type = protein
```

```
                            organism = synthetic construct
SEQUENCE: 5
TTTPAPRPPT PAPTIASQPL SLRPEACRPA AGGAVHTRGL DFACDI              46

SEQ ID NO: 6                moltype = AA  length = 20
FEATURE                     Location/Qualifiers
REGION                      1..20
                            note = spacer sequence, human IgG1 hinge
source                      1..20
                            mol_type = protein
                            organism = synthetic construct
SEQUENCE: 6
AEPKSPDKTH TCPPCPKDPK                                           20

SEQ ID NO: 7                moltype = AA  length = 185
FEATURE                     Location/Qualifiers
REGION                      1..185
                            note = spacer sequence, CD2 ectodomain
source                      1..185
                            mol_type = protein
                            organism = synthetic construct
SEQUENCE: 7
KEITNALETW GALGQDINLD IPSFQMSDDI DDIKWEKTSD KKKIAQFRKE KETFKEKDTY   60
KLFKNGTLKI KHLKTDDQDI YKVSIYDTKG KNVLEKIFDL KIQERVSKPK ISWTCINTTL  120
TCEVMNGTDP ELNLYQDGKH LKLSQRVITH KWTTSLSAKF KCTAGNKVSK ESSVEPVSCP  180
EKGLD                                                            185

SEQ ID NO: 8                moltype = AA  length = 259
FEATURE                     Location/Qualifiers
REGION                      1..259
                            note = spacer sequence, CD34 ectodomain
source                      1..259
                            mol_type = protein
                            organism = synthetic construct
SEQUENCE: 8
SLDNNGTATP ELPTQGTFSN VSTNVSYQET TTPSTLGSTS LHPVSQHGNE ATTNITETTV   60
KFTSTSVITS VYGNTNSSVQ SQTSVISTVF TTPANVSTPE TTLKPSLSPG NVSDLSTTST  120
SLATSPTKPY TSSSPILSDI KAEIKCSGIR EVKLTQGICL EQNKTSSCAE FKKDRGEGLA  180
RVLCGEEQAD ADAGAQVCSL LLAQSEVRPQ CLLLVLANRT EISSKLQLMK KHQSDLKKLG  240
ILDFTEQDVA SHQSYSQKT                                              259

SEQ ID NO: 9                moltype = AA  length = 140
FEATURE                     Location/Qualifiers
REGION                      1..140
                            note = comprising CD28 transmembrane domain and CD3 Z
                               endodomain
source                      1..140
                            mol_type = protein
                            organism = synthetic construct
SEQUENCE: 9
FWVLVVVGGV LACYSLLVTV AFIIFWVRRV KFSRSADAPA YQQGQNQLYN ELNLGRREEY   60
DVLDKRRGRD PEMGGKPRRK NPQEGLYNEL QKDKMAEAYS EIGMKGERRR GKGHDGLYQG  120
LSTATKDTYD ALHMQALPPR                                             140

SEQ ID NO: 10               moltype = AA  length = 180
FEATURE                     Location/Qualifiers
REGION                      1..180
                            note = comprising CD28 transmembrane domain and CD28 and
                               CD3 Zeta endodomains
source                      1..180
                            mol_type = protein
                            organism = synthetic construct
SEQUENCE: 10
FWVLVVVGGV LACYSLLVTV AFIIFWVRSK RSRLLHSDYM NMTPRRPGPT RKHYQPYAPP   60
RDFAAYRSRV KFSRSADAPA YQQGQNQLYN ELNLGRREEY DVLDKRRGRD PEMGGKPRRK  120
NPQEGLYNEL QKDKMAEAYS EIGMKGERRR GKGHDGLYQG LSTATKDTYD ALHMQALPPR  180

SEQ ID NO: 11               moltype = AA  length = 216
FEATURE                     Location/Qualifiers
REGION                      1..216
                            note = comprising CD28 transmembrane domain and CD28, OX40
                               and CD3 Zeta endodomains
source                      1..216
                            mol_type = protein
                            organism = synthetic construct
SEQUENCE: 11
FWVLVVVGGV LACYSLLVTV AFIIFWVRSK RSRLLHSDYM NMTPRRPGPT RKHYQPYAPP   60
RDFAAYRSRD QRLPPDAHKP PGGGSFRTPI QEEQADAHST LAKIRVKFSR SADAPAYQQG  120
QNQLYNELNL GRREEYDVLD KRRGRDPEMG GKPRRKNPQE GLYNELQKDK MAEAYSEIGM  180
```

KGERRRGKGH DGLYQGLSTA TKDTYDALHM QALPPR                                          216

SEQ ID NO: 12           moltype = AA  length = 20
FEATURE                 Location/Qualifiers
REGION                  1..20
                        note = 2A-like sequence
source                  1..20
                        mol_type = protein
                        organism = synthetic construct
SEQUENCE: 12
RAEGRGSLLT CGDVEENPGP                                                             20

SEQ ID NO: 13           moltype = DNA  length = 3402
FEATURE                 Location/Qualifiers
misc_feature            1..3402
                        note = CD19/CD22 'OR' gate construct
source                  1..3402
                        mol_type = other DNA
                        organism = synthetic construct
SEQUENCE: 13
atgagcctgc ccgtgaccgc cctgctgctg cccctggccc tgctgctgca cgccgccaga    60
ccatacccct acgacgtgcc cgactacgcc agcctgagcg gaggcggcgg cagccaggtg   120
cagctggtgc agagcggagc cgaggtgaag aagcctggcg ccagcgtgaa ggtgtcctgt   180
aaggccagcg gctacacctt caccagcaac tggatgcact gggtgaggca ggcccctgga   240
cagggactgg agtggatggg cgagatcgac cccagcgaca gctacaccaa ctacaaccag   300
aagttcaagg gccgggtgac catcaccgtg gataagagcg ccagcaccgc ctacatggag   360
ctgtccagcc tgagaagcga ggataccgcc gtgtactact gtgccagagg cagcaacccc   420
tactactacg ctatggacta ctggggccag ggcaccctgg tgaccgtgtc cagcggcgga   480
ggaggaagcg gaggggcgg atctggcgg ggagggagcg agatcgtgct gacccagagc   540
cccgccaccc tgagcctgag ccctggcgag agagccaccc tgtcctgtag cgccagcagc   600
ggcgtgaatt acatgcactg gtatcagcag aagcccggcc aggcccccag aagatgatc   660
tacgacacca gcaagctggc cagcggcgtg cccgccagat tcagcggcag cggctccggc   720
accagctaca gcctgaccat cagcagcctg gagcctgagg atttcgccgt gtattattgc   780
caccagaggg gcagctacac ctttggcggc ggaaacaaag tggagatcaa gcgctaagat   840
cccaccaccg cgccagcgcc gcgaccacca acaccggcgc ccaccatcgc ctcgcagccc   900
ctgtccctgc gcccagaggc gtgccggcca cgcgcggggg gcgcagtgca cacgaggggg   960
ctggacttcg cctgtgatat cttttgggtg ctggtggtgg ttggtggagt cctggccttgc  1020
tatagcttgc tagtaacagt ggcctttatt attttctggg tgaggagagt gaagttcagc  1080
aggagcgcag acgcccccgc gtaccagcag gccagaagcc agctctataa cgagctcaat  1140
ctaggacgaa gagaggagta cgatgttttg gacaagagac gtggccggga ccctgagatg  1200
ggggaaagc cgaaaggaa gaaccctcag gaaggcctgt acaatgaact gcagaaagat  1260
aagatggcg aggcctacag tgagattggg atgaaaggcg agcgccggag gggcaagggg  1320
cacgatggcc tttaccaggg tctcagtaca gccaccaagg acacctacga cgcccttcac  1380
atgcaggccc tgcctcctcg cagagccgag ggcaggggaa gtcttctaac atgcggggac  1440
gtggaggaaa atcccgggcc catggagttt gggctgagct ggctttttct tgtggctatt  1500
ttaaaaggtg tccagtgcga ggtgcagctg gtggagtctg ggggaggctt ggtccagcca  1560
gggggtcc tgcgcctctc ctgtgcagcc tctggattcg ctttcagtat ctatgacatg  1620
tcttgggtcc gccaggttcc ggggaaggg ctgagtggg tctcatatat tagtagtggt  1680
ggtggtacca cctattaccc ggacactgtg aagggccgct tcaccatctc ccgtgacaat  1740
tcccgcaaca ctctggatct tcaaatgaac agtctgcgcg tcgaggacac ggctgtctat  1800
tattgtgcga gtcatagtgg ctacggtagt agctacggta ttttgtttgc ttactgggga  1860
caaggaaccc tggtcaccgt ctcctcaggt ggaggcggtt caggcggagg tggctctggc  1920
ggtggcggat cggacatcca gatgactcag tctccgtcct ccctgtctgc atctgtagga  1980
gaccgcgtca ccatcacctg ccgtgcaagt caggacatta gcaattattt aaactggctt  2040
caacagaaac cggggaaagc cccgaagctc ctgatttact acacatcaat cttcactca  2100
ggagtcccgt cacgcttcag cggcagtgga tctgggacag aattcactct cacaatcagc  2160
agcctgcagc cggaagattt tgcaacttat tactgtcaac agggtaatac gcttccgtgg  2220
acgtttggcc aggggaccaa actggaaatc aaacgttcgg atccagccga accaaagagc  2280
cccgataaga cccacacctg ccccccctgc cagcccctgc agctgctggg aggccccagc  2340
gtgtttctgt ttccacccaa gccaaaggat accctgatga ttagtagaac acccgaagtg  2400
acctgtgtgg tggtggatgt gtctcacgag gaccccgagg tgaaatttaa ttggtatgtt  2460
gatggtgttg aagtgcacaa cgccaaaacc aaacccagag aggagcagta caattctacc  2520
tatagagtcg tgtctgtgct gacagtgctg catcaggatt ggctgaacgg aaaagaatac  2580
aaatgtaaag tgagcaataa ggcccctgcc ctccaatga aagaccaat tagcaaggcc  2640
aagggcagc caaggagcc caggtgtat acactgccac cagtagaga cgaactgaca  2700
aagaatcagg tgtctctgac atgtctggtg aagggatttt acccatctga tatcgccgtg  2760
gaatgggaat ctaacggcca gcccgagaat aactataaga acccccacc agtgctggat  2820
agcgatggca gctttttct gtattctaag ctgacagtgg ataagtcccg gtggcagcag  2880
ggaaatgtgt ttagctgtag tgtcatgcat gaggccctgc acaatcacta tacccagaaa  2940
tctctgagtc tgagcccagg caagaaggac cccaagttct gggtcctggt ggtggtggga  3000
ggcgtgctgg cctgttactc tctcctggtg accgtggcct tcatcatctt tgggtgcgc  3060
tcccgggtga gttttctcg ctctgccgat gccccagcct atcagcaggg ccagaatcag  3120
ctgtacaatg aactgaacct gggcaggcgg gaggagtacg acgtgctgga taagcggaga  3180
ggcagagacc ccgagatggg cggcaaacca cggcgaaaa atccccagga gggactctat  3240
aacgagctgc agaaggacaa aatggccgag gctattccg agatcggcat gaagggagag  3300
agaaaacgcg aaagggcca cgacggcctg tatcagggat gtccaccgc tacaaaagat  3360
acatatgatg ccctgcacat gcaggccctg ccacccgat ga                      3402

SEQ ID NO: 14           moltype = AA  length = 1133

```
FEATURE              Location/Qualifiers
REGION               1..1133
                     note = CD19/CD22 'OR' gate construct
source               1..1133
                     mol_type = protein
                     organism = synthetic construct
SEQUENCE: 14
MSLPVTALLL PLALLLHAAR PYPYDVPDYA SLSGGGGSQV QLVQSGAEVK KPGASVKVSC   60
KASGYTFTSN WMHWVRQAPG QGLEWMGEID PSDSYTNYNQ KFKGRVTITV DKSASTAYME  120
LSSLRSEDTA VYYCARGSNP YYYAMDYWGQ GTLVTVSSGG GGSGGGGSGG GGSEIVLTQS  180
PATLSLSPGE RATLSCSASS GVNYMHWYQQ KPGQAPRRWI YDTSKLASGV PARFSGSGSG  240
TSYSLTISSL EPEDFAVYYC HQRGSYTFGG GTKLEIKRSD PTTTPAPRPP TPAPTIASQP  300
LSLRPEACRP AAGGAVHTRG LDFACDIFWV LVVVGGVLAC YSLLVTVAFI IFWVRRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPRRAE GRGSLLTCGD  480
VEENPGPMEF GLSWLFLVAI LKGVQCEVQL VESGGGLVQP GGSLRLSCAA SGFAFSIYDM  540
SWVRQVPGKG LEWVSYISSG GGTTYYPDTV KGRFTISRDN SRNTLDLQMN SLRVEDTAVY  600
YCARHSGYGS SYGVLFAYWG QGTLVTVSSG GGGSGGGGSG GGGSDIQMTQ SPSSLSASVG  660
DRVTITCRAS QDISNYLNWL QQKPGKAPKL LIYYTSILHS GVPSRFSGSG SGTEFTLTIS  720
SLQPEDFATY YCQQGNTLPW TFGQGTKLEI KRSDPAEPKS PDKTHTCPPC PAPELLGGPS  780
VFLFPPKPKD TLMISRTPEV TCVVVDVSHE DPEVKFNWYV DGVEVHNAKT KPREEQYNST  840
YRVVSVLTVL HQDWLNGKEY KCKVSNKALP APIEKTISKA KGQPREPQVY TLPPSRDELT  900
KNQVSLTCLV KGFYPSDIAV EWESNGQPEN NYKTTPPVLD SDGSFFLYSK LTVDKSRWQQ  960
GNVFSCSVMH EALHNHYTQK SLSLSPGKKD PKFWVLVVVG GVLACYSLLV TVAFIIFWVR 1020
SRVKFSRSAD APAYQQGQNQ LYNELNLGRR EEYDVLDKRR GRDPEMGGKP RRKNPQEGLY 1080
NELQKDKMAE AYSEIGMKGE RRRGKGHDGL YQGLSTATKD TYDALHMQAL PPR        1133

SEQ ID NO: 15        moltype = AA  length = 5
FEATURE              Location/Qualifiers
REGION               1..5
                     note = Complementarity determining region (CDR) variable
                      heavy chain (VH) CDR1
source               1..5
                     mol_type = protein
                     organism = synthetic construct
SEQUENCE: 15
SYWMN                                                                5

SEQ ID NO: 16        moltype = AA  length = 16
FEATURE              Location/Qualifiers
REGION               1..16
                     note = VH CDR2
source               1..16
                     mol_type = protein
                     organism = synthetic construct
SEQUENCE: 16
QIWPGDGDTN YNGKFK                                                   16

SEQ ID NO: 17        moltype = AA  length = 15
FEATURE              Location/Qualifiers
REGION               1..15
                     note = VH CDR3
source               1..15
                     mol_type = protein
                     organism = synthetic construct
SEQUENCE: 17
RETTTVGRYY YAMDY                                                    15

SEQ ID NO: 18        moltype = AA  length = 15
FEATURE              Location/Qualifiers
REGION               1..15
                     note = Variable light chain (VL) CDR1
source               1..15
                     mol_type = protein
                     organism = synthetic construct
SEQUENCE: 18
KASQSVDYDG DSYLN                                                    15

SEQ ID NO: 19        moltype = AA  length = 7
FEATURE              Location/Qualifiers
REGION               1..7
                     note = VL CDR2
source               1..7
                     mol_type = protein
                     organism = synthetic construct
SEQUENCE: 19
DASNLVS                                                              7

SEQ ID NO: 20        moltype = AA  length = 9
```

```
FEATURE                 Location/Qualifiers
REGION                  1..9
                        note = VL CDR3
source                  1..9
                        mol_type = protein
                        organism = synthetic construct
SEQUENCE: 20
QQSTEDPWT                                                                    9

SEQ ID NO: 21           moltype = AA  length = 235
FEATURE                 Location/Qualifiers
REGION                  1..235
                        note = chimeric antigen receptor (CAR), Murine CD19ALAb
                         scFv sequence
source                  1..235
                        mol_type = protein
                        organism = synthetic construct
SEQUENCE: 21
QVQLQQSGAE LVRPGSSVKI SCKASGYAFS SYWMNWVKQR PGQGLEWIGQ IWPGDGDTNY   60
NGKFKGKATL TADESSSTAY MQLSSLASED SAVYFCARRE TTTVGRYYYA MDYWGQGTTV  120
TVSSDIQLTQ SPASLAVSLG QRATISCKAS QSVDYDGDSY LNWYQQIPGQ PPKLLIYDAS  180
NLVSGIPPRF SGSGSGTDFT LNIHPVEKVD AATYHCQQST EDPWTFGGGT KLEIK       235

SEQ ID NO: 22           moltype = AA  length = 236
FEATURE                 Location/Qualifiers
REGION                  1..236
                        note = CAR, Humanised CD19ALAb scFv sequence - Heavy 19,
                         Kappa 16
source                  1..236
                        mol_type = protein
                        organism = synthetic construct
SEQUENCE: 22
QVQLVQSGAE VKKPGASVKL SCKASGYAFS SYWMNWVRQA PGQSLEWIGQ IWPGDGDTNY   60
NGKFKGRATL TADESARTAY MELSSLRSGD TAVYFCARRE TTTVGRYYYA MDYWGKGTLV  120
TVSSDIQLTQ SPDSLAVSLG ERATINCKAS QSVDYDGDSY LNWYQQKPGQ PPKLLIYDAS  180
NLVSGVPDRF SGSGSGTDFT LTISSLQAAD VAVYHCQQST EDPWTFGQGT KVEIKR      236

SEQ ID NO: 23           moltype = AA  length = 124
FEATURE                 Location/Qualifiers
REGION                  1..124
                        note = CAR, Murine CD19ALAb VH sequence
source                  1..124
                        mol_type = protein
                        organism = synthetic construct
SEQUENCE: 23
QVQLQQSGAE LVRPGSSVKI SCKASGYAFS SYWMNWVKQR PGQGLEWIGQ IWPGDGDTNY   60
NGKFKGKATL TADESSSTAY MQLSSLASED SAVYFCARRE TTTVGRYYYA MDYWGQGTTV  120
TVSS                                                               124

SEQ ID NO: 24           moltype = AA  length = 124
FEATURE                 Location/Qualifiers
REGION                  1..124
                        note = CAR, Humanised CD19ALAb VH sequence
source                  1..124
                        mol_type = protein
                        organism = synthetic construct
SEQUENCE: 24
QVQLVQSGAE VKKPGASVKL SCKASGYAFS SYWMNWVRQA PGQSLEWIGQ IWPGDGDTNY   60
NGKFKGRATL TADESARTAY MELSSLRSGD TAVYFCARRE TTTVGRYYYA MDYWGKGTLV  120
TVSS                                                               124

SEQ ID NO: 25           moltype = AA  length = 111
FEATURE                 Location/Qualifiers
REGION                  1..111
                        note = CAR, Murine CD19ALAb VL sequence
source                  1..111
                        mol_type = protein
                        organism = synthetic construct
SEQUENCE: 25
DIQLTQSPAS LAVSLGQRAT ISCKASQSVD YDGDSYLNWY QQIPGQPPKL LIYDASNLVS   60
GIPPRFSGSG SGTDFTLNIH PVEKVDAATY HCQQSTEDPW TFGGGTKLEI K           111

SEQ ID NO: 26           moltype = AA  length = 112
FEATURE                 Location/Qualifiers
REGION                  1..112
                        note = CAR, Humanised CD19ALAb VL sequence, Kappa16
source                  1..112
                        mol_type = protein
                        organism = synthetic construct
```

-continued

```
SEQUENCE: 26
DIQLTQSPDS LAVSLGERAT INCKASQSVD YDGDSYLNWY QQKPGQPPKL LIYDASNLVS    60
GVPDRFSGSG SGTDFTLTIS SLQAADVAVY HCQQSTEDPW TFGQGTKVEI KR          112

SEQ ID NO: 27              moltype = AA   length = 5
FEATURE                    Location/Qualifiers
REGION                     1..5
                           note = VH CDR1
source                     1..5
                           mol_type = protein
                           organism = synthetic construct
SEQUENCE: 27
NYWIN                                                                 5

SEQ ID NO: 28              moltype = AA   length = 17
FEATURE                    Location/Qualifiers
REGION                     1..17
                           note = VH CDR2
source                     1..17
                           mol_type = protein
                           organism = synthetic construct
SEQUENCE: 28
NIYPSDSFTN YNQKFKD                                                   17

SEQ ID NO: 29              moltype = AA   length = 11
FEATURE                    Location/Qualifiers
REGION                     1..11
                           note = VH CDR3
source                     1..11
                           mol_type = protein
                           organism = synthetic construct
SEQUENCE: 29
DTQERSWYFD V                                                         11

SEQ ID NO: 30              moltype = AA   length = 16
FEATURE                    Location/Qualifiers
REGION                     1..16
                           note = VL CDR1
source                     1..16
                           mol_type = protein
                           organism = synthetic construct
SEQUENCE: 30
RSSQSLVHSN GNTYLH                                                    16

SEQ ID NO: 31              moltype = AA   length = 7
FEATURE                    Location/Qualifiers
REGION                     1..7
                           note = VL CDR2
source                     1..7
                           mol_type = protein
                           organism = synthetic construct
SEQUENCE: 31
KVSNRFS                                                               7

SEQ ID NO: 32              moltype = AA   length = 9
FEATURE                    Location/Qualifiers
REGION                     1..9
                           note = VL CDR3
source                     1..9
                           mol_type = protein
                           organism = synthetic construct
SEQUENCE: 32
SQSTHVPWT                                                             9

SEQ ID NO: 33              moltype = AA   length = 232
FEATURE                    Location/Qualifiers
REGION                     1..232
                           note = CAR, Murine CD22ALAb scFv sequence
source                     1..232
                           mol_type = protein
                           organism = synthetic construct
SEQUENCE: 33
QVQLQQPGAE LVRPGASVKL SCKASGYTFT NYWINWVKQR PGQGLEWIGN IYPSDSFTNY    60
NQKFKDKATL TVDKSSSTAY MQLSSPTSED SAVYYCTRDT QERSWYFDVW GAGTTVTVSS   120
DVVMTQTPLS LPVSLGDQAS ISCRSSQSLV HSNGNTYLHW YLQKPGQSPK LLIYKVSNRF   180
SGVPDRFSGS GSGTDFTLKI SRVEAEDLGL YFCSQSTHVP WTFGGGTKLE IK           232

SEQ ID NO: 34              moltype = AA   length = 232
FEATURE                    Location/Qualifiers
```

```
REGION                     1..232
                           note = CAR, Humanised CD22ALAb scFv sequence
source                     1..232
                           mol_type = protein
                           organism = synthetic construct
SEQUENCE: 34
EVQLVESGAE VKKPGSSVKV SCKASGYTFT NYWINWVRQA PGQGLEWIGN IYPSDSFTNY    60
NQKFKDRATL TVDKSTSTAY LELRNLRSDD TAVYYCTRDT QERSWYFDVW GQGTLVTVSS   120
DIVMTQSPAT LSVSPGERAT LSCRSSQSLV HSNGNTYLHW YQQKPGQAPR LLIYKVSNRF   180
SGVPARFSGS GSGVEFTLTI SSLQSEDFAV YYCSQSTHVP WTFGQGTRLE IK           232

SEQ ID NO: 35              moltype = AA   length = 120
FEATURE                    Location/Qualifiers
REGION                     1..120
                           note = CAR, Murine CD22ALAb VH sequence
source                     1..120
                           mol_type = protein
                           organism = synthetic construct
SEQUENCE: 35
QVQLQQPGAE LVRPGASVKL SCKASGYTFT NYWINWVKQR PGQGLEWIGN IYPSDSFTNY    60
NQKFKDKATL TVDKSSSTAY MQLSSPTSED SAVYYCTRDT QERSWYFDVW GAGTTVTVSS   120

SEQ ID NO: 36              moltype = AA   length = 120
FEATURE                    Location/Qualifiers
REGION                     1..120
                           note = CAR, Humanised CD22ALAb VH sequence
source                     1..120
                           mol_type = protein
                           organism = synthetic construct
SEQUENCE: 36
EVQLVESGAE VKKPGSSVKV SCKASGYTFT NYWINWVRQA PGQGLEWIGN IYPSDSFTNY    60
NQKFKDRATL TVDKSTSTAY LELRNLRSDD TAVYYCTRDT QERSWYFDVW GQGTLVTVSS   120

SEQ ID NO: 37              moltype = AA   length = 112
FEATURE                    Location/Qualifiers
REGION                     1..112
                           note = CAR, Murine CD22ALAb VL sequence
source                     1..112
                           mol_type = protein
                           organism = synthetic construct
SEQUENCE: 37
DVVMTQTPLS LPVSLGDQAS ISCRSSQSLV HSNGNTYLHW YLQKPGQSPK LLIYKVSNRF    60
SGVPDRFSGS GSGTDFTLKI SRVEAEDLGL YFCSQSTHVP WTFGGGTKLE IK           112

SEQ ID NO: 38              moltype = AA   length = 112
FEATURE                    Location/Qualifiers
REGION                     1..112
                           note = CAR, Humanised CD22ALAb VL sequence
source                     1..112
                           mol_type = protein
                           organism = synthetic construct
SEQUENCE: 38
DIVMTQSPAT LSVSPGERAT LSCRSSQSLV HSNGNTYLHW YQQKPGQAPR LLIYKVSNRF    60
SGVPARFSGS GSGVEFTLTI SSLQSEDFAV YYCSQSTHVP WTFGQGTRLE IK           112

SEQ ID NO: 39              moltype = AA   length = 236
FEATURE                    Location/Qualifiers
REGION                     1..236
                           note = CAR, Humanised CD19ALAb scFv sequence - Heavy 19,
                            Kappa 7
source                     1..236
                           mol_type = protein
                           organism = synthetic construct
SEQUENCE: 39
QVQLVQSGAE VKKPGASVKL SCKASGYAFS SYWMNWVRQA PGQSLEWIGQ IWPGDGDTNY    60
NGKFKGRATL TADESARTAY MELSSLRSGD TAVYFCARRE TTTVGRYYYA MDYWGKGTLV   120
TVSSDIQLTQ SPDSLAVSLG ERATINCKAS QSVDYDGDSY LNWYQQKPGQ PPKVLIYDAS   180
NLVSGVPDRF SGSGSGTDFT LTISSLQAAD VAVYYCQQST EDPWTFGQGT KVEIKR       236

SEQ ID NO: 40              moltype = AA   length = 112
FEATURE                    Location/Qualifiers
REGION                     1..112
                           note = CAR, Humanised CD19ALAb VL sequence, Kappa 7
source                     1..112
                           mol_type = protein
                           organism = synthetic construct
SEQUENCE: 40
DIQLTQSPDS LAVSLGERAT INCKASQSVD YDGDSYLNWY QQKPGQPPKV LIYDASNLVS    60
GVPDRFSGSG SGTDFTLTIS SLQAADVAVY YCQQSTEDPW TFGQGTKVEI KR           112
```

```
SEQ ID NO: 41              moltype = AA   length = 40
FEATURE                    Location/Qualifiers
REGION                     1..40
                           note = CD28 co-stimulatory endodomain
source                     1..40
                           mol_type = protein
                           organism = synthetic construct
SEQUENCE: 41
SKRSRLLHSD YMNMTPRRPG PTRKHYQPYA PPRDFAAYRS                           40

SEQ ID NO: 42              moltype = AA   length = 36
FEATURE                    Location/Qualifiers
REGION                     1..36
                           note = OX40 endodomain
source                     1..36
                           mol_type = protein
                           organism = synthetic construct
SEQUENCE: 42
RDQRLPPDAH KPPGGGSFRT PIQEEQADAH STLAKI                               36

SEQ ID NO: 43              moltype = AA   length = 42
FEATURE                    Location/Qualifiers
REGION                     1..42
                           note = 4-1BB endodomain
source                     1..42
                           mol_type = protein
                           organism = synthetic construct
SEQUENCE: 43
KRGRKKLLYI FKQPFMRPVQ TTQEEDGCSC RFPEEEEGGC EL                        42

SEQ ID NO: 44              moltype = AA   length = 112
FEATURE                    Location/Qualifiers
REGION                     1..112
                           note = CD3zeta endodomain
source                     1..112
                           mol_type = protein
                           organism = synthetic construct
SEQUENCE: 44
RVKFSRSADA PAYQQGQNQL YNELNLGRRE EYDVLDKRRG RDPEMGGKPR RKNPQEGLYN      60
ELQKDKMAEA YSEIGMKGER RRGKGHDGLY QGLSTATKDT YDALHMQALP PR             112

SEQ ID NO: 45              moltype = AA   length = 24
FEATURE                    Location/Qualifiers
REGION                     1..24
                           note = Tyrp-1 transmembrane sequence
source                     1..24
                           mol_type = protein
                           organism = synthetic construct
SEQUENCE: 45
IIAIAVVGAL LLVALIFGTA SYLI                                            24

SEQ ID NO: 46              moltype = AA   length = 258
FEATURE                    Location/Qualifiers
source                     1..258
                           mol_type = protein
                           organism = Homo sapiens
SEQUENCE: 46
EEPLVVKVEE GDNAVLQCLK GTSDGPTQQL TWSRESPLKP FLKLSLGLPG LGIHMRPLAI      60
WLFIFNVSQQ MGGFYLCQPG PPSEKAWQPG WTVNVEGSGE LFRWNVSDLG GLGCGLKNRS     120
SEGPSSPSGK LMSPKLYVWA KDRPEIWEGE PPCLPPRDSL NQSLSQDLTM APGSTLWLSC     180
GVPPDSVSRG PLSWTHVHPK GPKSLLSLEL KDDRPARDMW VMETGLLLPR ATAQDAGKYY     240
CHRGNLTMSF HLEITARP                                                  258

SEQ ID NO: 47              moltype =    length =
SEQUENCE: 47
000

SEQ ID NO: 48              moltype = DNA   length = 1139
FEATURE                    Location/Qualifiers
source                     1..1139
                           mol_type = other DNA
                           organism = Homo sapiens
SEQUENCE: 48
atcccgccga gcccaaatct cctgacaaaa ctcacacatg cccaccgtgc ccagcacctg      60
aactcctggg gggaccgtca gtcttcctct tccccccaaa acccaaggac accctcatga    120
tctcccggac ccctgaggtc acatgcgtgt ggtggacgt gagccacgaa gaccctgagg     180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
```

```
ggctgaatgg caaggagtac aagtgcaagg tctccaacaa agccctccca gcccccatcg  360
agaaaaccat ctccaaagcc aaagggcagc cccgagaacc acaggtgtac acctgcccc   420
catcccggga tgagctgacc aagaaccagg tcagcctgac ctgcctggtc aaaggcttct  480
atcccagcga catcgccgtg gagtgggaga gcaatgggca accggagaac aactacaaga  540
ccacgcctcc cgtgctggac tccgacggct ccttcttcct ctacagcaag ctcaccgtgg  600
acaagagcag gtggcagcag gggaacgtct tctcatgctc cgtgatgcac gaggctctgc  660
acaaccacta cacgcagaag agcctctccc tgtctccggg taaaaaagat cccaaatttt  720
gggtgctggt ggtggttggt ggagtcctgg cttgctatag cttgctagta acagtggcct  780
ttattatttt ctgggtgagg agagtgaagt tcagcaggag cgcagacgcc cccgcgtacc  840
agcagggcca gaaccagctc tataacgagc tcaatctagg acgaagagag gagtacgatg  900
ttttggacaa gagacgtggc cgggaccctg agatggggg aaagccgaga aggaagaacc   960
ctcaggaagg cctgtacaat gaactgcaga aagataagat ggcggaggcc tacagtgaga 1020
ttgggatgaa aggcgagcgc cggaggggca agggcacga tggcctttac cagggtctca  1080
gtacagccac caaggacacc tacgacgccc ttcacatgca ggccctgcct cctcgcgag  1139

SEQ ID NO: 49          moltype = DNA  length = 1139
FEATURE                Location/Qualifiers
misc_feature           1..1139
                       note = codon-wobbled HCH2CH3-CD28tmZeta
source                 1..1139
                       mol_type = other DNA
                       organism = synthetic construct
SEQUENCE: 49
atccagccga accaaagagc cccgataaga cccacacctg tccccctgc ccagcccag    60
agctgctggg aggccccagc gtgtttctgt ttccacccaa gccaaggat accctgatga  120
ttagtagaac acccgaagtg acctgtgtgg tggtggatgt gtctcacgag gaccccgagg  180
tgaaatttaa ttggtatgtt gatggtgttg aagtgcacaa cgccaaaacc aaacccagag  240
aggagcagta caattctacc tatagagtcg tgtctgtgct gacagtgctg catcaggatt  300
ggctgaacgg aaaagaatac aaatgtaaag tgagcaataa ggccctgccc gctccaattg  360
agaagacaat tagcaaggcc aagggccagc caaggtgtat acactgccac              420
ccagtagaga cgaactgaca aagaatcagg tgtctctgac atgtctggtg aagggatttt  480
acccatctga tatcgccgtg gaatgggaat ctaacggcca gcccgagaat aactataaga  540
caacccccacc agtgctggat agcgatggca gcttttttct gtattctaag ctgacagtgg  600
ataagtcccg gtggcagcag ggaaatgtgt ttagctgtag tgtcatgcat gaggcctgc   660
acaatcacta tacccagaaa tctctgagtc tgagcccagg caagaaggac cccaagttct  720
gggtcctggt ggtggtggga ggcgtgctgg cctgttactc tctcctggtg accgtggcct  780
tcatcatctt ttgggtgcgc tcccgggtga agttttctcg ctctgccgat gccccagcct  840
atcagcaggg ccagaatcag ctgtacaatg aactgaacct gggcaggcgg gaggagtacg  900
acgtgctgga taagcggaga gcagagacc ccgagatggg cggcaaacca cggcgcaaaa   960
atccccagga gggactctat aacgagctgc agaaggacaa aatggccgag gcctattccg  1020
agatcggcat gaagggagag agaagacgcg gaaagggcca cgacgcctg tatcagggat   1080
tgtccaccgc tacaaagat acatatgatg ccctgcacat gcaggccctg ccacccaga    1139
```